United States Patent
Lee et al.

(10) Patent No.: US 11,208,644 B2
(45) Date of Patent: Dec. 28, 2021

(54) RECOMBINANT GLYCOPROTEINS AND USES THEREOF

(71) Applicant: Genzyme Corporation, Cambridge, MA (US)

(72) Inventors: Karen Lee, Bridgewater, NJ (US); Christopher Hwang, Bridgewater, NJ (US); Christine DeMaria, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/030,555

(22) PCT Filed: Oct. 22, 2014

(86) PCT No.: PCT/US2014/061789
§ 371 (c)(1),
(2) Date: Apr. 19, 2016

(87) PCT Pub. No.: WO2015/061464
PCT Pub. Date: Apr. 30, 2015

(65) Prior Publication Data
US 2016/0264953 A1    Sep. 15, 2016

Related U.S. Application Data

(60) Provisional application No. 61/901,942, filed on Nov. 8, 2013, provisional application No. 61/894,879, filed on Oct. 23, 2013.

(51) Int. Cl.
| | |
|---|---|
| *C12N 9/40* | (2006.01) |
| *A61K 38/47* | (2006.01) |
| *A61K 38/00* | (2006.01) |
| *C12P 21/00* | (2006.01) |
| *C07K 14/705* | (2006.01) |
| *A61K 9/00* | (2006.01) |
| *A61K 9/19* | (2006.01) |
| *A61K 45/06* | (2006.01) |
| *C12N 5/00* | (2006.01) |

(52) U.S. Cl.
CPC .......... *C12N 9/2465* (2013.01); *A61K 9/0019* (2013.01); *A61K 9/19* (2013.01); *A61K 38/47* (2013.01); *A61K 45/06* (2013.01); *C07K 14/70592* (2013.01); *C12N 5/00* (2013.01); *C12P 21/005* (2013.01); *C12Y 302/01022* (2013.01); *A61K 38/00* (2013.01); *C12N 2510/00* (2013.01)

(58) Field of Classification Search
CPC .... C12N 9/2465; C12N 5/00; C12N 2510/00; C07K 14/70592; C12P 21/005; C12Y 302/01022; A61K 38/47; A61K 9/19; A61K 9/0019; A61K 45/06; A61K 38/00
See application file for complete search history.

(56) References Cited

U.S. PATENT DOCUMENTS

| | | | |
|---|---|---|---|
| 5,356,804 A | 10/1994 | Desnick et al. | |
| 6,066,626 A | 5/2000 | Yew et al. | |
| 6,083,725 A | 7/2000 | Selden et al. | |
| 2003/0152560 A1 | 8/2003 | Selden et al. | |
| 2007/0031945 A1* | 2/2007 | Daniel ................... | A61K 38/47 435/101 |

FOREIGN PATENT DOCUMENTS

| | | |
|---|---|---|
| CL | 201401960 | 7/2014 |
| WO | WO 94/12628 A1 | 6/1994 |
| WO | 2009/027041 A1 | 3/2009 |
| WO | WO 2013/110778 | 8/2013 |

OTHER PUBLICATIONS

Rasmussen et al., Cell Culture Engineering VI, pp. 31-42, M.J. Betenbaugh et al. (eds.),1998.*
European Communication in Application No. 14796346.6, dated Feb. 21, 2017, 3 pages.
Chilean Office Action in Application No. 2016-000961, dated Aug. 22, 2017, 16 pages.
Columbian Office Action in Application No. 16120696, dated Oct. 6, 2017, 24 pages.
European Examination in Application No. 14796346.6, dated Nov. 14, 2017, 6 pages.
Israel Office Action in Application No. 245255, dated Oct. 30, 2017, 10 pages.
Youngsoo et al., "Enhanced sialylation and in vivo efficacy of recombinant and in vivo efficacy of recombinant human alfagalactosidase through in vitro glycosylation," BMB Reports 46(3):157-162, Mar. 31, 2013.
Columbian Office Action in Columbian Application No. 16120696, dated Jul. 14, 2016, 5 pages.
International Preliminary Report on Patentability in International Application No. PCT/US2014/061789, dated Apr. 26, 2016, 9 pages.
International Search Report and Written Opinion in International Application No. PCT/US2014/061789, dated Aug. 7, 2015, 15 pages.

(Continued)

*Primary Examiner* — Delia M Ramirez
(74) *Attorney, Agent, or Firm* — McNeill Baur PLLC

(57) ABSTRACT

Provided herein are recombinant glycoproteins (e.g., recombinant human α-galactosidase-A proteins) with an altered (e.g., improved) glycosylation profile, and pharmaceutical compositions and kits including one or more of these proteins. Also provided are methods of generating a mammalian cell useful for recombinant expression of a glycoprotein (e.g., recombinant human α-galactosidase-A), methods of producing recombinant glycoproteins, and methods of treatment that include administering to a subject at least one of the recombinant glycoproteins (e.g., recombinant human α-galactosidase-A protein).

24 Claims, 34 Drawing Sheets
Specification includes a Sequence Listing.

(56) References Cited

OTHER PUBLICATIONS

Ioannou et al., "Overexpression of human alpha-galactosidase a results in its intracellular aggregation, crystallization in lysosomes, and selective secretion", The Journal of Cell Biology, The Rockefeller University Press, vol. 119, No. 5, Dec. 1, 1992, pp. 1137-1150.
Lee et al., "A biochemical and pharmacological comparison of enzyme replacement therapies for the glycolipid storage disorder Fabry disease", Glycobiology, Oxford University Press, vol. 13, No. 4, Apr. 1, 2003, pp. 305-313.
Matsuura et al., "Human alpha-galactosidase A: characterization of the N-linked oligosaccharides on the intracellular and secreted glycoforms over expressed by Chinese hamster ovary cells". Glycobiology, Oxford University Press, vol. 8, No. 4, Apr. 1, 1998, pp. 329-339.
Rote Liste, "50. Hypophysen-, Hypothalamushormone, andere regulatorische Peptide u. ihre Hemmstoffe," Chapter 50, ed. 2008, 20 pages.
Sohn et al., "Enhanced sialylation and in vivo efficacy of recombinant human (alpha)-galactosidase through in vitro glycosylation", BMB Reports, vol. 46, No. 3, Mar. 31, 2013, pp. 157-162.
Chilean Office Action in Chilean Patent Appl. No. 201600961, dated Feb. 15, 2018, 7 pages.
Eurasian Office Action in Eurasian Patent Appl. No. 201690826, dated Mar. 29, 2018, 10 pages.
Gulf Cooperation Council Office Action in GCC Patent Appl. No. GC 2014-28171, dated Feb. 11, 2017, 6 pages.
Moroccan Office Action in Moroccan Patent Appl. No. 39053, dated Dec. 28, 2017.
Taiwanese Office Action in Taiwanese Patent Appl. No. 1031362772, dated Apr. 3, 2018, 9 pages.
European Communication in Application No. 14796346.6, dated Sep. 18, 2018, 3 pages.
European Communication in Application No. 14796346.6, dated Feb. 21, 2017, 4 pages.
Japanese Office Action in Application No. 2016-526026, dated Oct. 16, 2018, 7 pages.
Russian Office Action in Application No. 201690826, dated Oct. 11, 2017, 4 pages.
Saudi Arabia Examination Report in Application No. GC 2014-28171, dated Nov. 2, 2017, 6 pages.
Written Opinion in Eurasian Patent Application No. 201690826/28, dated Nov. 8, 2018.
Saudi Arabia Examination Report in GC Patent Appl. No. GC 2014-28171, dated Oct. 7, 2018, 4 pages.
Written Opinion in Pakistan Patent Application No. 748/2014, dated Feb. 13, 2017.
Written Opinion in Thailand Patent Application No. 1601001949, dated Nov. 9, 2017.
Chinese Office Action in Patent Application No. 201480070424.3, dated Mar. 6, 2019, 10 pages.
European Communication in Patent Application No. 14796346.6, dated Jun. 11, 2019, 3 pages.
Indonesia Office Action in Patent Application No. P00201603378, dated Jun. 17, 2019, 8 pages.
Rasmussen et al., "Isolation, characterization and recombinant protein expression in Veggie-CHO: A serum-free CHO host cell line," Cytotechnology, 28(1-3): 31-42, Nov. 1998.
Ukraine Office Action in Patent Application No. a 2016 05455, dated Feb. 8, 2019, 5 pages.
Written Opinion in Dominican Republic Patent Application No. P2016-0079, dated May 7, 2019.
Written Opinion in Malaysia Patent Application No. PI 2016700943, dated Apr. 30, 2019, 2 pages.
Mexican Office Action in Patent Application No. MX/a/2016/005321, dated Aug. 14, 2019, 3 pages.
Moroccan Office Action in Patent Application No. 39053, dated Oct. 8, 2019, 10 pages (with English translation).
Philippines Office Action in Patent Application No. 1-2016-500708, dated Oct. 7, 2019, 4 pages.
Australian Office Action in Patent Application No. 2014340152, dated Jan. 7, 2020, 25 pages.
Brazil Office Action in Patent Application No. BR 112016008086-6, dated Nov. 12, 2019, 9 pages.
India Office Action in Patent Application No. 201637014506, dated Feb. 6, 2020, 13 pages.
Indonesia Office Action in Patent Application No. P2016-0079, dated May 7, 2019, 3 pages.
Mexican Office Action in Patent Application No. MX/a/2016/005321, dated Feb. 21, 2020, 5 pages.
Peruvian Office Action in Patent Application No. 000543-2016/DIN, dated Jan. 28, 2020, 21 pages.
Written Opinion in Israel Patent Application No. 245255, dated Feb. 14, 2019, 4 pages.
Written Opinion in Ukraine Patent Application No. 2016-05455, dated Feb. 12, 2019, 5 pages.
Satoru Kamoda et al., Journal of Chromatograph A, vol. 1133, No. 1-2; "Capillary electrophoresis with laser-induced fluorescence detection for detailed studies on N-linked oligosaccharide profile of therapeutic recombinant monoclonal antibodies;" May 28, 2006.
Cairns V.R. et al., "Utilization of Non-AUG Initiation Codons in a Flow Cytometric Method for Efficient Selection of Recombinant Cell Lines", Biotechnology and Bioengineering, 2011, vol. 108, No. 11, pp. 2611-2622.

\* cited by examiner

| Lysosomal storage diseases and associated enzymatic defects | |
|---|---|
| Disease | Enzymatic Defect |
| Pompe disease | acid α-glucosidase (e.g., Myozyme®, Lumizyme®) |
| MPSI* (Hurler disease) | α-L-iduronidase (e.g., Aldurazyme®) |
| MPSII (Hunter disease) | iduronate sulfatase |
| MPSIII (Sanfilippo) | heparan N-sulfatase |
| MPS IV (Morquio A) | galactose-6-sulfatase |
| MPS IV (Morquio B) | acid β-galactosidase |
| MPS VII (Sly disease) | β-glucoronidase |
| I-cell disease | N-acetylglucosamine-1-phosphotransferase |
| Schindler disease | α-N-acetylgalactosaminidase (α-galactosidase B) |
| Wolman disease | acid lipase |
| Cholestrol ester storage disease | acid lipase |
| Farber disease | lysosomal acid ceramidase |
| Niemann-Pick disease | acid sphingomyelinase |
| Gaucher disease | β-glucosidase (e.g. Cerezyme®, Ceredase®) |
| Krabbe disease | galactosylceramidase |
| Fabry disease | α-galactosidase A |
| GM1 gangliosidosis | acid β-galactosidase |
| Galactosialidosis | β-galactosidase and neuraminidase |
| Tay-Sach's disease | hexosaminidase A |
| Sandhoff disease | hexosaminidase A and B |

*MPS = mucopolysaccaridosis

FIG. 1

Precursor Human Alpha-Galactosidase-A Protein and cDNA (SEQ ID NOs: 1 and 2)

```
ATG CAG CTG AGG AAC CCA GAA CTA CAT CTG GGC TGC GCG CTT GCG CTT
Met Gln Leu Arg Asn Pro Glu Leu His Leu Gly Cys Ala Leu Ala Leu
 1               5                   10                  15

CGC TTC CTG GCC CTC GTT TCC TGG GAC ATC CCT GGG GCT AGA GCA CTG
Arg Phe Leu Ala Leu Val Ser Trp Asp Ile Pro Gly Ala Arg Ala Leu
                20                  25                  30

GAC AAT GGA TTG GCA AGG ACG CCT ACC ATG GGC TGG CTG CAC TGG GAG
Asp Asn Gly Leu Ala Arg Thr Pro Thr Met Gly Trp Leu His Trp Glu
            35                  40                  45

CGC TTC ATG TGC AAC CTT GAC TGC CAG GAA GAG CCA GAT TCC TGC ATC
Arg Phe Met Cys Asn Leu Asp Cys Gln Glu Glu Pro Asp Ser Cys Ile
        50                  55                  60

AGT GAG AAG CTC TTC ATG GAG ATG GCA GAG CTC ATG GTC TCA GAA GGC
Ser Glu Lys Leu Phe Met Glu Met Ala Glu Leu Met Val Ser Glu Gly
 65                 70                  75                  80

TGG AAG GAT GCA GGT TAT GAG TAC CTC TGC ATT GAT GAC TGT TGG ATG
Trp Lys Asp Ala Gly Tyr Glu Tyr Leu Cys Ile Asp Asp Cys Trp Met
                85                  90                  95

GCT CCC CAA AGA GAT TCA GAA GGC AGA CTT CAG GCA GAC CCT CAG CGC
Ala Pro Gln Arg Asp Ser Glu Gly Arg Leu Gln Ala Asp Pro Gln Arg
            100                 105                 110

TTT CCT CAT GGG ATT CGC CAG CTA GCT AAT TAT GTT CAC AGC AAA GGA
Phe Pro His Gly Ile Arg Gln Leu Ala Asn Tyr Val His Ser Lys Gly
        115                 120                 125

CTG AAG CTA GGG ATT TAT GCA GAT GTT GGA AAT AAA ACC TGC GCA GGC
Leu Lys Leu Gly Ile Tyr Ala Asp Val Gly Asn Lys Thr Cys Ala Gly
        130                 135                 140

TTC CCT GGG AGT TTT GGA TAC TAC GAC ATT GAT GCC CAG ACC TTT GCT
Phe Pro Gly Ser Phe Gly Tyr Tyr Asp Ile Asp Ala Gln Thr Phe Ala
145                 150                 155                 160

GAC TGG GGA GTA GAT CTG CTA AAA TTT GAT GGT TGT TAC TGT GAC AGT
Asp Trp Gly Val Asp Leu Leu Lys Phe Asp Gly Cys Tyr Cys Asp Ser
                165                 170                 175

TTG GAA AAT TTG GCA GAT GGT TAT AAG CAC ATG TCC TTG GCC CTG AAT
Leu Glu Asn Leu Ala Asp Gly Tyr Lys His Met Ser Leu Ala Leu Asn
            180                 185                 190
```

Figure 2

```
AGG ACT GGC AGA AGC ATT GTG TAC TCC TGT GAG TGG CCT CTT TAT ATG
Arg Thr Gly Arg Ser Ile Val Tyr Ser Cys Glu Trp Pro Leu Tyr Met
            195                 200                 205

TGG CCC TTT CAA AAG CCC AAT TAT ACA GAA ATC CGA CAG TAC TGC AAT
Trp Pro Phe Gln Lys Pro Asn Tyr Thr Glu Ile Arg Gln Tyr Cys Asn
    210                 215                 220

CAC TGG CGA AAT TTT GCT GAC ATT GAT GAT TCC TGG AAA AGT ATA AAG
His Trp Arg Asn Phe Ala Asp Ile Asp Asp Ser Trp Lys Ser Ile Lys
225                 230                 235                 240

AGT ATC TTG GAC TGG ACA TCT TTT AAC CAG GAG AGA ATT GTT GAT GTT
Ser Ile Leu Asp Trp Thr Ser Phe Asn Gln Glu Arg Ile Val Asp Val
                245                 250                 255

GCT GGA CCA GGG GGT TGG AAT GAC CCA GAT ATG TTA GTG ATT GGC AAC
Ala Gly Pro Gly Gly Trp Asn Asp Pro Asp Met Leu Val Ile Gly Asn
            260                 265                 270

TTT GGC CTC AGC TGG AAT CAG CAA GTA ACT CAG ATG GCC CTC TGG GCT
Phe Gly Leu Ser Trp Asn Gln Gln Val Thr Gln Met Ala Leu Trp Ala
        275                 280                 285

ATC ATG GCT GCT CCT TTA TTC ATG TCT AAT GAC CTC CGA CAC ATC AGC
Ile Met Ala Ala Pro Leu Phe Met Ser Asn Asp Leu Arg His Ile Ser
        290                 295                 300

CCT CAA GCC AAA GCT CTC CTT CAG GAT AAG GAC GTA ATT GCC ATC AAT
Pro Gln Ala Lys Ala Leu Leu Gln Asp Lys Asp Val Ile Ala Ile Asn
305                 310                 315                 320

CAG GAC CCC TTG GGC AAG CAA GGG TAC CAG CTT AGA CAG GGA GAC AAC
Gln Asp Pro Leu Gly Lys Gln Gly Tyr Gln Leu Arg Gln Gly Asp Asn
                325                 330                 335

TTT GAA GTG TGG GAA CGA CCT CTC TCA GGC TTA GCC TGG GCT GTA GCT
Phe Glu Val Trp Glu Arg Pro Leu Ser Gly Leu Ala Trp Ala Val Ala
            340                 345                 350

ATG ATA AAC CGG CAG GAG ATT GGT GGA CCT CGC TCT TAT ACC ATC GCA
Met Ile Asn Arg Gln Glu Ile Gly Gly Pro Arg Ser Tyr Thr Ile Ala
        355                 360                 365

GTT GCT TCC CTG GGT AAA GGA GTG GCC TGT AAT CCT GCC TGC TTC ATC
Val Ala Ser Leu Gly Lys Gly Val Ala Cys Asn Pro Ala Cys Phe Ile
        370                 375                 380
```

Figure 2 (cont.)

```
ACA CAG CTC CTC CCT GTG AAA AGG AAG CTA GGG TTC TAT GAA TGG ACT
Thr Gln Leu Leu Pro Val Lys Arg Lys Leu Gly Phe Tyr Glu Trp Thr
385                 390                 395                 400

TCA AGG TTA AGA AGT CAC ATA AAT CCC ACA GGC ACT GTT TTG CTT CAG
Ser Arg Leu Arg Ser His Ile Asn Pro Thr Gly Thr Val Leu Leu Gln
                405                 410                 415

CTA GAA AAT ACA ATG CAG ATG TCA TTA AAA GAC TTA CTT
Leu Glu Asn Thr Met Gln Met Ser Leu Lys Asp Leu Leu
                420                 425
```

Mature Human Alpha-Galactosidase-A (SEQ ID NO: 3)

```
Leu Asp Asn Gly Leu Ala Arg Thr Pro Thr Met Gly Trp Leu His Trp   16
Glu Arg Phe Met Cys Asn Leu Asp Cys Gln Glu Glu Pro Asp Ser Cys   32
Ile Ser Glu Lys Leu Phe Met Glu Met Ala Glu Leu Met Val Ser Glu   48
Gly Trp Lys Asp Ala Gly Tyr Glu Tyr Leu Cys Ile Asp Asp Cys Trp   64
Met Ala Pro Gln Arg Asp Ser Glu Gly Arg Leu Gln Ala Asp Pro Gln   80
Arg Phe Pro His Gly Ile Arg Gln Leu Ala Asn Tyr Val His Ser Lys   96
Gly Leu Lys Leu Gly Ile Tyr Ala Asp Val Gly Asn Lys Thr Cys Ala  112
Gly Phe Pro Gly Ser Phe Gly Tyr Tyr Asp Ile Asp Ala Gln Thr Phe  128
Ala Asp Trp Gly Val Asp Leu Leu Lys Phe Asp Gly Cys Tyr Cys Asp  144
Ser Leu Glu Asn Leu Ala Asp Gly Tyr Lys His Met Ser Leu Ala Leu  160
Asn Arg Thr Gly Arg Ser Ile Val Tyr Ser Vys Glu Trp Pro Leu Tyr  176
Met Trp Pro Phe Gln Lys Pro Asn Tyr Thr Glu Ile Arg Gln Tyr Cys  192
Asn His Trp Arg Asn Phe Ala Asp Ile Asp Asp Ser Trp Lys Ser Ile  208
Lys Ser Ile Leu Asp Trp Thr Ser Phe Asn Gln Glu Arg Ile Val Asp  224
Val Ala Gly Pro Gly Gly trp Asn Asp Pro Asp Met Leu Val Ile Gly  240
Asn Phe Gly Leu Ser Trp Asn Gln Gln Val Thr Gln Met Ala Leu Trp  256
Ala Ile Met Ala Ala Pro Leu Phe Met Ser Asn Asp Leu Arg His Ile  272
Ser Pro Gln Ala Lys Ala Leu Leu Gln Asp Lys Asp Val Ile Ala Ile  288
Asn Gln Asp Pro Leu Gly Lys Gln Gly Tyr GLn Leu Arg Gln Gly Asp  304
Asn Phe Gly Val Trp Glu Arg Pro Leu Ser Gly Leu Ala Trp Ala Val  320
Ala Met Ile Asn Arg Gln Glu Ile Gly Gly Pro Arg Ser Tyr Thr Ile  336
Ala Val Ala Ser Leu Gly Lys Gly Val Ala Cys Asn Pro Ala Cys Phe  352
Ile Thr Gln Leu Leu Pro Val Lys Arg Lys Leu Gly Phe Tyr Glu Trp  368
Thr Ser Arg Leu Arg Ser His Ile Asn Pro Thr Gly Thr Val Leu Leu  384
Gln Leu Gly Asn Thr Met Gln Met Ser Leu Lys Asp Leu Leu          398
```

Figure 2 (cont.)

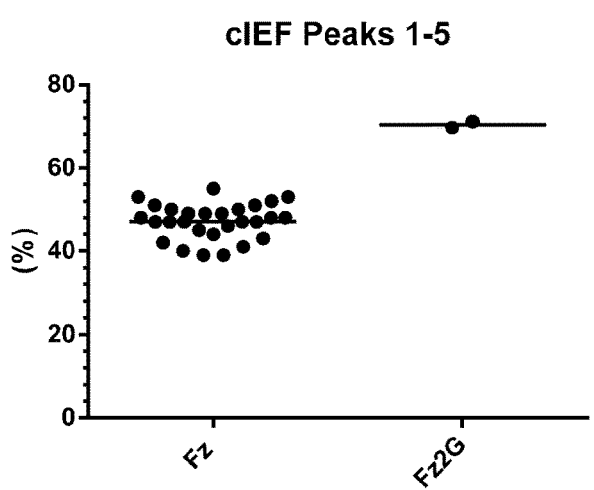
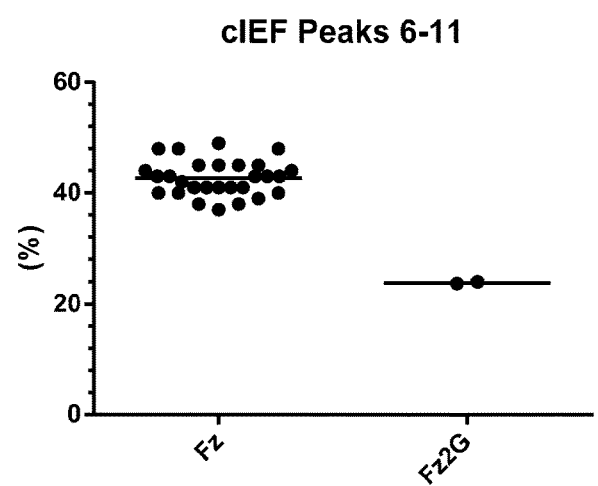
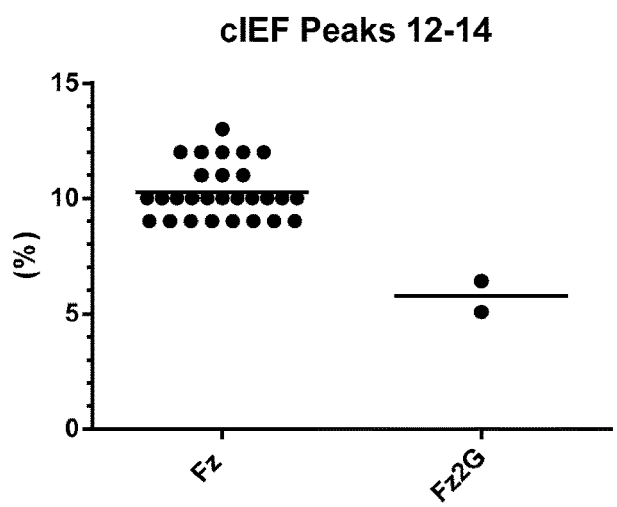
FIG. 32

SEQUENCE LISTING

<160> NUMBER OF SEQ ID NOS: 3

<210> SEQ ID NO 1
<211> LENGTH: 1287
<212> TYPE: DNA
<213> ORGANISM: Homo sapiens

<400> SEQUENCE: 1

```
atgcagctga ggaacccaga actacatctg ggctgcgcgc ttgcgcttcg cttcctggcc    60
ctcgtttcct gggacatccc tggggctaga gcactggaca atggattggc aaggacgcct   120
accatgggct ggctgcactg ggagcgcttc atgtgcaacc ttgactgcca ggaagagcca   180
gattcctgca tcagtgagaa gctcttcatg gagatggcag agctcatggt ctcagaaggc   240
tggaaggatg caggttatga gtacctctgc attgatgact gttggatggc tccccaaaga   300
gattcagaag gcagacttca ggcagaccct cagcgctttc ctcatgggat tcgccagcta   360
gctaattatg ttcacagcaa aggactgaag ctagggattt atgcagatgt tggaaataaa   420
acctgcgcag gcttccctgg gagttttgga tactacgaca ttgatgccca gacctttgct   480
gactggggag tagatctgct aaaatttgat ggttgttact gtgacagttt ggaaaatttg   540
gcagatggtt ataagcacat gtccttggcc ctgaataggc tggcagaag cattgtgtac   600
tcctgtgagt ggcctcttta tatgtggccc tttcaaaagc ccaattatac agaaatccga   660
cagtactgca atcactggcg aaattttgct gacattgatg attcctggaa aagtataaag   720
agtatcttgg actggacatc ttttaaccag gagagaattg ttgatgttgc tggaccaggg   780
ggttggaatg acccagatat gttagtgatt ggcaactttg gcctcagctg aatcagcaa   840
gtaactcaga tggccctctg ggctatcatg gctgctcctt tattcatgtc taatgacctc   900
cgacacatca gccctcaagc caaagctctc cttcaggata ggacgtaat tgccatcaat   960
caggacccct tgggcaagca agggtaccag cttagacagg gagacaactt tgaagtgtgg  1020
gaacgacctc tctcaggctt agcctgggct gtagctatga taaaccggca ggagattggt  1080
ggacctcgct cttataccat cgcagttgct tccctgggta aaggagtggc ctgtaatcct  1140
gcctgcttca tcacacagct cctccctgtg aaaaggaagc tagggttcta tgaatggact  1200
tcaaggttaa gaagtcacat aaatcccaca ggcactgttt tgcttcagct agaaaataca  1260
atgcagatgt cattaaaaga cttactt                                      1287
```

<210> SEQ ID NO 2
<211> LENGTH: 429
<212> TYPE: PRT
<213> ORGANISM: Homo sapiens

<400> SEQUENCE: 2

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
```

```
                20              25              30
Asp Asn Gly Leu Ala Arg Thr Pro Thr Met Gly Trp Leu His Trp Glu
            35                  40                  45
Arg Phe Met Cys Asn Leu Asp Cys Gln Glu Pro Asp Ser Cys Ile
50                  55                  60
Ser Glu Lys Leu Phe Met Glu Met Ala Glu Leu Met Val Ser Glu Gly
65                  70                  75                  80
Trp Lys Asp Ala Gly Tyr Glu Tyr Leu Cys Ile Asp Asp Cys Trp Met
                85                  90                  95
Ala Pro Gln Arg Asp Ser Glu Gly Arg Leu Gln Ala Asp Pro Gln Arg
            100                 105                 110
Phe Pro His Gly Ile Arg Gln Leu Ala Asn Tyr Val His Ser Lys Gly
        115                 120                 125
Leu Lys Leu Gly Ile Tyr Ala Asp Val Gly Asn Lys Thr Cys Ala Gly
        130                 135                 140
Phe Pro Gly Ser Phe Gly Tyr Tyr Asp Ile Asp Ala Gln Thr Phe Ala
145                 150                 155                 160
Asp Trp Gly Val Asp Leu Leu Lys Phe Asp Gly Cys Tyr Cys Asp Ser
                165                 170                 175
Leu Glu Asn Leu Ala Asp Gly Tyr Lys His Met Ser Leu Ala Leu Asn
            180                 185                 190
Arg Thr Gly Arg Ser Ile Val Tyr Ser Cys Glu Trp Pro Leu Tyr Met
        195                 200                 205
Trp Pro Phe Gln Lys Pro Asn Tyr Thr Glu Ile Arg Gln Tyr Cys Asn
        210                 215                 220
His Trp Arg Asn Phe Ala Asp Ile Asp Asp Ser Trp Lys Ser Ile Lys
225                 230                 235                 240
Ser Ile Leu Asp Trp Thr Ser Phe Asn Gln Glu Arg Ile Val Asp Val
                245                 250                 255
Ala Gly Pro Gly Gly Trp Asn Asp Pro Asp Met Leu Val Ile Gly Asn
            260                 265                 270
Phe Gly Leu Ser Trp Asn Gln Gln Val Thr Gln Met Ala Leu Trp Ala
        275                 280                 285
Ile Met Ala Ala Pro Leu Phe Met Ser Asn Asp Leu Arg His Ile Ser
        290                 295                 300
Pro Gln Ala Lys Ala Leu Leu Gln Asp Lys Asp Val Ile Ala Ile Asn
305                 310                 315                 320
Gln Asp Pro Leu Gly Lys Gln Gly Tyr Gln Leu Arg Gln Gly Asp Asn
                325                 330                 335
Phe Glu Val Trp Glu Arg Pro Leu Ser Gly Leu Ala Trp Ala Val Ala
            340                 345                 350
Met Ile Asn Arg Gln Glu Ile Gly Gly Pro Arg Ser Tyr Thr Ile Ala
        355                 360                 365
Val Ala Ser Leu Gly Lys Gly Val Ala Cys Asn Pro Ala Cys Phe Ile
        370                 375                 380
Thr Gln Leu Leu Pro Val Lys Arg Lys Leu Gly Phe Tyr Glu Trp Thr
385                 390                 395                 400
Ser Arg Leu Arg Ser His Ile Asn Pro Thr Gly Thr Val Leu Leu Gln
                405                 410                 415
Leu Glu Asn Thr Met Gln Met Ser Leu Lys Asp Leu Leu
            420                 425

<210> SEQ ID NO 3
```

```
<211> LENGTH: 398
<212> TYPE: PRT
<213> ORGANISM: Homo Sapiens

<400> SEQUENCE: 3
```

| | | | | | | | | | | | | | | | |
|---|---|---|---|---|---|---|---|---|---|---|---|---|---|---|---|
| Leu | Asp | Asn | Gly | Leu | Ala | Arg | Thr | Pro | Thr | Met | Gly | Trp | Leu | His | Trp |
| 1 | | | | 5 | | | | | 10 | | | | | 15 | |
| Glu | Arg | Phe | Met | Cys | Asn | Leu | Asp | Cys | Gln | Glu | Glu | Pro | Asp | Ser | Cys |
| | | | 20 | | | | | 25 | | | | | 30 | | |
| Ile | Ser | Glu | Lys | Leu | Phe | Met | Glu | Met | Ala | Glu | Leu | Met | Val | Ser | Glu |
| | | | 35 | | | | 40 | | | | | 45 | | | |
| Gly | Trp | Lys | Asp | Ala | Gly | Tyr | Glu | Tyr | Leu | Cys | Ile | Asp | Asp | Cys | Trp |
| 50 | | | | | 55 | | | | | 60 | | | | | |
| Met | Ala | Pro | Gln | Arg | Asp | Ser | Glu | Gly | Arg | Leu | Gln | Ala | Asp | Pro | Gln |
| 65 | | | | 70 | | | | | 75 | | | | | 80 | |
| Arg | Phe | Pro | His | Gly | Ile | Arg | Gln | Leu | Ala | Asn | Tyr | Val | His | Ser | Lys |
| | | | | 85 | | | | | 90 | | | | | 95 | |
| Gly | Leu | Lys | Leu | Gly | Ile | Tyr | Ala | Asp | Val | Gly | Asn | Lys | Thr | Cys | Ala |
| | | | 100 | | | | | 105 | | | | | 110 | | |
| Gly | Phe | Pro | Gly | Ser | Phe | Gly | Tyr | Tyr | Asp | Ile | Asp | Ala | Gln | Thr | Phe |
| | | | 115 | | | | | 120 | | | | | 125 | | |
| Ala | Asp | Trp | Gly | Val | Asp | Leu | Leu | Lys | Phe | Asp | Gly | Cys | Tyr | Cys | Asp |
| | 130 | | | | | 135 | | | | | 140 | | | | |
| Ser | Leu | Glu | Asn | Leu | Ala | Asp | Gly | Tyr | Lys | His | Met | Ser | Leu | Ala | Leu |
| 145 | | | | | 150 | | | | | 155 | | | | | 160 |
| Asn | Arg | Thr | Gly | Arg | Ser | Ile | Val | Tyr | Ser | Cys | Glu | Trp | Pro | Leu | Tyr |
| | | | | 165 | | | | | 170 | | | | | 175 | |
| Met | Trp | Pro | Phe | Gln | Lys | Pro | Asn | Tyr | Thr | Glu | Ile | Arg | Gln | Tyr | Cys |
| | | | 180 | | | | | 185 | | | | | 190 | | |
| Asn | His | Trp | Arg | Asn | Phe | Ala | Asp | Ile | Asp | Asp | Ser | Trp | Lys | Ser | Ile |
| | | | 195 | | | | | 200 | | | | | 205 | | |
| Lys | Ser | Ile | Leu | Asp | Trp | Thr | Ser | Phe | Asn | Gln | Glu | Arg | Ile | Val | Asp |
| | 210 | | | | | 215 | | | | | 220 | | | | |
| Val | Ala | Gly | Pro | Gly | Gly | Trp | Asn | Asp | Pro | Asp | Met | Leu | Val | Ile | Gly |
| 225 | | | | | 230 | | | | | 235 | | | | | 240 |
| Asn | Phe | Gly | Leu | Ser | Trp | Asn | Gln | Gln | Val | Thr | Gln | Met | Ala | Leu | Trp |
| | | | | 245 | | | | | 250 | | | | | 255 | |
| Ala | Ile | Met | Ala | Ala | Pro | Leu | Phe | Met | Ser | Asn | Asp | Leu | Arg | His | Ile |
| | | | 260 | | | | | 265 | | | | | 270 | | |
| Ser | Pro | Gln | Ala | Lys | Ala | Leu | Leu | Gln | Asp | Lys | Asp | Val | Ile | Ala | Ile |
| | | | 275 | | | | | 280 | | | | | 285 | | |
| Asn | Gln | Asp | Pro | Leu | Gly | Lys | Gln | Gly | Tyr | Gln | Leu | Arg | Gln | Gly | Asp |
| | 290 | | | | | 295 | | | | | 300 | | | | |
| Asn | Phe | Glu | Val | Trp | Glu | Arg | Pro | Leu | Ser | Gly | Leu | Ala | Trp | Ala | Val |
| 305 | | | | | 310 | | | | | 315 | | | | | 320 |
| Ala | Met | Ile | Asn | Arg | Gln | Glu | Ile | Gly | Gly | Pro | Arg | Ser | Tyr | Thr | Ile |
| | | | | 325 | | | | | 330 | | | | | 335 | |
| Ala | Val | Ala | Ser | Leu | Gly | Lys | Gly | Val | Ala | Cys | Asn | Pro | Ala | Cys | Phe |
| | | | 340 | | | | | 345 | | | | | 350 | | |
| Ile | Thr | Gln | Leu | Leu | Pro | Val | Lys | Arg | Lys | Leu | Gly | Phe | Tyr | Glu | Trp |
| | | | | 355 | | | | | 360 | | | | | 365 | |

```
Thr Ser Arg Leu Arg Ser His Ile Asn Pro Thr Gly Thr Val Leu Leu
    370                 375                 380

Gln Leu Glu Asn Thr Met Gln Met Ser Leu Lys Asp Leu Leu
385                 390                 395
```

RECOMBINANT GLYCOPROTEINS AND USES THEREOF

CROSS-REFERENCE TO RELATED APPLICATIONS

This application is a 371 U.S. National Application of PCT/US2014/061789, filed on Oct. 22, 2014, which claims priority to U.S. Provisional Patent Application Ser. No. 61/894,879, filed Oct. 23, 2013, and U.S. Provisional Patent Application Ser. No. 61/901,942, filed Nov. 8, 2013; the entire contents of which are herein incorporated by reference.

TECHNICAL FIELD

This application relates to the field of biotechnology, and more specifically, to the production of recombinant glycoproteins (e.g., recombinant human α-galactosidase-A) and the treatment of lysosomal storage diseases (e.g., Fabry disease) in a subject.

BACKGROUND

Lysosomal storage diseases are a group of over 40 disorders which are the result of defects in genes encoding enzymes that break down glycolipid or polysaccharide waste products within the lysosomes of cells. The enzymatic products, e.g., sugars and lipids, are then recycled into new products. Each of these disorders results from an inherited autosomal or X-linked recessive trait which affects the levels of enzymes in the lysosome. Generally, there is reduced or no biological or functional activity of these enzymes in the cells and tissues of affected individuals. A list of exemplary lysosomal storage diseases and the associated enzyme deficiencies are shown in FIG. 1 and are described in Table 1 of U.S. Pat. No. 6,066,626. In such diseases, the deficiency in enzyme function creates a progressive systemic deposition of lipid or carbohydrate substrate in the lysosomes of cells in the body, eventually causing loss of organ function and death.

Fabry Disease is a lysosomal storage disease caused by a deficiency in the lysosomal enzyme α-galactosidase-A. The deficiency of this lysosomal hydrolase results in a progressive deposition of glycosphingolipid globotriasylceramide (GL3) and related lipids in most tissues of the body. The deposits of GL3 are primarily found in the vascular endothelium. Progressive endothelial accumulation of GL3 leads to ischemia and infarction in organs, such as kidney, heart, or brain, causing excruciating pain, kidney failure, and cardiac and cerebrovascular disease. The average lifespan of a Fabry patient not treated with enzyme replacement therapy, from renal, cardiac, and/or cerebral complications from vascular disease, is 50 years for men and 70 years for women (Lidove et al., *Int. J. Clin. Pract.* 61:293-302, 2007).

Recombinant proteins for use in medical treatment are often produced by cell culture methods that include the use of a liquid medium that includes a blood product (e.g., a non-human animal serum or plasma). Contamination of pharmaceutical products containing recombinant proteins has been a problem in the biotechnology industry (Nims, *BioProcessingJ.* 10:4-10, 2011; Playsic et al., *BioProcessingJ.* 9:6-12, 2011; Playsic et al., *Dev. Biol. Stand* 99:95-109, 1999). For example, the presence of a number of different viruses in such pharmaceutical products is, in some instances, attributed to the blood product (e.g., a non-human animal serum or plasma) present in the liquid medium used to culture the cells that produce the recombinant protein. Examples of contaminants that have been found in recombinant protein production cell cultures and that are thought to be caused by the use of animal products (e.g., animal serum, animal plasma, or animal serum proteins) are described herein. The use of serum-free medium or animal product-free medium in a recombinant protein production cell culture is beneficial as the culture medium is better defined and simplified, has a reduced degree of contaminants, eliminates or reduces the risk of contamination or level of contaminants in a recombinant protein production cell culture, and results in a lower cost of producing a recombinant protein using cell culture.

SUMMARY

The present invention is based, at least in part, on the discovery that proteins (e.g., enzymes, e.g., α-galactosidase-A) with an altered (e.g., improved) glycosylation profile can be produced using the methods described herein. Accordingly, provided herein are α-galactosidase-A proteins with reduced variability in glycoforms, with reduced risk or level of contamination (e.g., reduced risk or level of viral contamination), and/or altered and improved glycosylation profiles (e.g., as compared prior manufactured enzymes for enzyme replacement therapy), pharmaceutical compositions and kits that include one or more of these α-galactosidase-A proteins (e.g., pharmaceutical compositions that have reduced variability in glycoforms and/or a reduced risk or level of contamination (e.g., reduced risk or level of viral contamination)), methods of generating a mammalian cell useful for recombinant expression of a glycoprotein (e.g., α-galactosidase-A), methods of producing a recombinant glycoprotein (e.g., α-galactosidase-A), methods of treating Fabry disease and methods of reducing the serum level of globotriaosylceramide in a subject, and methods of increasing the level of α-galactosidase-A in a lysosome in a mammalian cell (e.g., a cell in vitro or a cell in a subject). Also provided are expression vectors that include a sequence encoding α-galactosidase-A proteins.

Provided herein are recombinant human α-galactosidase-A (rhAGA) proteins having one or both of the structural features of: a percentage of total N-linked oligosaccharides that are monosialylated oligosaccharides that is between about 0.1% and about 1.5%; and a percentage of total N-linked oligosaccharides that are bis-mannose-6-phosphate oligosaccharides that is greater than about 9%. For example, the rhAGA protein of claim 1 can have the structural features of: a percentage of total N-linked oligosaccharides that are monosialylated oligosaccharides that is between about 0.1% and about 1.5%; and a percentage of total N-linked oligosaccharides that are bis-mannose-6-phosphate oligosaccharides that is greater than about 9%. In some embodiments, the rhAGA protein has a percentage of total N-linked oligosaccharides that are monosialylated oligosaccharides that is between about 0.1% and about 1.3% (e.g., between about 0.1% and about 1.0%, or between about 0.1% and about 0.7%). In some embodiments, the rhAGA protein has a percentage of total N-linked oligosaccharides that are bis-mannose-6-phosphate oligosaccharides that is greater than about 8.5% (e.g., greater than about 9.0%).

The rhAGA proteins provided herein can further have one or more of the structural features selected from the group of: a percentage of total N-linked oligosaccharides that are bisialylated fucose-containing oligosaccharides that is greater than about 13.5%; a percentage of total N-linked oligosaccharides that are trisialylated oligosaccharides of form 2 that is greater than about 2.0%; and a mole/mole ratio of sialic acid/protein that is greater than about 3.0. For example, an rhAGA protein provided herein can further have the structural features of: a percentage of total N-linked oligosaccharides that are bisialylated fucose-containing oligosaccharides that is greater than about 13.5%; a percentage of total N-linked oligosaccharides that are trisialylated oligosaccharides of form 2 that is greater than about 2.0%; and a mole/mole ratio of sialic acid/protein that is greater than about 3.0. In some embodiments, the rhAGA protein has a percentage of total N-linked oligosaccharides that are bisialylated fucose-containing oligosaccharides that is greater than about 13.8% (e.g., greater than about 14.0%). In some embodiments, the rhAGA protein has a percentage of total N-linked oligosaccharides that are trisialylated oligosaccharides of form 2 that is greater than about 4% (e.g., greater than about 6%). In some embodiments, the rhAGA protein has a mole/mole ratio of sialic acid/protein that is greater than about 3.2 (e.g., greater than about 3.4).

The rhAGA proteins provided herein can further have one or more structural features selected from the group of: a percentage of total N-linked oligosaccharides that are neutrally-charged oligosaccharides that is between about 0.1% and about 3.9%; a percentage of total N-linked oligosaccharides that are monosialylated fucose-containing oligosaccharides that is between about 0.1% and about 3.0%; a percentage of total N-linked oligosaccharides that are bisialylated oligosaccharides that is between about 0.1% and about 5.3%; a percentage of total N-linked oligosaccharides that are trisialylated oligosaccharides of form 1 that is between about 0.1% and about 9.0%; a percentage of total N-linked oligosaccharides that are mannose-6-phosphate oligosaccharides that is between about 1% and about 7.0%; a percentage of total N-linked oligosaccharides that are monophosphorylated oligosaccharides that is greater than about 14.8%; a percentage of total N-linked oligosaccharides that are tetrasialylated oligosaccharides that is greater than about 4.9%; and a percentage of total N-linked oligosaccharides that are monosialylated and monophosphorylated oligosaccharides that is greater than about 8.2%. For example, an rhAGA protein described herein can have four of more of the structural features selected from the group of: a percentage of total N-linked oligosaccharides that are neutrally-charged oligosaccharides that is between about 0.1% and about 3.9%; a percentage of total N-linked oligosaccharides that are monosialylated fucose-containing oligosaccharides that is between about 0.1% and about 3.0%; a percentage of total N-linked oligosaccharides that are bisialylated oligosaccharides that is between about 0.1% and about 5.3%; a percentage of total N-linked oligosaccharides that are trisialylated oligosaccharides of form 1 that is between about 0.1% and about 9.0%; a percentage of total N-linked oligosaccharides that are mannose-6-phosphate oligosaccharides that is between about 1% and about 7.0%; a percentage of total N-linked oligosaccharides that are monophosphorylated oligosaccharides that is greater than about 14.8%; a percentage of total N-linked oligosaccharides that are tetrasialylated oligosaccharides that is greater than about 4.9%; and a percentage of total N-linked oligosaccharides that are monosialylated and monophosphorylated oligosaccharides that is greater than about 8.2%. In some embodiments, the rhAGA protein has a percentage of total N-linked oligosaccharides that are neutrally-charged oligosaccharides that is between about 0.1% and about 3.0% (e.g., between about 0.1% and about 2.0%). In some embodiments, the rhAGA protein has a percentage of total N-linked oligosaccharides that are monosialylated fucose-containing oligosaccharides that is between about 1.0% and about 2.0% (e.g., between about 1.5% and about 2.0%). In some embodiments, the rhAGA protein has a percentage of total N-linked oligosaccharides that are bisialylated oligosaccharides that is between about 3.0% and about 5.0% (e.g., between about 4.0% and about 5.0%). In some embodiments, the rhAGA protein has a percentage of total N-linked oligosaccharides that are trisialylated oligosaccharides of form 1 that is between about 0.5% and about 8.0% (e.g., between about 0.5% and about 5.0%). In some embodiments, the rhAGA protein has a percentage of total N-linked oligosaccharides that are mannose-6-phosphate oligosaccharides that is between about 4% and about 6.9% (e.g., between about 5% and about 6.8%). In some embodiments, the rhAGA protein has a percentage of total N-linked oligosaccharides that are monophosphorylated oligosaccharides that is greater than about 15% (e.g., greater than about 16%). In some embodiments, the rhAGA protein has a percentage of total N-linked oligosaccharides that are tetrasialylated oligosaccharides that is greater than about 6%. In some embodiments, the rhAGA protein has a percentage of total N-linked oligosaccharides that are monosialylated and monophosphorylated oligosaccharides that is greater than about 8.5% (e.g., greater than about 9.0%).

The rhAGA proteins provided herein can have one or both of the following properties: (i) increased endocytosis by a mammalian cell expressing mannose-6-phosphate receptor protein as compared to Fabrazyme®; and (ii) increased affinity to mannose-6-phosphate receptor protein as compared to a Fabrazyme®. For example, the rhAGA proteins provided herein can have (i) increased endocytosis by a mammalian cell expressing mannose-6-phosphate receptor protein as compared to Fabrazyme®; and (ii) increased affinity to mannose-6-phosphate receptor protein as compared to Fabrazyme®. Any of the rhAGA proteins provided herein can have no detectable level or no protein, lipid, carbohydrate, nucleic acid, and contaminant (e.g., any of the contaminants described herein) present in an animal product (e.g., an animal serum, an animal plasma, or an animal blood product).

Any of the rhAGA proteins provided herein can be a rhAGA protein produced in a cell culture that used only culture media selected from the group of a protein-free, serum-free, and chemically-defined medium. Any of the rhAGA proteins provided herein can be a rhAGA protein produced in a cell culture that used only protein-free and/or chemically-defined medium. Any of the rhAGA proteins provided herein can be a rhAGA protein produced in a cell culture that used only culture media selected from the group consisting of a protein-free, serum-free, and chemically-defined medium and isolated using an integrated and continuous process. In some embodiments, the integrated and continuous process includes the steps of: (a) providing a liquid culture medium including a rhAGA protein provided herein, that is substantially free of cells, where the liquid culture medium is fed into a first multi-chromatography system (MCCS1); (b) capturing the rhAGA protein in the liquid medium using the MCCS1, where the eluate of the MCCS1 containing the recombinant therapeutic protein is continuously fed into a second multi-column chromatography system (MCCS2); and (c) purifying and polishing the recombinant therapeutic protein using the MCCS2, where the eluate from the MCCS2 is a rhAGA drug substance, and where the process is integrated and runs continuously from the liquid culture medium to the eluate from the MCCS2 that is the rhAGA drug substance. In some embodiments, the MCCS1 and/or the MCCS2 performs two different unit operations. In some embodiments, the use of MCCS1 or MCCS2, or both, involves column switching. In some embodiments, the MCCS1 performs the unit operations of capturing the recombinant protein and inactivating viruses. In some embodiments, the MCCS2 performs the unit operations of purifying and polishing the recombinant therapeutic protein. In some embodiments, the MCCS1 and/or the MCCS2 utilizes at least two chromatography columns. In some embodiments, the MCCS1 is a first periodic counter current chromatography system (PCCS1), e.g., a PCCS1 that includes a four-column PCCS. In some embodiments, three of the four columns in the four-column PCCS (in an embodiment of PCCS1) perform the unit of capturing the recombinant therapeutic protein from the liquid culture medium. In some embodiments, the eluate containing the rhAGA protein provided herein from the three of the four columns in the four-column PCC1 (in an embodiment of PCCS1) is fed into the fourth column of the four-column PCCS. In some embodiments, the fourth column of the four-column PCCS (in an embodiment of PCCS1) performs the unit operation of inactivating viruses by holding the eluate containing recombinant therapeutic protein at low pH for viral inactivation. In some embodiments, the comprises adjusting the pH of the eluate from the fourth column of the four-column PCCS using an in-line buffer adjustment reservoir before the eluate from the fourth column of the four-column PCCS is fed into the PCCS2. In some embodiments, the PCCS2 comprises three chromatography columns and a chromatographic membrane. In some embodiments, the three chromatography columns in the PCCS2 perform the unit operation of purifying the rhAGA provided herein from the eluate of the PCCS1 through cation or anion exchange chromatography. In some embodiments, the eluate from the three chromatography columns in the PCCS2 is fed into the chromatographic membrane in the PCCS2. In some embodiments, the chromatographic membrane in the PCCS2 performs the unit operation of polishing the rhAGA protein provided herein in the eluate from the three chromatography columns in the PCCS2 through cation or anion exchange chromatography. In some embodiments, the chromatographic membrane in the PCCS2 performs the unit operation of polishing through cation exchange. In some embodiments, the flow through and wash of the chromatographic membrane in PCCS2 is the rhAGA drug substance.

Also provided are pharmaceutical compositions containing any of the rhAGA protein described herein, and a pharmaceutically acceptable carrier. For example, the pharmaceutical composition can be formulated for intravenous, intraarterial, intramuscular, intradermal, subcutaneous, or intraperitoneal administration. In some embodiments, the pharmaceutical composition contains a concentration of rhAGA of about 4 mg/mL to about 6 mg/mL (e.g., about 5 mg/mL). In some examples, the pharmaceutical composition is a sterile, lyophilized powder. In some embodiments, the pharmaceutically acceptable carrier can be one or more agents selected from the group of:

mannitol, sodium phosphate monobasic, monohydrate, sodium phosphate dibasic, and heptahydrate.

Any of the pharmaceutical compositions provided herein can have no detectable level or no protein, lipid, carbohydrate, nucleic acid, and contaminant (e.g., any of the contaminants described herein) present in an animal product (e.g., an animal serum, an animal plasma, or an animal blood product).

Any of the pharmaceutical compositions provided herein can include a rhAGA protein provided herein that is produced in a cell culture that used only culture media selected from the group of a protein-free, serum-free, and chemically-defined medium.

Any of the pharmaceutical compositions provided herein can include a rhAGA protein provided herein that is produced in a cell culture that only used protein-free culture medium and/or chemically-defined culture medium. Any of the pharmaceutical compositions provided herein can include a rhAGA protein provided herein that is produced by a cell culture that used only culture media selected from the group of a protein-free, serum-free, and chemically-defined culture medium, and isolated using an integrated and continuous process (e.g., using any of the exemplary integrated and continuous processes described herein).

Also provided are expression vectors containing: a sequence that encodes recombinant human α-galactosidase-A protein; a promoter sequence operably linked to a 5' end of the sequence encoding human α-galactosidase-A protein; a sequence encoding a peptide of human CD52 protein with a TTG start codon operably linked to the 5' end of the sequence encoding human α-galactosidase-A protein; and a sequence encoding a poly(A) recognition site operably linked to a 3' end of the sequence encoding human α-galactosidase-A protein. In some embodiments, the promoter sequence is selected from the group of: hamster rpS21 promoter, hamster β-actin promoter, and SV40 early promoter; and the sequence encoding the poly(A) recognition site is a SV40 early poly(A) recognition sequence. In some embodiments, the expression vector further contains a sequence encoding a human or dog glutamine synthetase, or a dihydrofolate reductase. In some embodiments, a 5' end of the sequence encoding the human or dog glutamine synthetase is operably linked to a SV40 early promoter and a 3' end of the sequence encoding the human or dog glutamine synthetase, or the dihydrofolate reductase is operably linked to a SV40 early intron and poly(A) signal sequence.

Also provided are methods of generating a mammalian cell line useful for recombinant expression of a glycoprotein that include: (a) providing a serum-dependent immortalized mammalian cell line; (b) sequentially culturing the mammalian cell line in: (1) a cell culture medium containing a first concentration (1×) of animal serum for about 5 days to about 10 days; (2) a cell culture medium containing about a 0.2× to about a 0.3× concentration of animal serum for about 5 days to about 10 days; and (3) a cell culture medium containing about 0.01× to about 0.08× of animal serum for about 5 days to about 10 days; (c) generating single-cell subclone cultures from the culture after (b); (d) selecting a subclone of (c) that has acceptable transfection efficiency, cell growth in serum-free culture medium, and recombinant protein expression; (d) culturing the selected subclone of (d) in a protein-free, serum-free, chemically-defined medium for about 5 days to about 30 days (e.g., about 5 days to about 25 days, about 5 days to about 20 days, about 5 days to about 15 days, or about 5 days to about 10 days); (e) generating single-cell subclone cultures from the culture after (d); and (f) selecting a subclone of (e) that has acceptable transfection efficiency, peak cell density, growth properties, volumetric productivity rate (VPR), and glycosylation profile for a glycoprotein, where the selected subclone of (f) is useful for recombinant expression of a glycoprotein. Also provided are methods of generating a mammalian cell line useful for recombinant expression of a glycoprotein that include: (a) providing a serum-dependent immortalized mammalian cell line; (b) sequentially culturing the mammalian cell line in: (1) a cell culture medium comprising a first concentration (1×) of animal serum for about 1 day to about 10 days (e.g., about 3 days); (2) a cell culture medium comprising about 0.2× to about 0.6× concentration (e.g., 0.5×) of animal serum for about 1 day to about 10 days (e.g., about 3 days); and (3) a cell culture medium comprising 0× to about 0.10× of animal serum for about 5 days to about 10 days (e.g., about 8 days); (c) generating single-cell subclone cultures from the culture after (b); (d) selecting a subclone of (c) that has acceptable transfection efficiency, cell growth in serum-free culture medium, and recombinant protein expression; (e) generating single-cell subclone cultures from the selected subclone of (d); and (f) selecting a subclone of (e) that has acceptable transfection efficiency, peak cell density, growth properties, volumetric productivity rate (VPR), and recombinant protein expression, where the selected subclone of (f) is useful for recombinant expression of a glycoprotein.

In some examples, the serum-dependent immortalized mammalian cell line is a Chinese Hamster Ovary cell line. In some embodiments, the serum-dependent immortalized mammalian cell line does not endogenously express dihydrofolate reductase. In some embodiments, the selected subclone of (f) grows in suspension. In some embodiments, the recombinant protein expression is the expression of one of both of an antibody and an enzyme (e.g., human α-galactosidase-A protein). Also provided are mammalian cells useful for recombinant expression of a glycoprotein produced by any of the methods provided herein.

Also provided are methods of producing a recombinant glycoprotein that include: providing a mammalian cell useful for recombinant expression of a glycoprotein produced by any of the methods provided herein; introducing into the cell an expression vector containing a sequence encoding a glycoprotein; culturing the cell in a serum-free growth culture medium under conditions sufficient to produce the glycoprotein; and harvesting the glycoprotein from the cell or the growth culture medium. In some examples, the culturing is performed using suspension cell culture. In some embodiments, the culturing is performed using a bioreactor. In some embodiments, the culturing is performed using a protein-free, serum-free, chemically-defined medium (e.g., culturing a Chinese Hamster Ovary (CHO) cell using a protein-free, serum-free, chemically-defined medium). In some embodiments, the CHO cell does not endogenously express dihydrofolate reductase. In some embodiments, the recombinant glycoprotein is an enzyme (e.g., human α-galactosidase-A protein). In some embodiments, the sequence encoding the glycoprotein is at least 90% identical to SEQ ID NO: 1. In some embodiments, the expression vector further contains: a promoter sequence operably linked to a 5' end of the sequence encoding the glycoprotein; a sequence encoding a peptide of human CD52 protein with a TTG start codon operably linked to the 5' end of the sequence encoding the glycoprotein; and a sequence encoding a poly(A) recognition site operably linked to a 3' end of the sequence encoding the glycoprotein. In some embodiments, the promoter sequence is selected from the group consisting of: hamster rpS21 promoter, hamster β-actin promoter, and SV40 early promoter; and the sequence encoding the poly(A) recognition site is a SV40 early poly(A) recognition sequence. In some embodiments, expression vector further comprises a sequence encoding a human or dog glutamine synthetase, or a dihydrofolate reductase. In some embodiments, a 5' end of the sequence encoding the human or dog glutamine synthetase, or the dihydrofolate reductase, is operably linked to a SV40 early promoter and a 3' end of the sequence encoding the human or dog glutamine synthetase, or the dihydrofolate reductase is operably linked to a SV40 early intron and poly(A) signal sequence. In some examples, the glycoprotein is harvested from the cell. In some examples, the glycoprotein is harvested from the cell culture medium. Also provided are recombinant glycoproteins (e.g., recombinant human α-galactosidase-A protein) produced by any of the methods provided herein. Also provided are pharmaceutical compositions containing a recombinant glycoprotein produced by any of the methods provided herein, and a pharmaceutically acceptable carrier. For example, the pharmaceutical composition can be formulated for intravenous, intraarterial, intramuscular, intradermal, subcutaneous, or intraperitoneal administration. In some embodiments, the glycoprotein is recombinant human α-galactosidase-A protein and the pharmaceutical composition contains a concentration of about 4 mg/mL to about 6 mg/mL (e.g., about 5 mg/mL) recombinant human α-galactosidase-A protein. In some embodiments, the pharmaceutical composition is a sterile, lyophilized powder.

Also provided are methods of treating Fabry disease in a subject that include administering to a subject having Fabry disease a therapeutically effective amount of any of the recombinant human α-galactosidase-A (rhAGA) proteins provided herein. In some embodiments, the administering is systemic administration (e.g., intravenous administration). In some embodiments, the subject is administered the rhAGA in a dose of about 0.5 mg/kg body weight to about 2.0 mg/kg body weight (e.g., about 1.0 mg/kg body weight). In some embodiments, the subject is administered two or more doses of the rhAGA protein. For example, the at least of the two or more doses of the rhAGA protein can be administered about two weeks apart. Some embodiments further include administering to the subject one or more additional therapeutic agents selected from the group of: analgesics, anticoagulants, acetylcholinesterase inhibitors, β-blockers, and glucosylcermide synthase inhibitors. In some embodiments, the subject is a human subject. In some embodiments, the subject has been diagnosed as having Fabry disease.

Also provided are methods of increasing the level of α-galactosidase-A protein in a lysosome in a mammalian cell that include contacting a mammalian cell with an effective amount of any of the recombinant human α-galactosidase-A (rhAGA) proteins provided herein. In some embodiments, the cell is in vitro (e.g., an in vitro human cell). In some embodiments, the cell is in a subject (e.g., a human). In some embodiments, the subject has been diagnosed as having Fabry disease. In some examples, the contacting is performed by systemically administering the rhAGA to the subject. For example, the systemic administration can be intravenous administration. In some embodiments, the subject is administered the rhAGA in a dose of about 0.5 mg/kg body weight to about 2.0 mg/kg body weight (e.g., about 1.0 mg/kg body weight). In some embodiments, the subject is administered two or more doses of the rhAGA protein. For example, at least two of the two or more doses of the rhAGA protein can be administered about two weeks apart.

Also provided are methods of reducing the level of globotriaosylceramide in the serum of a subject that include administering to a subject in need thereof a therapeutically effective amount of any of the recombinant human α-galactosidase-A (rhAGA) proteins provided herein. In some embodiments, the subject has a serum level of globotriasoylceramde of greater than 8 μg/mL. In some examples, the subject has been diagnosed as having Fabry disease. In some embodiments, the administering is systemic administration (e.g., intravenous administration). In some embodiments, the subject is administered the rhAGA in a dose of about 0.5 mg/kg body weight to about 2.0 mg/kg body weight (e.g., about 1.0 mg/kg body weight). In some embodiments, the subject can be administered two or more doses of the rhAGA protein. For example, at least two of the two or more doses of the rhAGA protein can be administered about two weeks apart. Some embodiments further include administering to the subject one or more additional therapeutic agents selected from the group of: analgesics, anticoagulants, acetylcholinesterase inhibitors, β-blockers, and glucosylcermide synthase inhibitors. In some embodiments, the subject is a human.

By the term "isolated" is meant a molecule that is separated from at least one contaminant (e.g., protein, nucleic acid, lipid, or carbohydrate, or combination thereof). In non-limiting examples, an isolated α-galactosidase-A protein or other glycoprotein is at least 80%, 85%, 90%, 91%, 92%, 93%, 94%, 95%, 96%, 97%, 98%, or 99% pure by weight.

The term "liquid culture medium" means a fluid that includes sufficient nutrients to allow a mammalian cell to grow or proliferate in vitro. For example, a liquid culture medium can include one or more of: amino acids (e.g., 20 amino acids), a purine (e.g., hypoxanthine), a pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some embodiments, a liquid culture medium can include serum from a mammal. In some embodiments, a liquid culture medium does not include serum or another extract from a mammal (a defined liquid culture medium). In some embodiments, a liquid culture medium can include trace metals, a mammalian growth hormone, and/or a mammalian growth factor. Another example of liquid culture medium is minimal medium (e.g., a medium that includes only inorganic salts, a carbon source, and water). Non-limiting examples of liquid culture medium are described herein. Additional examples of liquid culture medium are known in the art and are commercially available. A liquid culture medium may include any density of mammalian cells. For example, as used herein, a volume of liquid culture medium removed from a bioreactor can be substantially free of mammalian cells.

The term "serum-free liquid culture medium" means a liquid culture medium that does not include a mammalian serum.

The term "serum-containing liquid culture medium" means a liquid culture medium that includes a mammalian serum.

The term "chemically-defined liquid culture medium" is a term of art and means a liquid culture medium in which all of the chemical components are known. For example, a chemically-defined liquid culture medium does not include fetal bovine serum, bovine serum albumin, or human serum albumin, as these preparations typically include a complex mix of albumins and lipids.

The term "protein-free liquid culture medium" means a liquid culture medium that does not include any protein (e.g., any detectable protein).

The term "integrated process" means a process performed using structural elements that function cooperatively to achieve a specific result (e.g., the generation of a therapeutic protein drug substance (e.g., that includes recombinant human α-galactosidase-A protein) from a liquid culture medium).

The term "continuous process" means a process which continuously feeds fluid through at least a part of a system for producing a drug substance (e.g., a drug substance containing a recombinant protein) from a culture medium containing the recombinant protein (e.g., any of the recombinant proteins described herein). For example, a liquid culture medium that includes a recombinant therapeutic protein (e.g., recombinant human α-galactosidase-A protein) is continuously fed into the system while it is in operation and a therapeutic protein drug substance is fed out of the system. Non-limiting examples of such systems that can be used to perform a continuous process are described in U.S. Provisional Patent Application Nos. 61/856,930 and 61/775,060.

The term "multi-column chromatography system" or "MCCS" means a system of a two or more interconnected or switching chromatography columns and/or chromatographic membranes. One exemplary multi-column chromatography system is a periodic counter current chromatography system (PCC) that includes two or more interconnected or switching chromatography columns and/or chromatographic membranes. Additional examples of multi-column chromatography systems are known in the art.

The term "secreted protein" or "secreted recombinant protein" is well known in the art and means a protein (e.g., a recombinant protein) that is secreted at least partially from a mammalian cell into at least the extracellular space (e.g., out into a liquid culture medium). Skilled practitioners will appreciate that a "secreted" protein need not dissociate entirely from the cell to be considered a secreted protein.

The term "perfusion culturing" means culturing a plurality of cells (e.g., mammalian cells) in a first liquid culture medium, wherein the culturing includes periodic or continuous removal of the first liquid culture medium and at the same time or shortly after adding substantially the same volume of a second liquid culture medium to a container (e.g., a bioreactor). In some examples, there is an incremental change (e.g., increase or decrease) in the volume of the first liquid culture medium removed and added over incremental periods (e.g., an about 24-hour period, a period of between about 1 minute and about 24-hours, or a period of greater than 24 hours) during the culturing period (e.g., the culture medium refeed rate on a daily basis). The fraction of media removed and replaced each day can vary depending on the particular cells being cultured, the initial seeding density, and the cell density at a particular time. "RV" or "reactor volume" means the volume of the culture medium present at the beginning of the culturing process (e.g., the total volume of the culture medium present after seeding). Bioreactors that can be used to perform perfusion culturing are known in the art. Skill practitioners will appreciate that a bioreactor can be adapted to be used in perfusion culturing (e.g., adapted to be a perfusion bioreactor).

The term "fed-batch culturing" is a term of art and means culturing a plurality of cells (e.g., mammalian cells) in a first liquid culture medium, wherein the culturing of the cells present in a container (e.g., a bioreactor) includes the periodic or continuous addition of a second liquid culture medium to the first liquid culture medium without substantial or significant removal of the first liquid culture medium or second liquid culture medium from the cell culture. The second liquid culture medium can be the same as the first liquid culture medium. In some examples of fed-batch culture, the second liquid culture medium is a concentrated form of the first liquid culture medium. In some examples of fed-batch culture, the second liquid culture medium is added as a dry powder. Skilled practitioners will appreciate that a bioreactor can be adapted to be used in fed-batch culturing (e.g., adapted to be a fed-batch bioreactor).

"Specific productivity rate" or "SPR" is a term of art and as used herein refers to the mass or enzymatic activity of a recombinant therapeutic protein produced per mammalian cell per day. The SPR for a recombinant therapeutic antibody is usually measured as mass/cell/day. The SPR for a recombinant therapeutic enzyme is usually measured as units/cell/day or (units/mass)/cell/day.

"Volume productivity rate" or "VPR" is a term of art and as used herein refers to the mass or enzymatic activity of recombinant therapeutic protein produced per volume of culture (e.g., per L of bioreactor, vessel, or tube volume) per day. The VPR for a recombinant therapeutic antibody is usually measured as mass/L/day. The VPR for a recombinant therapeutic enzyme is usually measured as units/L/day or mass/L/day.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is list of lysosomal storage diseases and the corresponding enzymatic defect for each disease.

FIG. 2 is a cDNA sequence encoding precursor human α-galactosidase-A protein and the amino acid sequence of precursor human α-galactosidase-A protein (SEQ ID NOS: 1 and 2, respectively), and the amino acid sequence of mature human α-galactosidase-A protein (SEQ ID NO: 3).

FIG. 32A is graph showing the percent of Fabrazyme® (FZ) and recombinant human α-galactosidase-A protein provided herein (FZ2G) present in peaks 1-5 of ciIEF.

FIG. 32B is graph showing the percent of Fabrazyme® (FZ) and recombinant human α-galactosidase-A protein provided herein (FZ2G) present in peaks 6-11 of ciIEF.

FIG. 32C is graph showing the percent of Fabrazyme® (FZ) and recombinant human α-galactosidase-A protein provided herein (FZ2G) present in peaks 12-14 of ciIEF.

DETAILED DESCRIPTION

Figure 3:
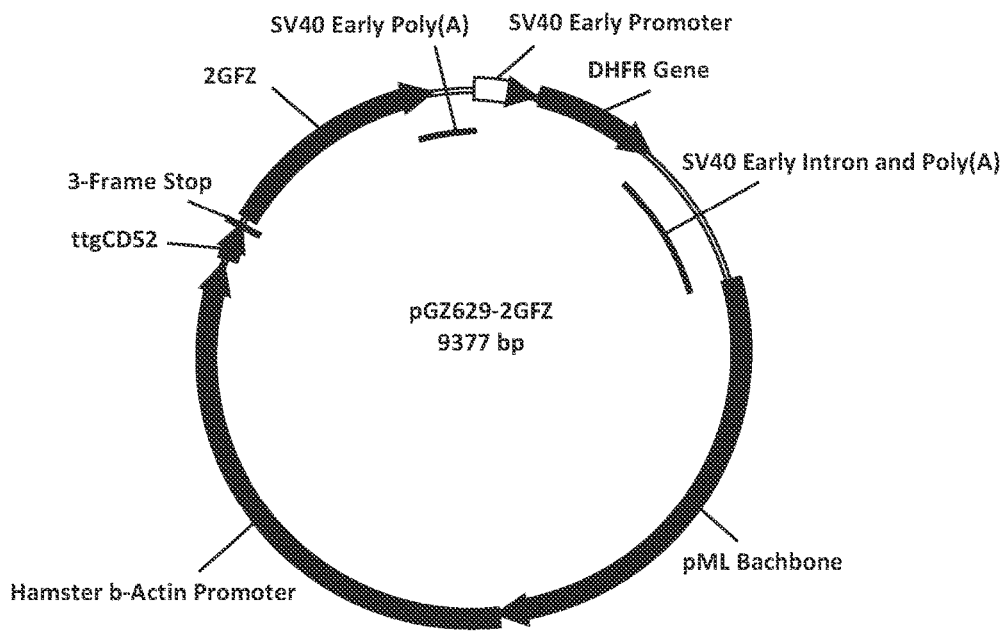
FIG. 3 is a map of the pGZ629-2GFZ vector that includes a cDNA sequence encoding recombinant human α-galactosidase-A protein (2GFZ).

Provided herein are recombinant human α-galactosidase-A protein having an altered glycosylation profile as compared to Fabrazyme®, and compositions, pharmaceutical compositions, and kits containing at least one of the recombinant human α-galactosidase-A proteins. The presently provided recombinant glycoproteins and compositions containing the presently provided recombinant glycoproteins have, e.g., the following benefits: less variability in glycoforms and/or lower risk or level of contamination (e.g., lower risk or level of viral contamination). The presently provided recombinant glycoproteins may also have one or more of the following non-limiting advantages: decreased non-specific targeting to the liver (by binding to the asialoglycoprotein receptor expressed on the surface of hepatocytes following administration of the recombinant glycoprotein to a subject, e.g., a human subject), increased rate of endocytosis of the recombinant glycoprotein by a mammalian cell (e.g., a human cell) expressing mannose-6-phosphate receptor protein on its surface, increased affinity to mannose-6-phosphate receptor protein, increased serum half-life, and decreased effective dose, in any combination, as compared to Fabrazyme®. Also provided are methods of generating a mammalian cell useful for recombinant expression of a recombinant glycoprotein (e.g., human α-galactosidase-A protein) and methods of producing a recombinant glycoprotein (e.g., human α-galactosidase-A protein). Also provided are methods of treating Fabry disease, methods of reducing the level of globotriaosylcermaide in the serum of a subject, and methods of increasing the level of α-galactosidase-A in a lyososome in a mammalian cell (e.g., a cell in vitro or a cell in a subject). Also provided are expression vectors that include a sequence encoding human α-galactosidase-A protein.

Alpha-Galactosidase-A

Human α-galactosidase-A (α-D-galactoside galactohydrolase; α-gal A; EC 3.2.1.22) is a lysosomal exoglycosidase encoded by a gene on Xq22. Mature human α-galactosidase-A is a homodimer composed of two non-covalently linked subunits of 398 amino acids (approximately 51 kD), each of which includes an active site and possible three N-linked glycosylations sites (N139, N192, and N215). The active site of α-galactosidase-A protein has two aspartic acid residues (D170 and D231) that are critical for catalytic activity. The three-dimensional crystal structure of α-galactosidase-A protein was published in 1996 (Munier-Lehmann et al., *J. Biol. Chem.* 271:15166-15174, 1996). Alpha-galactosidase-A catalyzes the hydrolysis of globotriaosylceramide (GL-3) and other α-galactyl-terminated neutral glycosphingolipids, such as galabiosylceramide and Blood Group B substances to ceramide dihexoside and galactose. The specific activity of a recombinant form of α-galactosidase-A can be tested using a synthetic substrate, e.g., p-nitrophenyl-α-D-galactopyranoside (pNP).

The glycosylation of human α-galactosidase-A protein allows for its targeting to the lysosome in human cells. A brief summary of the cellular pathways used to glycosylate human α-galactosidase-A protein and other human glycoproteins is provided below.

Human α-galactosidase-A protein is synthesized in endoplasmic reticulum. After synthesis, each monomer of human α-galactosidase-A protein undergoes post-translation modification in the Golgi apparatus. As noted above, each monomer of human α-galactosidase-A protein has three possible N-glycosylation sites (N139, N192, and N215). There are several physiological glycoforms of human α-galactosidase-A protein. The N139 residue links complex carbohydrates, whereas the N192 and N215 residues link oligosaccharides rich in mannose and are therefore, involved in targeting the enzyme for uptake by the lysosome. After synthesis in the endoplasmic reticulum, the precursors of lysosomal enzymes are transferred to the Golgi apparatus. The post-translational modifications and, in particular, the addition of mannose-6-phosphate (M6P) residues, occur in the cis-Golgi. The M6P-enzyme complex binds to the M6P receptor and is released from the trans-Golgi network, from where it is transported to the prelysosomal/endosomal compartments. Once within the endosome compartment, the acidic pH causes the enzyme to dissociate from its receptor. It then undergoes dephosphorylation to produce the mature and functional enzyme. The receptor is then recycled to the trans-Golgi to recruit other enzymes, or moves to the plasma membrane where it can collect endogenous enzyme (Sly et al., J. Cell Biochem. 18:67-85, 1982; Helenius et al., Ann. Rev. Biochem. 32:1-100, 1997).

The biosynthesis of all eukaryotic N-glycans begins on the cytoplasmic face of the endoplasmic reticulum (ER) membrane with the transfer of GlcNAc-P from UDP-GlcNAc to the lipid-like precursor dolichol phosphate (Dol-P) to generate dolichol pyrophosphate N-acetylglucosamine (Dol-P-P-GlcNAc). Fourteen sugars are sequentially added to Dol-P to yield a glycan of Glc3Man9GlcNAc2 before transfer of the entire glycan to an asparagine in the sequence of Asn-X-Ser/Thr in a protein in the ER by the protein oligosaccaryltransferase. The protein-bound N-glycan is subsequently remodeled in the ER and Golgi apparatus by a complex series of reactions catalyzed by membrane-bound glycosidases and glycosyltransferases. Following the covalent attachment of the 14-sugar oligomannose glycan to Asn-X-Ser/Thr, a series of reactions are used to remove three sugars from the Glc3Man9GlcNAc2 in the ER. These trimming steps are conserved among all eukaryotes. Trimming of Glc3Man9GlcNAc2 begins with the sequential removal of glucose residues by α-glycosidases I and II. Both glucosidases function in the lumen of the ER, with α-glycosidase I acting on the terminal α1-2Glc and α-glucosidase II sequentially removing the two inner α1-3Glc residues.

Before exiting the ER, many glycoproteins are acted on by ER α-mannosidase I, which specifically removes the terminal α1-2Man from the central arm of Man9GlcNAc2 to yield a Man8GlcNAc2 isomer. The majority of glycoproteins exiting the ER en route to the Golgi apparatus have N-glycans with eight or nine mannose residues (depending on whether they have been acted on by ER α-mannosidase I). For most glycoproteins, additional mannose residues are removed in the cis compartment of the Golgi apparatus until Man5GlcNAc2 is generated.

The biosynthesis of hybrid and complex N-glycans is initiated in the medial Golgi apparatus by the action of an N-acetylglucosaminyltransferase called GlcNAcT-1. GlcNAcT-1 adds an N-acetyl-glucosamine residue to C-2 of the mannose α1-3 in the core of Man5GlcNAc2, which initiates the first branch of an N-glycan. Once this step has occurred, the majority of N-glycans are trimmed by α-mannosidase II, which removes the terminal α1-3Man and the α1-6Man residues from GlcNAcMan5GlcNAc2 to form GlcNAcMan3GlcNAc2. Once the two mannose residues are removed, a second N-acetylglucosamine is added to C-2 of the mannose α1-6 by GlcNAcT-II to yield the precursor for all biantennary, complex N-glycans. The resulting glycan has two antennae or branches that were initiated by the addition of two terminal N-acetylglucosamine residues. Additional branches can be initiated at C-4 of the core mannose α1-3 (by GlcNAcT-IV) and C-6 of the core mannose α1-6 (by GlcNAcT-V) to yield tri- and tetra-tennary N-glycans. Another enzyme, termed GlyNAcT-IX or GlcNAcT-Vb, catalyzes the same reaction as GlcNAcT-V on the C-6 core mannose α1-6, but in contrast to GlcNAcT-V, GlnNAcT-IX/Vb can also transfer N-acetylglucosamine to C-6 of the core mannose α1-3. Another branch can be initiated at C-4 of the core mannose α1-3 by GlcNAcT-VI.

Complex and hybrid N-glycans may carry a bisecting N-acetylglucosamine residue that is attached to the β-mannose of the core by GlcNAcT-III. Bi-, tri-, and tetra-antennary complex N-glycans with a bisecting N-acetylglucosmaine are synthesized when GlcNAcT-III acts after α-mannosidase II and the initiation of branches by GlcNAcT-II, GlcNAcT-IV, and GlcNAcT-V.

Further sugar additions, mostly occurring in the trans Golgi apparatus convert the hybrid and branched N-glycans into an extensive array of mature, complex N-glycans. Sugars can be added to the core, branching N-acetylglucosamine residues can be elongated by sugar additions, and elongated branches can be capped or decorated. For example, the product of GlcNAcT-II is a biantennary N-glycan that can be extended by the addition of fucose, galactose, and sialic acid to generate a complex N-glycan with two branches. Complex N-glycans can, e.g., have many additional sugars, including those attached to the core of the N-glycan, additional branches, branches extended with poly-N-acetyllactosamine units, and different capping structures. Complex type oligosaccharides are synthesized in the Golgi apparatus from mannose-3 containing oligosaccharides, e.g., by the addition of N-acetylglycosamine, galactose, and sialic acid residues.

The core modification is often an addition of a fucose in an α1-6 linkage to the N-acetylglucosamine adjacent to the asparagine in the core of the glycan. The fucosyltransferases involved in transferring fucose to this core N-acetylglucosamine require the prior action of GlcNAcT-1. The majority of complex and hybrid N-glycans have elongated branches that are made by the addition of a β-linked galactose residue to the initiating N-acetylglucosamine to produce the ubiquitous building block Galβ1-4GlcNAc, referred to as a type 2 N-acetyllactosamine. Antennae can be further elongated by the sequential addition of N-acetylglucosamine and galactose residues, resulting in tandem repeats of LacNAc (−3Galβ1-4GlcNAcβ1-)n, termed poly-N-acetyllactosamine. In another example, β-linked galactose is added to the C-3 of the N-acetylglucosamine to yield Galβ1-3GlcNAc, referred to as a type-1 N-acetyllactosamine sequence. In some proteins, β-linked N-acetylgalactosamine is added to N-acetylglucosamine instead of β-linked galactose, yielding antennae with a GalNAcβ1-4GlcNAc extension. Capping or decorating reactions involve the addition of sialic acid, fucose, galactose, N-acetylgalactosamine, and sulfate to the branches. Capping sugars are most commonly α-linked and therefore extend away from the β-linked ribbon-like poly-N-acetyllactosamine branches.

Lysosomal enzymes can acquire a GlcNAc-1-P at C-6 of mannose residues on oligomannose N-glycans in the cis Golgi apparatus. The N-acetyl-glucosamine is then removed in the trans Golgi apparatus by a glycosidase, thereby exposing Man-6-P residues that are recognized by Man-6-P receptor and routed to the acidified, prelysosomal compartment.

Hybrid type oligosaccharides are synthesized in the Golgi from mannose-3 and mannose-5 core structures by the addition of, e.g., N-acetylglycosamine, galactose, and sialic acid residues. Hybrid N-glycans are formed if the GlcNAcMan5GlcNAc2 glycan is not acted on by α-mannosidase II, leaving the peripheral α1-3Man and α1-6Man residues intact and unmodified in the mature glycoprotein. Incomplete action of α-mannosidase II can result in GlcNAcMan4GlcNAc2 hybrids. Another Golgi apparatus mannosidase, α-mannosidase IIX, also acts on the GlnNAcMan5GlcNAc2 generated by GlcNAcT-1.

A detailed review of the biosynthetic pathways and enzymes used to generate N-linked glycans (e.g., high mannose type oligosaccharides) are described in Stanley et al., "N-Glycans" in Essentials of Glycobiology, Ed. Varki, Cummings, and Eskho, Cold Spring Harbor Press, 2009. As noted above, the post-translational glycosylation of recombinant human α-galactosidase-A is important for proper trafficking of the protein. For example, substitution of the serine residue at amino acid position 215 results in impairment of enzyme trafficking to the lysosome (Munier-Lehmann et al., J. Biol. Chem. 271:15166-15174, 1996; Wildt et al., Nat. Rev. Microbiol. 3:119-128, 2005). A study describing the different glycoforms of human α-galactosidase-A protein expressed in a CHO cell is described in Matsuura et al., Glycobiology 8:329-339, 1998.

Exemplary precursor and mature sequences of human α-galactosidase-A protein are shown in FIG. 2, respectively (SEQ ID NOs: 1 and 2, respectively). A recombinant human α-galactosidase protein, as described herein, can include a sequence that is at least 95% identical (e.g., at least 96%, 97%, 98%, 99%, or 100% identical) to SEQ ID NO: 1 or 2. A recombinant human α-galactosidase-A protein can have (e.g., consist of) a sequence that is at least 95% identical (e.g., at least 96%, 97%, 98%, 99%, or 100% identical) to SEQ ID NO: 1 or 2. In other examples, a recombinant human α-galactosidase-A protein can include a sequence of SEQ ID NO: 2 with 1 to 30 amino acids (e.g., 1 to 25 amino acids, 1 to 20 amino acids, 1 to 15 amino acids, 1 to 10 amino acids, 1 to 5 amino acids, 1 to 3 amino acids, 1 or 2 amino acids, 20 to 25 amino acids, 15 to 25 amino acids, 10 to 25 amino acids, 1 to 10 amino acids, 1 to 8 amino acids, and 5 to 15 amino acids) removed from the N-terminus and/or 1 to 30 amino acids removed from the C-terminus (e.g., 1 to 25 amino acids, 1 to 20 amino acids, 1 to 15 amino acids, 1 to 10 amino acids, 1 to 5 amino acids, 1 to 3 amino acids, 1 or 2 amino acids, 20 to 25 amino acids, 15 to 25 amino acids, 10 to 25 amino acids, 1 to 10 amino acids, 1 to 8 amino acids, and 5 to 15 amino acids).

A recombinant human α-galactosidase-A protein can be covalently bonded to a heterologous amino acid sequence or tag. Non-limiting examples of a heterologous amino acid sequence that can be bonded to a recombinant human α-galactosidase protein include: a poly-His tag, chitin-binding protein, maltose-binding protein, glutathione-S-transferase, and streptavidin. Any type of tag can be covalently bonded to the human α-galactosidase-A protein (e.g., a fluorescent group, a radionucleotide, and a fluorescent protein). Additional examples of molecules that can be covalently bonded to a human α-galactosidase-A protein include a polymer, e.g., a polyethylene glycol, a polyvinyl, a polyester, a polylactide, a polyglycolide, a polycaprolactone, and copolymers thereof.

Exemplary precursor and mature sequences of human α-galactosidase-A protein are shown in FIG. 2, respectively (SEQ ID NOs: 1 and 2, respectively). A recombinant human α-galactosidase protein, as described herein, can include a sequence that is at least 95% identical (e.g., at least 96%, 97%, 98%, 99%, or 100% identical) to SEQ ID NO: 1 or 2. A recombinant human α-galactosidase-A protein can have (e.g., consist of) a sequence that is at least 95% identical (e.g., at least 96%, 97%, 98%, 99%, or 100% identical) to SEQ ID NO: 1 or 2. In other examples, a recombinant human α-galactosidase-A protein can include a sequence of SEQ ID NO: 2 with 1 to 30 amino acids (e.g., 1 to 25 amino acids, 1 to 20 amino acids, 1 to 15 amino acids, 1 to 10 amino acids, 1 to 5 amino acids, 1 to 3 amino acids, 1 or 2 amino acids, 20 to 25 amino acids, 15 to 25 amino acids, 10 to 25 amino acids, 1 to 10 amino acids, 1 to 8 amino acids, and 5 to 15 amino acids) removed from the N-terminus and/or 1 to 30 amino acids removed from the C-terminus (e.g., 1 to 25 amino acids, 1 to 20 amino acids, 1 to 15 amino acids, 1 to 10 amino acids, 1 to 5 amino acids, 1 to 3 amino acids, 1 or 2 amino acids, 20 to 25 amino acids, 15 to 25 amino acids, 10 to 25 amino acids, 1 to 10 amino acids, 1 to 8 amino acids, and 5 to 15 amino acids).

A recombinant human α-galactosidase-A protein can be covalently bonded to a heterologous amino acid sequence or tag. Non-limiting examples of a heterologous amino acid sequence that can be bonded to a recombinant human α-galactosidase protein include: a poly-His tag, chitin-binding protein, maltose-binding protein, glutathione-S-transferase, and streptavidin. Any type of tag can be covalently bonded to the human α-galactosidase-A protein (e.g., a fluorescent group, a radionucleotide, and a fluorescent protein). Additional examples of molecules that can be covalently bonded to a human α-galactosidase-A protein include a polymer, e.g., a polyethylene glycol, a polyvinyl, a polyester, a polylactide, a polyglycolide, a polycaprolactone, and copolymers thereof.

An exemplary nucleic acid (e.g., cDNA) encoding human α-galactosidase-A protein is shown in FIG. 2 (SEQ ID NO: 1).

In some examples, any of the nucleic acids (e.g., cDNAs) described herein can be covalently bonded to one of more of a fluorescent tag and a quencher. In other examples, any of the nucleic acids (e.g., cDNAs) can include or further include at least one nucleotide that includes a radioisotope (e.g., $P^{32}$, $P^{33}$, and/or $S^{35}$).

Altered Glycoforms of α-Galactosidase-A Protein

The present specification provides recombinant human α-galactosidase-A proteins (FZ2G) that have altered (e.g., improved) glycosylation as compared to Fabrayzme®. The recombinant human α-galactosidase-A proteins provided herein have, for example, an increased percentage of total N-linked oligosaccharides that are bis-mannose-6-phosphate oligosaccharides (as compared to Fabrazyme®) that results in increased binding to the mannose-6-phosphate receptor, which in turn can increase the rate of endocytosis of the recombinant protein by a mammalian cell (e.g., a human cell) expressing mannose-6-phosphate receptor protein on its surface (as compared to Fabrazyme®). The recombinant human α-galactosidase A proteins provided herein can also have one or both of a decreased percentage of total N-linked oligosaccharides that are monosialylated oligosaccharides and an increased percentage of total N-linked oligosaccharides that are tetrasialylated oligosaccharides as compared to Fabrazyme®, which can result in a decrease in the non-specific targeting of recombinant protein to the liver (by binding to the asialoglycoprotein receptor expressed on the surface of hepatocytes following administration of the recombinant human α-galactosidase-A protein to a subject, e.g., a human subject) and increased serum half-life, respectively, as compared to Fabrazyme®.

The recombinant human α-galactosidase A protein provided herein also, e.g., shows less variability in its composition (e.g., less variability in glycoforms) and/or is a safer product (e.g., reduced risk or level of contamination with one or more of bacteriophages, bacteria, mycobacteria, and viruses (e.g., enteroviruses (e.g., human or animal enteroviruses), rhinoviruses (e.g., animal or human rhinoviruses), animal or human picobirnaviruses, kobuviruses, infectious bovine rhinotracheitis, bovine viral diarhhoea virus, bovine reovirus-3, caliciviridae, echovirus, polioviruses, rotaviruses (e.g., animal or human rotavirus), bovine spumaviruses, porcine endogenous retrovirus, bovine immunodeficiency virus, hepatitis viruses, vesiviruses (e.g., vesivirus 2117), noroviruses (e.g., animal or human noroviruses), astroviruses (e.g., human or animal astroviruses), animal or human parainfluenza or metapneumoviruses, anelloviruses, coronaviruses, phleboviruses, bovine schmallenberg virus, calicivirus, cycloviruses, circoviruses (e.g., porcine or bovine circovirus), cosaviruses, coxsackievirus, kubavirus, pestivirus, polyoma viruses (e.g., bovine polyoma virus), bovine papillomavirus, new rodent papilloma type 2 SV40, parvoviruses (e.g., porcine, rodent, human, or bovine parvovirus), cardioviruses (e.g., EMCV), paramyxoviruses, vesicular stomatitis virus, gyroviruses, cosavirus, Seneca valley virus, coronavirus, equine infectious anemia, human adenovirus, feline calicivirus, adenovirus type 2, bovine adenovirus type 3, pseudorabies virus, bovine viral diarrhea, parainfluenza type 3, infectious bovine rhinotracheitis, bluetongue virus, feline leukemia virus, minute virus of mice, bovine parvovirus, cache valley virus, reovirus (e.g., animal or human reovirus), canine adenovirus, SV-40 virus, encephalomyocarditis virus, porice PRRSV, bovine herpes virus 4, or foot and mouth disease)).

Fabrazyme® was previously shown to have a significantly different glycosylation pattern compared to Replagal® (Lee et al., Glycobiology 13:305-313, 2003). The notable differences in the glycosylation pattern of Fabrazyme® and Replagal® are thought to be due, in part, to the different cell lines used to produce these proteins (e.g., Fabrazyme® is produced by a CHO cell line and Replagal® is produced by a human cell line).

Fabrazyme® is a recombinant form of human α-galactosidase-A protein produced and sold by Genzyme. Fabrazyme® and methods of making Fabrazyme® are described, e.g., in U.S. Pat. No. 5,356,804. Replagal® is a recombinant form of human α-galactosidase-A protein produced and sold by Shire. Replagal® and methods of making Replagal® are described, e.g., in U.S. Pat. Nos. 6,083,725; 6,458,574; 6,395,884; and 7,133,354.

The recombinant human α-galactosidase proteins provided herein (FZ2G) have two or more (e.g., 3, 4, 5, 6, 7, 8, 9, 10, 11, or 12) of any of the structural features (e.g., in any combination) (i) through (xii) listed below. Any of the ranges of the values listed below for each of the one or more parameters from (i) through (xii) can be present in a recombinant human α-galactosidase-A protein provided herein. In addition, any of the recombinant human α-galactosidase proteins provided herein can have one or more (e.g., one, two, or three) of the exemplary functional properties described in this section. Any combination of the physical characteristics and/or functional properties of the recombinant human α-galactosidase-A proteins described herein can be combined in any manner. Exemplary combinations of the structural features of the recombinant human α-galactosidase-A proteins provided herein are described below.

In addition, the recombinant human α-galactosidase-A protein provided herein (FZ2G) can have less variability in structure (e.g., less variability in glycoforms) and/or a reduced risk or level of contamination (e.g., a reduced risk or level of contamination).

Any of the rhAGA proteins provided herein can have no detectable level or no protein, lipid, carbohydrate, nucleic acid, and contaminant (e.g., any of the contaminants described herein) present in an animal product (e.g., an animal serum, an animal plasma, or an animal blood product). Any of the rhAGA proteins provided herein can be a rhAGA protein produced in a cell culture that used only culture media selected from the group of a protein-free, serum-free, and chemically-defined medium. Any of the rhAGA proteins provided herein can be a rhAGA protein produced in a cell culture that used only protein-free and/or chemically-defined medium. Any of the rhAGA proteins provided herein can be a rhAGA protein produced in a cell culture that used only culture media selected from the group consisting of a protein-free, serum-free, and chemically-defined medium and isolated using an integrated and continuous process (e.g., any of the integrated and continuous processes described herein or in WO 14/137903). Any of the rhAGA proteins provided herein can be a rhAGA protein having an improved safety profile (e.g., reduced risk of contamination (e.g., any of the exemplary contaminants described herein or known in the art), as compared to a rhAGA protein provided herein that is produced by a method that includes the use of a culture medium containing an animal product (e.g., animal serum, animal plasma, or an animal blood factor or protein).

Biophysical Properties

I. N-Linked Monosialylated Oligosaccharides

The recombinant human α-galactosidase-A proteins described herein can have a decreased percentage of total N-linked oligosaccharides that are monosialylated oligosaccharides as compared to Fabrazyme®. The recombinant human α-galactosidase-A proteins described herein can have about the same or a slightly decreased percentage of total N-linked oligosaccharides that are monosialylated fucose-containing oligosaccharides as compared to Fabrazyme®. This feature is advantageous as monosialylated oligosaccharides may contain exposed galactose residues that bind to the asialoglycoprotein receptor expressed on hepatocytes in the liver. The liver is not a target tissue for recombinant human α-galactosidase-A protein and thus, a decrease in the amount of monosialylated oligosaccharides is thought to decrease the non-productive targeting of this enzyme in the human body.

Fabrazyme® has a percentage of total N-linked oligosaccharides that are monosialylated oligosaccharides (e.g., peak 3 in anthranilic acid labeled N-linked oligosaccharide profiles) between about 1.7% to about 3.2%. The recombinant human α-galactosidase-A proteins provided herein (FZ2G) can have a percentage of total N-linked oligosaccharides that are monosialylated oligosaccharides (e.g., peak 3 in anthranilic acid labeled N-linked oligosaccharide profiles) between about 0.1% and about 1.6% (e.g., between about 0.1% and about 1.5%, between about 0.1% and about 1.4%, between about 0.1% and about 1.3%, between about 0.1% and about 1.2%, between about 0.1% and about 1.1%, between about 0.1% and about 1.0%, between about 0.1% and about 0.9%, between about 0.1% and about 0.8%, between about 0.1% and about 0.7%, between about 0.1% and about 0.6%, between about 0.1% and about 0.5%, between about 0.1% and about 0.4%, between about 0.2% and about 1.4%, between about 0.2% and about 1.3%, between about 0.2% and about 1.2%, between about 0.2% and about 1.0%, between about 0.2% and about 0.9%, between about 0.2% and about 0.8%, between about 0.2% and about 0.7%, between about 0.3% and about 1.4%, between about 0.3% and about 1.3%, between about 0.3% and about 1.3%, between about 0.3% and about 1.2%, between about 0.3% and about 1.2%, between about 0.3% and about 1.1%, between about 0.3% and about 1.0%, between about 0.3% and about 0.9%, between about 0.3% and about 0.8%, between about 0.3% and about 0.7%, between about 0.4% and about 1.4%, between about 0.4% and about 1.3%, between about 0.4% and about 1.2%, between about 0.4% and about 1.1%, between about 0.4% and about 1.0%, between about 0.4% and about 0.9%, between about 0.4% and about 0.8%, between about 0.4% and about 0.7%, between about 0.5% and about 1.4%, between about 0.5% and about 1.3%, between about 0.5% and about 1.2%, between about 0.5% and about 1.1%, between about 0.5% and about 1.0%, between about 0.5% and about 0.9%, or between about 0.6% and about 1.2%).

Fabrazyme® has a percentage of total N-linked oligosaccharides that are monosialylated fucose-containing oligosaccharides (e.g., peak 2 in anthranilic acid labeled N-linked oligosaccharide profiles) between about 2.0% and about 5.7%. The recombinant human α-galactosidase-A proteins provided herein (FZ2G) can have a percentage of total N-linked oligosaccharides that are monosialylated fucose-containing oligosaccharides (e.g., peak 2 in anthranilic acid labeled N-linked oligosaccharide profiling) between about 0.1% and 3.0% (e.g., between about 0.1% and about 2.9%, between about 0.1% and about 2.8%, between about 0.1% and about 2.7%, between about 0.1% and about 2.6%, between about 0.1% and about 2.5%, between about 0.1% and about 2.4%, between about 0.1% and about 2.3%, between about 0.1% and about 2.2%, between about 0.1% and about 2.1%, between about 0.1% and about 2.0%, between about 0.1% and about 1.9%, between about 0.1% and about 1.8%, between about 0.1% and about 1.7%, between about 0.1% and about 1.6%, between about 0.1% and about 1.5%, between about 0.1% and about 1.4%, between about 0.1% and about 1.3%, between about 0.1% and about 1.2%, between about 0.3% and about 3.0%, between about 0.3% and about 2.9%, between about 0.3% and about 2.8%, between about 0.3% and about 2.7%, between about 0.3% and about 2.6%, between about 0.3% and about 2.5%, between about 0.3% and about 2.4%, between about 0.3% and about 2.3%, between about 0.3% and about 2.2%, between about 0.3% and about 2.1%, between about 0.3% and about 2.0, between about 0.3% and about 1.9%, between about 0.3% and about 1.8%, between about 0.3% and about 1.7%, between about 0.3% and about 1.6%, between about 0.3% and about 1.5%, between about 0.3% and about 1.4%, between about 0.3% and about 1.3%, or between about 0.3% and about 1.2%).

Exemplary methods for determining the percentage of total N-linked oligosaccharides that are monosialylated oligosaccharides or monosialylated fucose-containing oligosaccharides are described in the Examples. Additional methods are known in the art.

II. N-Linked Bis-Mannose-6-Phosphate Oligosaccharides

The recombinant human α-galactosidase-A proteins provided herein can have an increased percentage of total N-linked oligosaccharides that are bis-mannose-6-phosphate oligosaccharides (e.g., peak 11 in anthranilic acid labeled N-linked oligosaccharide profiling) as compared to Fabrazyme®. An increased level of bis-mannose-6-phosphate oligosaccharides results in increased targeting to cells that express a mannose-6-phosphate receptor on its plasma membrane. The binding to the mannose-6-phosphate receptor triggers endocytosis of the enzyme into the cell and shuttling of the enzyme to a cell lysosome.

Fabrazyme® has a percentage of total N-linked oligosaccharides that are bis-mannose-6-phosphate oligosaccharides (e.g., peak 11 in anthranilic acid labeled N-linked oligosaccharide profiles) between about 4.0% and about 7.0%. For example, a recombinant human α-galactosidase-A protein provided herein (FZ2G) can have a percentage of total N-linked oligosaccharides that are bis-mannose-6-phosphate oligosaccharides (e.g., peak 11 in anthranilic acid labeled N-linked oligosaccharide profiling) that is greater than about 7.5% (e.g., greater than about 7.6%, greater than about 7.7%, greater than about 7.8%, greater than about 7.9%, greater than about 8.0%, greater than about 8.1%, greater than about 8.2%, greater than about 8.2%, greater than about 8.3%, greater than about 8.4%, greater than about 8.5%, greater than about 8.6%, greater than about 8.7%, greater than about 8.8%, greater than about 8.9%, greater than about 8.9%, greater than about 9.0%, greater than about 9.1%, greater than about 9.2%, greater than about 9.3%, greater than about 9.4%, greater than about 9.5%, greater than about 9.6%, greater than about 9.7%, greater than about 9.8%, greater than about 9.9%, greater than about 10.0%, greater than about 10.1%, greater than about 10.2%, greater than about 10.3%, greater than about 10.4%, greater than about 10.5%, greater than about 10.6%, greater than about 10.7%, greater than about 10.8%, greater than about 10.9%, or greater than about 11%). For example, a recombinant human α-galactosidase-A protein provided herein (FZ2G) can have a percentage of total N-linked oligosaccharides that are bis-mannose-6-phosphate oligosaccharides (e.g., peak 11 in anthranilic acid labeled N-linked oligosaccharide profiling) that is between about 7.0% and about 13%, between about 8.0% and about 12.0%, or between about 9.0% and about 11.0%.

Exemplary methods for determining the percentage of total N-linked oligosaccharides that are bis-mannose-6-phosphate oligosaccharides are described in the Examples. Additional methods are known in the art.

III. N-Linked Bisialylated and N-Linked Bisialylated Fucose-Containing Oligosaccharides The recombinant human α-galactosidase-A proteins provided herein can have about the same or an increased percentage of total N-linked oligosaccharides that are bisialylated fucose-containing oligosaccharides (e.g., peak 4 in anthranilic acid labeled N-linked oligosaccharide profiling) as compared to Fabrazyme®. Recombinant human α-galactosidase-A proteins provided can have a decreased percentage of total N-linked oligosaccharides that are bisialylated oligosaccharides (e.g., peak 5 in anthranilic acid labeled N-linked oligosaccharide profiling) as compared to Fabrazyme®. An increased level of bisialylated fucose-containing oligosaccharides is thought to increase the half-life of the protein in vivo and/or in vitro (e.g., in serum in a subject or in a pharmaceutical composition).

Fabrazyme® has a percentage of total N-linked oligosaccharides that are bisialylated fucose-containing oligosaccharides (e.g., peak 4 in anthranilic acid labeled N-linked oligosaccharide profiling) between about 11.0% and about 14.2%. For example, a recombinant human α-galactosidase-A protein provided herein (FZ2G) can have a percentage of total N-linked oligosaccharides that are bisialylated fucose-containing oligosaccharides (e.g., peak 4 in anthranilic acid labeled N-linked oligosaccharide profiling) that is greater than about 13.0% (e.g., greater than about 13.1%, greater than about 13.2%, greater than about 13.3%, greater than about 13.4%, greater than about 13.5%, greater than about 13.6%, greater than about 13.7%, greater than about 13.8%, greater than about 13.9%, greater than about 14.0%, greater than about 14.1%, greater than about 14.2%, greater than about 14.3%, greater than about 14.4%, greater than about 14.5%, greater than about 14.6%, greater than about 14.7%, greater than about 14.8%, greater than about 14.9%, or greater than 15.0%). For example, a recombinant human α-galactosidase-A protein provided herein (FZ2G) can have a percentage of total N-linked oligosaccharides that are bisialylated fucose-containing oligosaccharides (e.g., peak 4 in anthranilic acid labeled N-linked oligosaccharide profiling) of between about 13.0% to about 15.0%, between about 13.5% to about 15.5%, between about 14.0% to about 16.0%, or between about 14.5% and about 16.5%.

Fabrazyme® has a percentage of total N-linked oligosaccharides that are bisialylated oligosaccharides (e.g., peak 5 in anthranilic acid labeled N-linked oligosaccharide profiling) between about 5.6% and about 7.1%. The recombinant human α-galactosidase-A proteins provided herein can have a percentage of total N-linked oligosaccharides that are bisialylated oligosaccharides (e.g., peak 5 in anthranilic acid labeled N-linked oligosaccharide profiling) between about 0.1% and about 5.3% (e.g., between about 0.1% and about 5.2%, between about 0.1% and about 5.1%, between about 0.1% and about 5.0%, between about 0.1% and about 4.9%, between about 0.1% and about 4.8%, between about 0.1% and about 4.7%, between about 0.1% and about 4.6%, between about 0.1% and about 4.5%, between about 0.1% and about 4.4%, between about 0.1% and about 4.3%, between about 0.1% and about 4.2%, between about 0.1% and about 4.1%, between about 0.1% and about 4.0%, between about 0.1% and about 3.9%, between about 0.1% and about 3.8%, about 0.1% and about 3.7%, between about 0.1% and about 3.6%, between about 0.1% and about 3.5%, between about 0.1% and about 3.4%, between about 0.1% and about 3.3%, between about 0.1% and about 3.2%, between about 0.1% and about 3.1%, between about 0.1% and about 3.0%, between about 0.1% and about 2.9%, between about 0.1% and about 2.8%, between about 0.1% and about 2.7%, between about 0.1% and about 2.6%, between about 0.1% and about 2.5%, between about 0.3% and about 5.2%, between about 0.3% and about 5.1%, between about 0.3% and about 5.0%, between about 0.3% and about 4.9%, between about 0.3% and about 4.8%, between about 0.3% and about 4.7%, between about 0.3% and about 4.6%, between about 0.3% and about 4.5%, between about 0.3% and about 4.4%, between about 0.3% and about 4.3%, between about 0.3% and about 4.2%, between about 0.3% and about 4.1%, between about 0.3% and about 4.0%, between about 0.3% and about 3.9%, between about 0.3% and about 3.8%, between about 0.3% and about 3.7%, between about 0.3% and about 3.6%, between about 0.3% and about 3.5%, between about 0.3% and about 3.5%, between about 0.3% and about 3.4%, between about 0.3% and about 3.3%, between about 0.3% and about 3.2%, between about 0.3% and about 3.1%, between about 0.3% and about 3.0%, between about 0.3% and about 2.9%, between about 0.3% and about 2.8%, between about 0.3% and about 2.7%, between about 0.3% and about 2.6%, or between about 0.3% and about 2.5%).

Exemplary methods for determining the percentage of total N-linked oligosaccharides that are bisialylated and bisialylated fucose-containing oligosaccharides are described in the Examples. Additional are known in the art.

IV N-Linked Trisialylated Oligosaccharides

Figure 10:
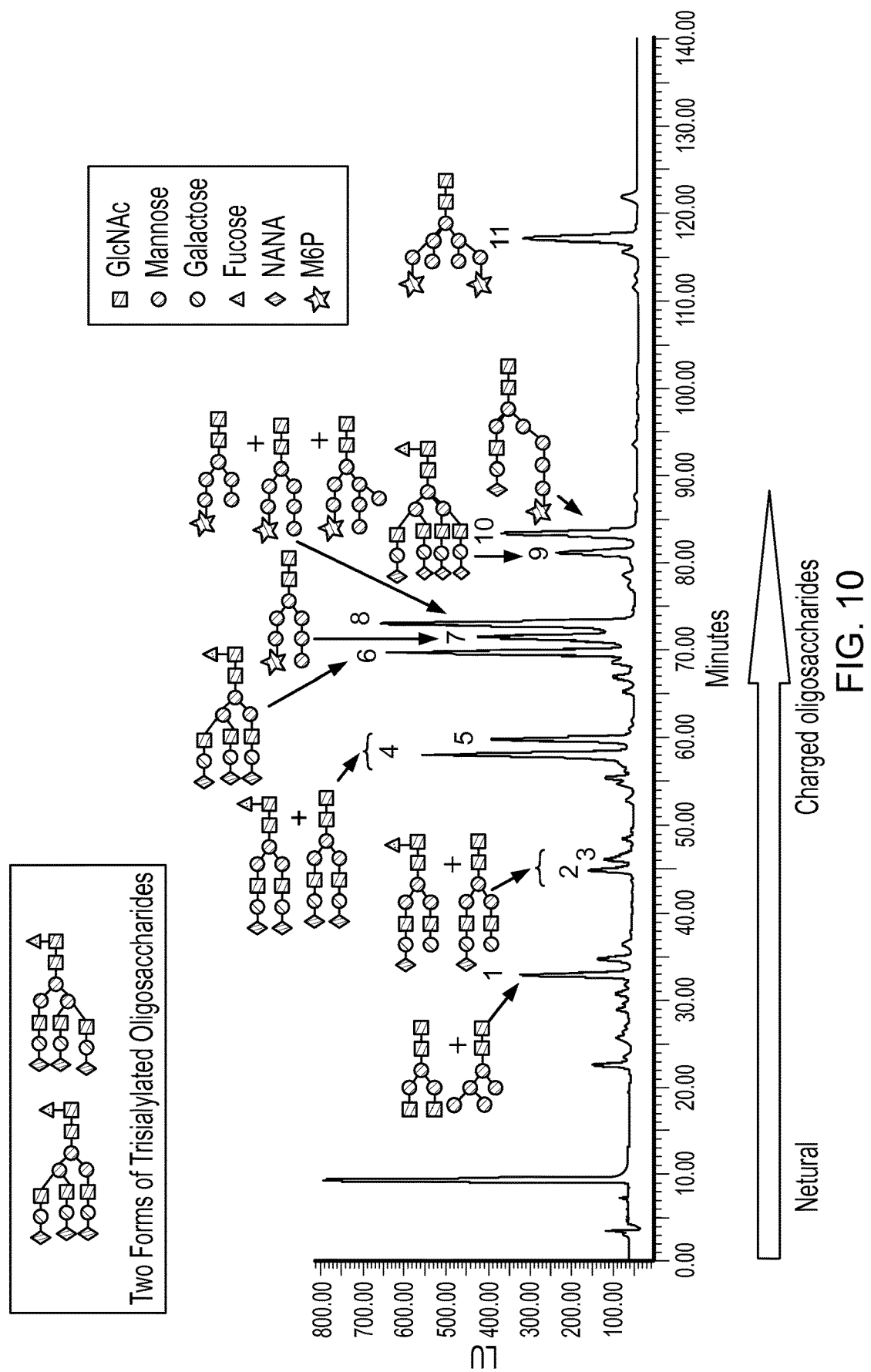
FIG. 10 is an exemplary chromatographic elution profile of N-linked oligosaccharides derivatized with 2-anthranilic acid (AA-labeled) showing the N-linked oligosaccharide(s) structures corresponding to each peak. The inset shows two triantennary, trisialylated oligosaccharide structures, where one of the two structures corresponds to peak 6 (form 1) and the other of the two structures corresponds to peak 6' (form 2) in the chromatographic elution profile of N-linked oligosaccharides derivatized with 2-AA.

Recombinant human α-galactosidase-A proteins provided herein can have an increased percentage of total N-linked oligosaccharides that are triantennary, trisialylated oligosaccharides of form 2 (i.e., peak 6' in anthranilic acid labeled N-linked oligosaccharide profiling) as compared to Fabrazyme®. The recombinant human α-galactosidase-A proteins provided herein can have a reduced percentage of total N-linked oligosaccharides that are triantennary, trisialylated oligosaccharides of form 1 (e.g., peak 6 in anthranilic acid labeled N-linked oligosaccharide profiling) as compared to Fabrazyme®. The inset of FIG. 10 shows two triantennary, trisialylated oligosaccharide structures, where one of the two structures corresponds to peak 6 (form 1) and the other of the two structures corresponds to peak 6' (form 2) in the chromatographic elution profile of N-linked oligosaccharides derivatized with 2-AA. An increased level of trisialylated fucose-containing oligosaccharides is thought to increase the half-life of the protein in vivo and/or in vitro (e.g., in serum in a subject or in a pharmaceutical composition).

Fabrazyme® has a percentage of total N-linked oligosaccharides that are triantennary trisialylated oligosaccharides of form 2 (e.g., peak 6' in anthranilic acid labeled N-linked oligosaccharide profiling) between about 0.5% and about 1.2%. For example, a recombinant human α-galactosidase-A protein provided herein (FZ2G) can have a percentage of total N-linked oligosaccharides that are triantennary, trisialylated oligosaccharides of form 2 (e.g., peak 6' in anthranilic acid labeled N-linked oligosaccharide profiling) that is greater than 2.0% (e.g., greater than 2.1%, greater than 2.2%, greater than 2.3%, greater than 2.4%, greater than 2.5%, greater than 2.6%, greater than 2.7%, greater than 2.8%, greater than 2.9%, greater than 3.0%, greater than 3.1%, greater than 3.2%, greater than 3.3%, greater than 3.4%, greater than 3.5%, greater than 3.6%, greater than 3.7%, greater than 3.8%, greater than 3.9%, greater than 4.0%, greater than 4.1%, greater than 4.2%, greater than 4.3%, greater than 4.4%, greater than 4.5%, greater than 4.6%, greater than 4.7%, greater than 4.8%, greater than 4.9%, greater than 5.0%, greater than 5.1%, greater than 5.2%, greater than 5.3%, greater than 5.4%, greater than 5.5%, greater than 5.6%, greater than 5.7%, greater than 5.8%, greater than 5.9%, greater than 6.0%, greater than 6.1%, greater than 6.2%, greater than 6.3%, greater than 6.4%, greater than 6.5%, greater than 6.7%, greater than 6.8%, greater than 6.9%, greater than 7.0%, or greater than 7.1%). For example, a recombinant human α-galactosidase-A protein provided herein (FZ2G) can have a percentage of total N-linked oligosaccharides that are triantennary, trisialylated oligosaccharides of form 2 (e.g., peak 6' in anthranilic acid labeled N-linked oligosaccharide profiling) that is between about 5.0% and about 9.0%, between about 5.5% and about 8.5%, between about 6.0% and about 8.0%, or between about 6.5% and about 7.5%.

Fabrazyme® has a percentage of total N-linked oligosaccharides that are triantennary, trisialylated oligosaccharides of form 1 (e.g., peak 6 in anthranilic acid labeled N-linked oligosaccharide profiling) between about 9.5% and about 13%. For example, a recombinant human α-galactosidase-A protein provided herein can have a percentage of total N-linked oligosaccharides that are triantennary, trisialylated oligosaccharides of form 1 (e.g., peak 6 in anthranilic acid labeled N-linked oligosaccharide profiling) that is between about 0.1% and about 9.0% (e.g., between about 0.1% and about 8.9%, between about 0.1% and about 8.8%, between about 0.1% and about 8.7%, between about 0.1% and about 8.6%, between about 0.1% and about 8.5%, between about 0.1% and about 8.4%, between about 0.1% and about 8.3%, between about 0.1% and about 8.2%, between about 0.1% and about 8.1%, between about 0.1% and about 8.0%, between about 0.1% and about 7.9%, between about 0.1% and about 7.8%, between about 0.1% and about 7.7%, between about 0.1% and about 7.6%, between about 0.1% and about 7.5%, between about 0.1% and about 7.4%, between about 0.1% and about 7.3%, between about 0.1% and about 7.2%, between about 0.1% and about 7.1%, between about 0.1% and about 7.0%, between about 0.1% and about 6.9%, between about 0.1% and about 6.8%, between about 0.1% and about 6.7%, between about 0.1% and about 6.6%, between about 0.1% and about 6.5%, between about 0.1% and about 6.4%, between about 0.1% and about 6.3%, between about 0.1% and about 6.2%, between about 0.1% and about 6.1%, between about 0.1% and about 6.0%, between about 0.1% and about 5.9%, between about 0.1% and about 5.8%, between about 0.1% and about 5.7%, between about 0.1% and about 5.6%, between about 0.1% and about 5.5%, between about 0.1% and about 5.4%, between about 0.1% and about 5.3%, between about 0.1% and about 5.2%, between about 0.1% and about 5.1%, between about 0.1% and about 5.0%, between about 0.1% and about 4.9%, between about 0.1% and about 4.8%, between about 0.1% and about 4.7%, between about 0.1% and about 4.6%, between about 0.1% and about 4.5%, between about 0.1% and about 4.4%, between about 0.1% and about 4.3%, between about 0.1% and about 4.2%, between about 0.1% and about 4.1%, between about 0.1% and about 4.0%, between about 0.1% and about 3.9%, between about 0.1% and about 3.8%, between about 0.1% and about 3.7%, between about 0.1% and about 3.6%, between about 0.1% and about 3.5%, between about 0.1% and about 3.4%, between about 0.1% and about 3.3%, between about 0.1% and about 3.2%, between about 0.1% and about 3.1%, or between about 0.1% and about 3.0%).

Exemplary methods for determining the percentage of total N-linked oligosaccharides that are trisialylated oligosaccharides are described in the Examples. Additional methods are known in the art.

V. Mole/Mole Ratio of Sialic Acid/Protein

Recombinant human α-galactosidase-A proteins provided herein can have a mole to mole ratio of sialic acid to protein that is about the same or greater than Fabrazyme®. An increased number of sialic acid molecules present in oligosaccharides is thought to increase the half-life of the protein in vitro and/or in vivo (e.g., in a pharmaceutical composition and in the serum of a mammal).

Fabrazyme® has a mole to mole ratio of sialic acid to protein of about 2.6 to about 3.3. Fabrazyme® also has a mole to mole ratio of sialic acid to mannose-6-phosphate that is greater than 1.5. For example, a recombinant human α-galactosidase-A protein provided herein (FZ2G) can have a mole/mole ratio of sialic acid to protein that is greater than 3.0 (e.g., greater than 3.1, greater than 3.2, greater than 3.3, greater than 3.4, greater than 3.5, greater than 3.6, greater than 3.7, greater than 3.8, greater than 3.9, greater than 4.0, greater than 4.1, greater than 4.2, greater than 4.3, greater than 4.4, greater than 4.5, greater than 4.6, greater than 4.7, greater than 4.8, greater than 4.9, or greater than 5.0).

Exemplary methods for determining the mole/mole ratio of sialic acid to protein are described in the Examples. Additional methods are known in the art.

VI. N-Linked Neutrally-Charged Oligosaccharides

Recombinant human α-galactosidase-A proteins provided herein can have a decreased percentage of total N-linked oligosaccharides that are neutrally-charged oligosaccharides (e.g., peak 1 in anthranilic acid labeled N-linked oligosaccharide profiling) as compared to Fabrazyme®.

Fabrazyme® has a percentage of total N-linked oligosaccharides that are N-linked neutrally-charged oligosaccharides (e.g., peak 1 in anthranilic acid labeled N-linked oligosaccharide profiling) between about 4.0% to about 7.1%. For example, a recombinant human α-galactosidase-A protein provided herein can have a percentage of total N-linked oligosaccharides that are neutrally-charged oligosaccharides (e.g., peak 1 in anthranilic acid labeled N-linked oligosaccharide profiling) that is between about 0.1% and about 3.9% (e.g., between about 0.1% and about 3.8%, between about 0.1% and about 3.7%, between about 0.1% and about 3.6%, between about 0.1% and about 3.5%, between about 0.1% and about 3.4%, between about 0.1% and about 3.3%, between about 0.1% and about 3.2%, between about 0.1% and about 3.1%, between about 0.1% and about 3.0%, between about 0.1% and about 2.9%, between about 0.1% and about 2.8%, between about 0.1% and about 2.7%, between about 0.1% and about 2.6%, between about 0.1% and about 2.5%, between about 0.1% and about 2.4%, between about 0.1% and about 2.3%, between about 0.1% and about 2.2%, between about 0.1% and about 2.1%, between about 0.1% and about 2.0%, between about 0.1% and about 1.9%, between about 0.1% and about 1.8%, between about 0.1% and about 1.7%, between about 0.1% and about 1.6%, between about 0.1% and about 1.5%, between about 0.1% and about 1.4%, between about 0.1% and about 1.3%, between about 0.1% and about 1.2%, between about 0.1% and about 1.1%, between about 0.1% and 1.0%, between about 0.3% and about 3.9%, between about 0.3% and about 3.8%, between about 0.3% and about 3.7%, between about 0.3% and about 3.6%, between about 0.3% and about 3.5%, between about 0.3% and about 3.4%, between about 0.3% and about 3.3%, between about 0.3% and about 3.2%, between about 0.3% and about 3.1%, between about 0.3% and about 3.0%, between about 0.3% and about 2.9%, between about 0.3% and about 2.8%, between about 0.3% and about 2.7%, between about 0.3% and about 2.6%, between about 0.3% and about 2.5%, between about 0.3% and about 2.4%, between about 0.3% and about 2.3%, between about 0.3% and about 2.2%, between about 0.3% and about 2.1%, between about 0.3% and about 2.0%, between about 0.3% and about 1.9%, between about 0.3% and about 1.8%, between about 0.3% and about 1.7%, between about 0.3% and about 1.6%, between about 0.3% and about 1.5%, between about 0.3% and about 1.4%, between about 0.3% and about 1.3%, between about 0.3% and about 1.2%, between about 0.3% and about 1.1%, or between about 0.3% and about 1.0%).

Exemplary methods for determining the percentage of total N-linked oligosaccharides that are neutrally-charged oligosaccharides (e.g., peak 1 in anthranilic acid labeled N-linked oligosaccharide profiling) are described in the Examples. Additional methods are known in the art.

VII. N-Linked Mannose-6-Phosphate Oligosaccharides

Recombinant human α-galactosidase-A proteins provided can have about the same or a slightly decreased percentage of total N-linked oligosaccharides that are mannose-6-phosphate oligosaccharides as compared to Fabrazyme®.

Fabrazyme® has a percentage of total N-linked oligosaccharides that are N-linked mannose-6-phosphate oligosaccharides (e.g., peak 7 in anthranilic acid labeled N-linked oligosaccharide profiling) between about 5.5% to about 10.0%. For example, a recombinant human α-galactosidase-A protein provided herein (FZ2G) can have a percentage of total N-linked oligosaccharides that are mannose-6-phosphate oligosaccharides (e.g., peak 7 in anthranilic acid labeled N-linked oligosaccharide profiling) that is between about 0.1% to about 7.0% (e.g., between about 0.1% to about 6.9%, between about 0.1% to about 6.8%, between about 0.1% to about 6.7%, between about 0.1% to about 6.6%, between about 0.1% to about 6.5%, between about 0.1% to about 6.4%, between about 0.1% to about 6.3%, between about 0.1% to about 6.2%, between about 0.1% to about 6.1%, between about 0.1% to about 6.0%, between about 0.1% to about 5.9%, between about 0.1% to about 5.8%, between about 0.1% to about 5.7%, between about 0.1% to about 5.6%, between about 0.1% to about 5.5%, between about 0.1% to about 5.4%, between about 0.1% to about 5.3%, between about 0.1% to about 5.2%, between about 0.1% to about 5.1%, or between about 0.1% to about 5.0%). For example, a recombinant human α-galactosidase-A protein provided herein (FZ2G) can have a percentage of total N-linked oligosaccharides that are mannose-6-phosphate oligosaccharides (e.g., peak 7 in anthranilic acid labeled N-linked oligosaccharide profiling) that is between about 5.0% and about 7.0%.

Exemplary methods for determining the percentage of total N-linked oligosaccharides that are mannose-6-phosphate oligosaccharides (e.g., peak 7 in anthranilic acid labeled N-linked oligosaccharide profiling) are described in the Examples. Additional methods are known in the art.

VIII. N-Linked Monophosphorylated Oligosaccharides

Recombinant human α-galactosidase-A proteins provided can have an increased percentage of total N-linked oligosaccharides that are monophosphorylated oligosaccharides as compared to Fabrazyme®.

Fabrazyme® has a percentage of total N-linked oligosaccharides that are N-linked monophosphorylated oligosaccharides (e.g., peak 8 in anthranilic acid labeled N-linked oligosaccharide profiling) between about 10.9% to about 14.7%. For example, a recombinant human α-galactosidase-A protein provided herein (FZ2G) can have a percentage of total N-linked oligosaccharides that are monophosphorylated oligosaccharides (e.g., peak 8 in anthranilic acid labeled N-linked oligosaccharide profiling) that is greater than about 14.8% (e.g., greater than about 14.9%, greater than 15.0%, greater than about 15.1%, greater than about 15.2%, greater than about 15.3%, greater than about 15.4%, greater than about 15.5%, greater than about 15.6%, greater than about 15.7%, greater than about 15.8%, greater than about 15.9%, greater than about 16.0%, greater than about 16.1%, greater than about 16.2%, greater than about 16.3% greater than about 16.4%, greater than about 16.5%, greater than about 16.6%, greater than about 16.7%, greater than about 16.8%, greater than about 16.9%, greater than about 17.0%, greater than about 17.1%, greater than about 17.2%, greater than about 17.3%, greater than about 17.4%, greater than about 17.5%, greater than about 17.6%, greater than about 17.7%, greater than about 17.8%, greater than about 17.9%, greater than about 18.0%, greater than about 18.1%, greater than about 18.2%, greater than about 18.3%, greater than about 18.4%, greater than about 18.5%, greater than about 18.6%, greater than about 18.7%, greater than about 18.8%, greater than about 18.9%, greater than about 19.0%, greater than about 19.1%, greater than about 19.2%, greater than about 19.3%, greater than about 19.4%, greater than about 19.5%, greater than about 19.6%, greater than about 19.7%, greater than about 19.8%, greater than about 19.9%, greater than about 20.0%, greater than about 20.1%, greater than about 20.2%, greater than about 20.3%, greater than about 20.4%, greater than about 20.5%, greater than about 20.6%, greater than about 20.7%, greater than about 20.8%, greater than about 20.9%, greater than about 21.0%, greater than about 21.1%, greater than about 21.2%, greater than about 21.3%, greater than about 21.4%, greater than about 21.5%, greater than about 21.6%, greater than about 21.7%, greater than about 21.8%, greater than about 21.9%, greater than about 22.0%, greater than about 22.1%, greater than about 22.2%, greater than about 22.3%, greater than about 22.4%, greater than about 22.5%, greater than about 22.6%, greater than about 22.7%, greater than about 22.8%, greater than about 22.9%, or greater than about 23.0%). For example, a recombinant human α-galactosidase-A protein provided herein (FZ2G) can have a percentage of total N-linked oligosaccharides that are monophosphorylated oligosaccharides (e.g., peak 8 in anthranilic acid labeled N-linked oligosaccharide profiling) that is between about 15.5% and about 17.5%, between about 16.0% and about 18.0%, or between about 16.5% and about 18.5%.

Exemplary methods for determining the percentage of total N-linked oligosaccharides that are monophosphorylated oligosaccharides (e.g., peak 8 in anthranilic acid labeled N-linked oligosaccharide profiling) are described in the Examples. Additional methods are known in the art.

IX. N-Linked Tetrasialylated Oligosaccharides

The recombinant human α-galactosidase-A proteins provided herein can have an increased percentage of total N-linked oligosaccharides that are tetrasialylated oligosaccharides (e.g., peak 9 in anthranilic acid labeled N-linked oligosaccharide profiling) as compared to Fabrazyme®. An increased level of tetrasialylated oligosaccharides is thought to increase the half-life of the protein in vivo and/or in vitro (e.g., in serum in a subject or in a pharmaceutical composition).

Fabrazyme® has a percentage of total N-linked oligosaccharides that are tetrasialylated oligosaccharides (e.g., peak 9 in anthranilic acid labeled N-linked oligosaccharide profiling) between about 2.3% to about 4.8%. For example, a recombinant human α-galactosidase-A protein provided herein (FZ2G) can have a percentage of total N-linked oligosaccharides that are tetrasialylated oligosaccharides (e.g., peak 9 in anthranilic acid labeled N-linked oligosaccharide profiling) that is greater than about 4.9% (e.g., greater than about 5.0%, greater than about 5.1%, greater than about 5.2%, greater than about 5.3%, greater than about 5.4%, greater than about 5.5%, greater than about 5.6%, greater than about 5.7%, greater than about 5.8%, greater than about 5.9%, greater than about 6.0%, greater than about 6.1%, greater than about 6.2%, greater than about 6.3%, greater than about 6.4%, greater than about 6.5%, greater than about 6.6%, greater than about 6.7%, greater than about 6.8%, greater than about 6.9%, greater than about 7.0%, greater than about 7.1%, greater than about 7.2%, greater than about 7.3%, greater than about 7.4%, greater than about 7.5%, greater than about 7.6%, greater than about 7.7%, greater than about 7.8%, greater than about 7.9%, or greater than about 8.0%). For example, a recombinant human α-galactosidase-A protein provided herein (FZ2G) can have a percentage of total N-linked oligosaccharides that are tetrasialylated oligosaccharides (e.g., peak 9 in anthranilic acid labeled N-linked oligosaccharide profiling) that is between about 6.0% to about 8.0%, between about 6.5% to about 8.5%, between about 6.0% and about 9.0%, or between about 7.0% and about 9.0%.

Exemplary methods for performing and determining the percentage of total N-linked oligosaccharides that are tetrasialylated oligosaccharides (e.g., peak 9 in anthranilic acid labeled N-linked oligosaccharide profiling) are described in the Examples. Additional methods are known in the art.

X. N-Linked Hybrid Structures that are Monosialylated and Monophosphorylated

Recombinant human α-galactosidase-A proteins provided can have an increased percentage of total N-linked oligosaccharides that are monosialylated, monophosphorylated, hybrid structures as compared to Fabrazyme®.

Fabrazyme® has a percentage of total N-linked oligosaccharides that are monosialylated, monophosphorylated, hybrid oligosaccharides (e.g., peak 10 in anthranilic acid labeled N-linked oligosaccharide profiling) between about 6.0% to about 8.1%. For example, a recombinant human α-galactosidase-A protein provided herein can have a percentage of total N-linked hybrid oligosaccharides that are monosialylated, monophosphorylated hybrid oligosaccharides (e.g., peak 10 in anthranilic acid labeled N-linked oligosaccharide profiling) that is greater than about 8.2% (e.g., greater than about 8.3%, greater than about 8.4%, greater than about 8.5%, greater than about 8.6%, greater than about 8.7%, greater than about 8.8%, greater than about 8.9%, greater than about 9.0%, greater than about 9.1%, greater than about 9.2%, greater than about 9.3%, greater than about 9.4%, greater than about 9.5%, greater than about 9.6%, greater than about 9.7%, greater than about 9.8%, greater than about 9.9%, greater than about 10.0%, greater than about 10.1%, greater than about 10.2%, greater than about 10.3%, greater than about 10.4%, greater than about 10.5%, greater than about 10.6%, greater than about 10.7%, greater than about 10.8%, greater than about 10.9%, greater than about 11.0%, greater than about 11.1%, greater than about 11.2%, greater than about 11.3%, greater than about 11.4%, or greater than about 11.5%). For example, a recombinant human α-galactosidase-A protein provided herein can have a percentage of total N-linked hybrid oligosaccharides that are monosialylated, monophosphorylated hybrid oligosaccharides (e.g., peak 10 in anthranilic acid labeled N-linked oligosaccharide profiling) that is between about 8.5% and 10.5%, between about 9.0% and about 11.0%, or between about 8.5% and about 9.5%.

Exemplary methods for determining the percentage of total N-linked oligosaccharides that are monosialylated and monophosphorylated oligosaccharides (e.g., peak 10 in anthranilic acid labeled N-linked oligosaccharide profiling) are described in the Examples. Additional methods are known in the art.

XI. Isoelectric Point

The recombinant human α-galactosidase-A proteins provided herein also have a shifted isoelectric point as compared to Fabrazyme® when analyzed by imaged capillary isoelectric focusing (icIEF) (see, Example 3 and Table 3).

Exemplary methods for determining the isoelectric point of a polypeptide are described in the Examples. Additional methods for determining the isoelectric point of a polypeptide (e.g., isoelectric focusing gels) are known in the art.

XII. Mole/Mole Ratio of Mannose-6-Phosphate/Protein

Recombinant human α-galactosidase-A proteins provided herein can have a mole to mole ratio of mannose-6-phosphate to protein that is about the same or greater than Fabrazyme®. An increased mole to mole ratio of mannose-6-phosphate to protein is thought to increase the cellular update of the protein by cells expressing a mannose-6-phosphate receptor in the plasma membrane.

Fabrazyme® has a mole to mole ratio of mannose-6-phosphate to protein of about 1.7 to about 3.1. For example, a recombinant human α-galactosidase-A protein provided herein (FZ2G) can have a mole/mole ratio of mannose-6-phosphate to protein that is substantially the same as Fabrazyme® or greater than 1.7 (e.g., greater than 1.8, greater than 1.9, greater than 2.0, greater than 2.1, greater than 2.2, greater than 2.3, greater than 2.4, greater than 2.5, greater than 2.6, greater than 2.7, greater than 2.8, greater than 2.9, greater than 3.0, greater than 3.1, greater than 3.2, greater than 3.3, greater than 3.4, or greater than 3.5). For example, a recombinant human α-galactosidase-A protein provided herein (FZ2G) can have a mole/mole ratio of mannose-6-phosphate to protein that is between about 1.8 and about 3.5 (e.g., between about 1.8 to about 3.4, between about 1.8 to about 3.3, between about 1.8 and about 3.2, between about 1.8 and about 3.1, between about 1.8 and about 3.0, between about 1.8 and about 2.9, between about 1.8 and about 2.8, between about 1.8 and about 2.7, between about 1.8 and about 2.6, between about 1.8 and about 2.5, 1.8 and about 2.4, between about 1.8 and about 2.3, between about 1.8 and about 2.2, between about 1.8 and about 2.1, between about 1.8 and about 2.0, between about 1.9 and about 3.5, between about 1.9 and about 3.4, between about 1.9 and about 3.3, between about 1.9 and about 3.2, between about 1.9 and about 3.1, between about 1.9 and about 3.0, between about 1.9 and about 2.9, between about 1.9 and about 2.8, between about 1.9 and about 2.7, between about 1.9 and about 2.6, between about 1.9 and about 2.5, between about 1.9 and about 2.4, between about 1.9 and about 2.3, between about 1.9 and about 2.2, between about 1.9 and about 2.1, between about 2.0 and about 3.5, between about 2.0 and about 3.4, between about 2.0 and about 3.3, between about 2.0 and about 3.2, between about 2.0 and about 3.1, between about 2.0 and about 3.0, between about 2.0 and about 2.9, between about 2.0 and about 2.8, between about 2.0 and about 2.7, between about 2.0 and about 2.6, between about 2.0 and about 2.5, between about 2.0 and about 2.4, between about 2.0 and about 2.3, between about 2.0 and about 2.2, between about 2.1 and about 3.5, between about 2.1 and about 3.4, between about 2.1 and about 3.3, between about 2.1 and about 3.2, between about 2.1 and about 3.1, between about 2.1 and about 3.0, between about 2.1 and about 2.9, between about 2.1 and about 2.8, between about 2.1 and about 2.7, between about 2.1 and about 2.6, between about 2.1 and about 2.5, between about 2.1 and about 2.4, between about 2.1 and about 2.3, between about 2.2 and about 3.5, between about 2.2 and about 3.4, between about 2.2 and about 3.3, between about 2.2 and about 3.2, between about 2.2 and about 3.1, between about 2.2 and about 3.0, between about 2.2 and about 2.9, between about 2.2 and about 2.8, between about 2.2 and about 2.7, between about 2.2 and about 2.6, between about 2.2 and about 2.5, between about 2.2 and about 2.4, between about 2.3 and about 3.5, between about 2.3 and about 3.4, between about 2.3 and about 3.3, between about 2.3 and about 3.2, between about 2.3 and about 3.1, between about 2.3 and about 3.0, between about 2.3 and about 2.9, between about 2.3 and about 2.8, between about 2.3 and about 2.7, between about 2.3 and about 2.6, between about 2.3 and about 2.5, between about 2.4 and about 3.5, between about 2.4 and about 2.9, between about 2.4 and about 2.8, between about 2.4 and about 2.7, between about 2.4 and about 2.6, between about 2.5 and about 3.5, between about 2.5 and about 3.4, between about 2.5 and about 3.3, between about 2.5 and about 3.2, between about 2.5 and about 3.1, between about 2.5 and about 3.0, between about 2.5 and about 2.9, between about 2.5 and about 2.8, between about 2.5 and about 2.7, between about 2.6 and about 3.5, between about 2.6 and about 3.4, between about 2.6 and about 3.3, between about 2.6 and about 3.2, between about 2.6 and about 3.1, between about 2.6 and about 3.0, between about 2.6 and about 2.9, between about 2.6 and about 2.8, between about 2.7 and about 3.5, between about 2.7 and about 3.4, between about 2.7 and about 3.3, between about 2.7 and about 3.2, between about 2.7 and about 3.1, between about 2.7 and about 3.0, between about 2.7 and about 2.9, between about 2.8 and about 3.5, between about 2.8 and about 3.4, between about 2.8 and about 3.3, between about 2.8 and about 3.2, between about 2.8 and about 3.1, between about 2.8 and about 3.0, between about 2.9 and about 3.5, between about 2.9 and about 3.4, between about 2.9 and about 3.3, between about 2.9 and about 3.2, between about 2.9 and about 3.1, between about 3.0 and about 3.5, between about 3.0 and about 3.4, between about 3.0 and about 3.3, between about 3.0 and about 3.2, between about 3.1 and about 3.5, between about 3.1 and about 3.4, between about 3.1 and about 3.3, between about 3.2 and about 3.5, between about 3.4 and about 3.4, or between about 3.3 and about 3.5).

Exemplary methods for determining the mole/mole ratio of mannose-6-phosphate to protein are described in the Examples. Additional methods are known in the art.

Functional Properties

Recombinant human α-galactosidase-A proteins provided herein can have one or more (e.g., one, two, or three) of the following functional features: increased endocytosis (e.g., increased rate of endocytosis) by a mammalian cell expressing mannose-6-phosphate receptor, decreased binding to asialoglycoprotein receptor, and increased affinity to mannose-6-phosphate receptor, each as compared to Fabrazyme®.

Methods for determining the endocytosis (e.g., rate of endocytosis) of a recombinant human α-galactosidase-A protein in a mammalian cell expressing mannose-6-phosphate are known in the art (e.g., Osborne et al., Curr. Protoc. Cell Biol., Chapter 11, Unit 11.18, 2005). Non-limiting examples of mammalian cells expressing mannose-6-phosphate receptor include fibroblasts and epithelial cells. As is known in the art, the endocytosis of recombinant human α-galactosidase-A protein can be detected by a decrease in the levels of the protein in a tissue culture medium (or serum of a mammal), an increase in the lysosomal or intracellular levels of recombinant human α-galactosidase-A protein in a mammalian cell expressing mannose-6-phosphate receptor, or indirectly, e.g., as a decrease in the accumulation of glycosphingolipids with terminal α-galactosyl residues, such as globotriaoscylceramide (GL-3), in a contacted mammalian cell or in a tissue culture medium (or serum of a mammal). A decrease in the levels of recombinant human α-galactosidase-A protein in a tissue culture medium (or serum of a mammal) can be determined, for example, using an antibody-based assay (e.g., an enzyme-linked immunosorbent assay) or an activity assay (e.g., an activity assay using pNP or 4MU as substrates). Examples of antibodies that bind to recombinant human α-galactosidase-A protein are available from Millipore, LifeSpan BioSciences, Inc., Thermo Scientific Pierce Antibodies, Acris Antibodies GmbH, and R & D Systems. Methods for determining the lysosomal or intracellular levels of recombinant human α-galactosidase-A protein can include, e.g., the use of immunofluorescence microscopy, cell permeabilization and immunoblotting, and/or mass spectrometry of cellular or lysosomal lysate. A decrease in the accumulation of globotriaoscylceramide (GL-3) can be determined, e.g., by detecting the levels of GL-3 in a tissue culture medium or in the serum of a mammal over time using mass spectrometry (e.g., Kim et al., *Korean J. Intern. Med.* 25:415-421, 2010) or an antibody-based assay (e.g., U.S. Patent Application Publication No. 2012/0178105). In each instance, endocytosis of a recombinant human α-galactosidase-A protein can be compared to Fabrazyme®.

Methods for determining the ability of a protein (e.g., recombinant human α-galactosidase-A protein) to bind to asialoglycoprotein receptor are known in the art. For example, an assay to determine binding of a recombinant human α-galactosidase-A protein to asialoglycoprotein receptor can include a step of contacting a cell (e.g., a hepatocyte) expressing asialoglycoprotein. Binding of a recombinant human α-galactosidase-A protein to asialoglycoprotein receptor can also be determined using surface plasmon resonance (e.g., Biacore technology) (see, e.g., Stokmaier et al., Bioorg. Med. Chem. 17:7254-7264, 2009) or the fluorescent polarization asialoglycoprotein receptor binding assay described in Kornilova et al. (*Anal. Biochem.* 425:43-46, 2012). In any instance, binding of a recombinant human α-galactosidase-A protein to asialoglycoprotein receptor can be compared to Fabrazyme®.

Methods for determining binding of a recombinant α-galactosidase-A protein to mannose-6-phosphate receptor can be performed using assays that include a step of contacting a recombinant α-galactosidase-A protein to a cell (e.g., a fibroblast or an endothelial cell) expressing mannose-6-phosphate receptor. In other examples, binding of a recombinant α-galactosidase-A protein to mannose-6-phosphate receptor can be determined using surface plasmon resonance (e.g., Biacore technology) or affinity chromatography methods. Binding of a recombinant human α-galactosidase-A protein to mannose-6-phosphate receptor can be compared to Fabrazyme®.

Exemplary Recombinant Human α-Galactosidase-A Proteins

Recombinant human α-galactosidase-A protein provided herein can have a percentage of total N-linked oligosaccharides that are monosialylated oligosaccharides (e.g., peak 3 in anthranilic acid labeled N-linked oligosaccharide profiling) between about 0.1% and about 1.6% (e.g., between about 0.1% and about 1.3% or between about 0.1% and about 1.0%) and a percentage of total N-linked oligosaccharides that are bis-mannose-6-phosphate oligosaccharides (e.g., peak 11 in anthranilic acid labeled N-linked oligosaccharide profiling) greater than about 7.5% (e.g., greater than about 8.5%, greater than about 9.0%, or greater than about 9.5%). Recombinant human α-galactosidase-A protein can further have a percentage of total N-linked oligosaccharides that are bisialylated fucose-containing oligosaccharides (e.g., peak 4 in anthranilic acid labeled N-linked oligosaccharide profiling) greater than about 13.0% (e.g., greater than about 13.5%, greater than about 14.0%, greater than about 14.5%, greater than about 15.0%, greater than about 15.5%, or greater than about 16.0%) and a percentage of total N-linked oligosaccharides that are triantennary, trisialylated oligosaccharides of form 2 (e.g., peak 6' in anthranilic acid labeled N-linked oligosaccharide profiling) greater than about 2.0% (e.g., greater than about 2.5%, greater than about 3.0%, greater than about 3.5%, greater than about 4.0%, greater than about 4.5%, greater than about 5.0%, greater than about 5.5%, greater than about 6.0%, greater than about 6.5%, or greater than about 7.0%).

Recombinant human α-galactosidase-A protein can further have one or more (e.g., two, three, four, five, six, seven, eight, or nine) of the following physical characteristics: a percentage of total N-linked oligosaccharides that are neutrally-charged oligosaccharides (e.g., peak 1 in anthranilic acid labeled N-linked oligosaccharide profiling) between about 0.1% and about 3.9% (e.g., between about 0.1% and about 3.5%, between about 0.1% and about 3.0%, between about 0.1% and about 2.5%, or between about 0.1% and about 2.0%); a percentage of total N-linked oligosaccharides that are monosialylated fucose-containing oligosaccharides (e.g., peak 2 in anthranilic acid labeled N-linked oligosaccharide profiling) between about 0.1% and about 3.0% (e.g., between about 0.1% and about 2.5%, or between about 0.1% and about 2.0%); a percentage of total N-linked oligosaccharides that are bisialylated oligosaccharides (e.g., peak 5 in anthranilic acid labeled N-linked oligosaccharide profiling) between about 0.1% and about 5.3% (e.g., between about 0.1% and about 5.0%, between about 0.1% and about 4.5%, between about 0.1% and about 4.0%, between about 0.1% and about 3.5%, between about 0.1% and about 3.0%, or between about 0.1% and about 2.5%); a percentage of total N-linked oligosaccharides that are triantennary, trisialylated oligosaccharides of form 1 (e.g., peak 6 in anthranilic acid labeled N-linked oligosaccharide profiling) that is between about 0.1% and about 9.0% (e.g., between about 0.1% and about 8.5%, between about 0.1% and about 8.0%, between about 0.1% and about 7.5%, between about 0.1% and about 7.0%, between about 0.1% and about 6.5%, between about 0.1% and about 6.0%, between about 0.1% and about 5.5%, between about 0.1% and about 5.0%, between about 0.1% and about 4.5%, between about 0.1% and about 4.0%, between about 0.1% and about 3.5%, between about 0.1% and about 3.0%, between about 0.1% and about 2.5%, or between about 0.1% and about 2.0%); a percentage of total N-linked oligosaccharides that are mannose-6-phosphate oligosaccharides (e.g., peak 7 in anthranilic acid labeled N-linked oligosaccharide profiling) that is between about 0.1% and about 7.0% (e.g., between about 0.1% and about 6.5%, between about 0.1% and about 6.0%, between about 0.1% and about 5.5%, between about 0.1% and about 5.0%, between about 0.1% and about 4.5%, or between about 0.1% and about 4.0%); a percentage of total N-linked oligosaccharides that are monophosphorylated oligosaccharides (e.g., peak 8 in anthranilic acid labeled N-linked oligosaccharide profiling) greater than about 14.8% (e.g., greater than about 15.0%, greater than about 15.5%, greater than about 16.0%, greater than about 16.5%, greater than about 17.0%, greater than about 17.5%, greater than about 18.0%, greater than about 18.5%, greater than about 19.0%, greater than about 19.5%, greater than about 20.0%, greater than about 20.5%, greater than about 21.0%, greater than about 21.5%, greater than about 22.0%, greater than about 22.5%, or greater than about 23.0%); a percentage of total N-linked oligosaccharides that are tetrasialylated oligosaccharides (e.g., peak 9 in anthranilic acid labeled N-linked oligosaccharide profiling) that is greater than about 4.9% (e.g., greater than about 5.0%, greater than about 5.5%, greater than about 6.0%, greater than about 6.5%, greater than about 7.0%, greater than about 7.5%, or greater than about 8.0%); and a percentage of total N-linked oligosaccharides that are monosialylated, monophosphorylated hybrid oligosaccharides (e.g., peak 10 in anthranilic acid labeled N-linked oligosaccharide profiling) that is greater than about 8.2% (e.g., greater than about 8.5%, greater than about 9.0%, greater than about 9.5%, or greater than about 10.0%).

The recombinant human α-galactosidase-A protein can also have one or more of the following functional features: increased endocytosis (e.g., increased rate of endocytosis) by a mammalian cell expressing mannose-6-phosphate receptor, decreased binding to asialoglycoprotein receptor, and increased affinity to mannose-6-phosphate receptor as compared to Fabrazyme®.

In other examples, recombinant human α-galactosidase-A protein has a percentage of total N-linked oligosaccharides that are monosialylated oligosaccharides (e.g., peak 3 in anthranilic acid labeled N-linked oligosaccharide profiling) that is less than Fabrazyme® and a percentage of total N-linked oligosaccharides that are bis-mannose-6-phosphate oligosaccharides (e.g., peak 11 in anthranilic acid labeled N-linked oligosaccharide profiling) that is greater than Fabrazyme®. Recombinant human α-galactosidase-A protein can also have a percentage of total N-linked oligosaccharides that are bisialylated fucose-containing oligosaccharides (e.g., peak 4 in anthranilic acid labeled N-linked oligosaccharide profiling) that is about the same or greater than Fabrazyme®, and a percentage of total N-linked oligosaccharides that are triantennary, trisialylated oligosaccharides of form 2 (e.g., peak 6' in anthranilic acid labeled N-linked oligosaccharide profiling) that is greater than Fabrazyme®.

Recombinant human α-galactosidase-A protein can also have one or more of the following structural features: a percentage of total N-linked oligosaccharides that are neutrally-charged oligosaccharides (e.g., peak 1 in anthranilic acid labeled N-linked oligosaccharide profiling) that is less than Fabrazyme®; a percentage of total N-linked oligosaccharides that are monosialylated fucose-containing oligosaccharides (e.g., peak 2 in anthranilic acid labeled N-linked oligosaccharide profiling) that is about the same or less than Fabrazyme®; a percentage of total N-linked oligosaccharides that are bisialylated oligosaccharides (e.g., peak 5 in anthranilic acid labeled N-linked oligosaccharide profiling) that is less than Fabrazyme®; a percentage of total N-linked oligosaccharides that are triantennary, trisialylated oligosaccharides of form 1 (e.g., peak 6 in anthranilic acid labeled N-linked oligosaccharide profiling) that is less than Fabrazyme®; a percentage of total N-linked oligosaccharides that are mannose-6-phosphate oligosaccharides (e.g., peak 7 in anthranilic acid labeled N-linked oligosaccharide profiling) that is about the same or less than Fabrazyme®; a percentage of total N-linked oligosaccharides that are monophosphorylated oligosaccharides (e.g., peak 8 in anthranilic acid labeled N-linked oligosaccharide profiling) that is greater than Fabrazyme®; a percentage of total N-linked oligosaccharides that are tetrasialylated oligosaccharides (e.g., peak 9 in anthranilic acid labeled N-linked oligosaccharide profiling) that is greater than Fabrazyme®; and a percentage of total N-linked oligosaccharides that are monosialylated, monophosphorylated hybrid structures (e.g., peak 10 in anthranilic acid labeled N-linked oligosaccharide profiling) that is greater than Fabrazyme®. The recombinant human α-galactosidase-A protein can also have one or more of the following functional features: increased endocytosis (e.g., increased rate of endocytosis) by a mammalian cell expressing mannose-6-phosphate receptor, decreased binding to asialoglycoprotein receptor, and increased affinity to mannose-6-phosphate receptor, each as compared to Fabrazyme®.

Expression Vectors

Also provided herein are expression vectors containing a sequence (e.g., cDNA) encoding recombinant human α-galactosidase-A proteins of the present invention. For example, the expression vector can include a sequence (e.g., a cDNA) encoding recombinant human α-galactosidase-A protein that is at least 90% identical (e.g., at least 90%, 92%, 94%, 96%, 98%, 99% or 100% identical) to SEQ ID NO: 1. In addition to that sequence, the expression vectors can include a promoter (and optionally one or more enhancer sequences) operably linked to the 5' end of the sequence (e.g., cDNA) encoding the recombinant human α-galactosidase-A protein. The expression vectors can include a sequence encoding a peptide of human CD52 protein with a TTG start codon operably linked to the 5' end of the sequence (e.g., cDNA) encoding the recombinant protein and a sequence encoding a poly(A) recognition site operably linked to the 3' end of the sequence (e.g., cDNA) encoding the recombinant protein. The expression vectors can include a sequence (e.g., cDNA) encoding a mammalian selection marker (e.g., a human or dog synthetase protein) and a promoter sequence operably linked to the 5' end of the sequence (e.g., cDNA) encoding the mammalian selection marker, and optionally, a SV40 early intron sequence and poly(A) signal sequence that are both operably linked to the 3' end of the sequence (e.g., cDNA) encoding the mammalian selection gene. Expression vectors can include one or more (e.g., two or three) of: a prokaryotic promoter sequence that is operably linked to the 5' end of the sequence encoding a prokaryotic selection gene (e.g., an ampicillin resistance gene), a prokaryotic origin of replication sequence, and a eukaryotic origin of replication sequence.

Non-limiting examples of promoter sequences (and optionally one or more enhancer sequence(s)) that can be operably linked to the sequence (e.g., cDNA) encoding recombinant human α-galactosidase-A protein include: Simian Virus 40 (SV40) early promoter, ribosomal protein 21 (rpS21) promoter, hamster β-actin promoter, cytomegalovirus (CMV) promoter (e.g., CMV immediate early promoter (see, e.g., Teschendorf et al., *Anticancer Res.* 22:3325-3330, 2002), ubiquitin C (UBC) promoter, elongation factor 1-α (EF1A) promoter, phosphoenolpyruvate carboxykinase (PCK) promoter, 1E2 promoter/enhancer region from mouse CMV (see, e.g., Chatellard et al., *Biotechnol. Bioeng.* 96:106-117, 2007), and chicken β-actin promoter. Additional non-limiting examples of human gene promoters that can be used in any of the expression vectors described herein are described in the Mammalian Promoter Database (Wistar Institute website at mrpombdb.wister.upenn.edu). Additional examples of mammalian promoter sequences that can be used in the expression vectors are known in the art. One non-limiting example of a promoter and an enhancer that can be used in an expression plasmid is a chicken β-actin promoter with a CMV enhancer (known in the art as a CAGG promoter). The expression vectors provided herein can include a rpS21 promoter, a hamster β-actin promoter, or a SV40 early promoter sequence operably linked to the 5' end of the sequence (e.g., cDNA) encoding human recombinant α-galactosidase-A protein, a sequence encoding a peptide of human CD52 protein with a TTG start codon operably linked to the 5' end of the nucleic acid (e.g., cDNA) encoding human recombinant α-galactosidase-A protein (e.g., any of the nucleic acids encoding human recombinant α-galactosidase-A protein described herein), and a sequence containing a poly(A) recognition site operably linked to a 3' end of the nucleic acid sequence encoding recombinant human α-galactosidase-A protein.

Non-limiting examples of poly(A) recognition site sequences are bovine growth hormone poly(A) recognition site. The structural features of a human poly(A) recognition site are described in Nunes et al., *EMBO J.* 29:1523-1536, 2010. Additional poly(A) recognitions sites are well-known in the art.

In some examples, the expression vector includes a hamster β-actin promoter and sequence encoding a peptide of human CD52 protein with a TTG start codon both operably linked to the 5' end of the sequence (e.g., cDNA) encoding the recombinant human α-galactosidase-A protein, and a SV40 early intron and poly(A) recognition sequence operably linked to the 3' end of the sequence (e.g., cDNA) encoding the recombinant human α-galactosidase-A protein.

Some expression vectors can include a sequence encoding a mammalian selection gene. Non-limiting examples of mammalian selection genes include: dihydrofolate reductase gene, hydromycin resistance genes, neomycin resistance genes, blasticidin resistance genes, zeocin resistance genes, glutamine synthetase genes, dihydrofolate resistance genes, and hypoxanthine-guanine phosphoribosyltransferase genes. Examples of sequences encoding these mammalian selection genes are known in the art. The 5' end of the sequence encoding the mammalian selection gene can be operably linked to a promoter (e.g., any of the exemplary promoters described herein or known in the art).

Some expression vectors (e.g., any of the expression vector described herein) can include a mammalian origin of replication sequence and/or a prokaryotic origin of replication sequence. Mammalian origin of replication sequences are known in the art (e.g., Todorovic et al., Front. Biosci. 4: D859-D568, 1999; Aladjem, *Front. Biosci.* 9:2540-2547, 2004; Hamlin, *Bioessays* 14:651-659, 1992). Prokaryotic origin of replication sequences are also known in the art (e.g., Marczynski et al., *Curr. Opin. Genet. Dev.* 3:775-782, 1993).

Figure 4:
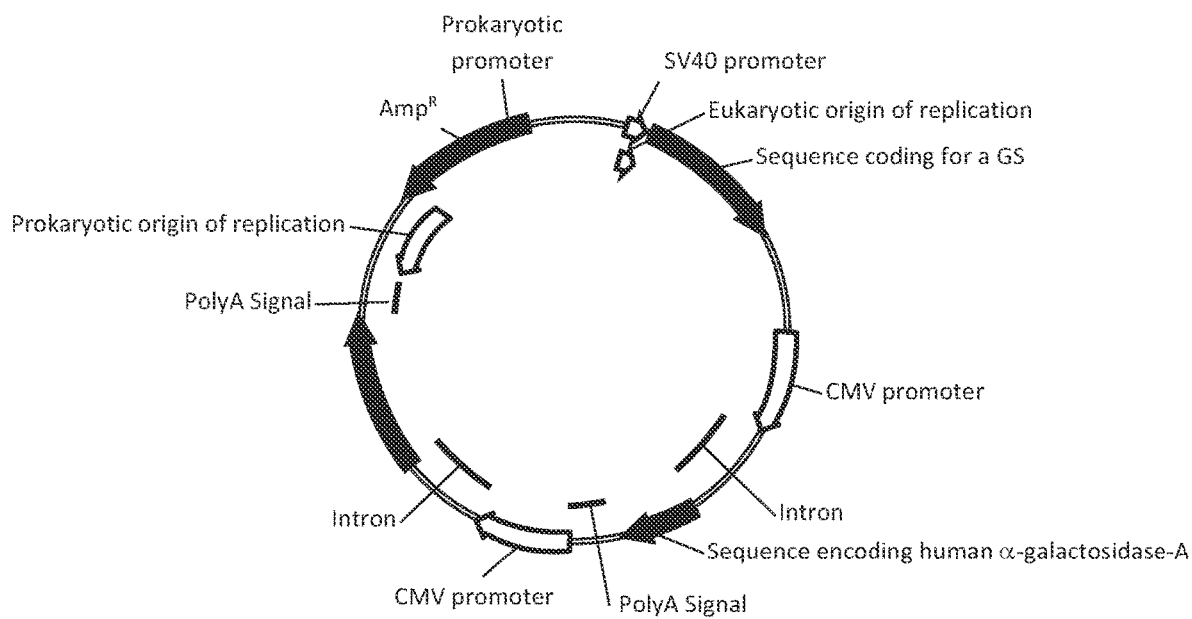
FIG. 4 is a map of a vector that can be used to express recombinant human α-galactosidase-A protein.

A non-limiting example of a vector is a plasmid. Non-limiting examples of plasmids provided herein are shown in FIGS. 3 and 4. FIG. 3 depicts a plasmid encoding the following elements: a nucleic acid (e.g., cDNA) encoding recombinant human α-galactosidase-A protein, a promoter (e.g., hamster β-actin promoter) linked to the 5' end of the nucleic acid encoding human α-galactosidase-A protein, a sequence encoding a peptide of human CD52 that has a TTG start codon that is operably linked to the 5' end of the sequence encoding recombinant human α-galactosidase-A protein, a poly(A) recognition sequence (e.g., SV40 early poly(A) recognition sequence) that is operably linked to the 3' end of the second encoding recombinant human α-galactosidase-A protein, a nucleic acid sequence encoding a mammalian selection gene (marker) (e.g., a dihydrofolate reductase gene or a human or dog glutamine synthetase gene), and a promoter sequence (e.g., SV40 early promoter) operably linked to the 5' end of the nucleic acid sequence encoding the mammalian selection gene (marker). FIG. 4 depicts an expression plasmid that includes: a sequence encoding recombinant human α-galactosidase-A protein, a promoter sequence (e.g., a CMV promoter and intron) operably linked to the 5' end of the sequence encoding the recombinant human α-galactosidase-A protein, a poly(A) recognition sequence (e.g., SV40 early poly(A) recognition sequence) operably linked to the 3' end of the sequence encoding the recombinant human α-galactosidase-A protein, a sequence encoding a mammalian selection gene (marker) (e.g., glutamine synthetase), a promoter sequence (e.g., SV40 promoter) operably linked to the 5' end of the sequence encoding the mammalian selection gene (marker), a prokaryotic origin of replication sequence, a sequence encoding a prokaryotic selection gene (marker) (e.g., an ampicillin resistance gene), a prokaryotic promoter sequence operably linked to the 5' end of the prokaryotic selection gene (marker), and a eukaryotic origin of replication sequence.

An expression vector can be a viral vector. Non-limiting examples of viral vectors include adenovirus vectors, herpes virus vectors, baculovirus vectors, and retroviral vectors. An expression vector can also be a plasmid or a cosmid.

Host Cells

Also provided herein are host cells that include a sequence encoding recombinant human α-galactosidase-A protein described herein. The sequence can be operably linked to a promoter sequence (e.g., any of the exemplary promoter sequences described herein or any of the viral or mammalian promoter sequences known in the art). For example, the sequence encoding recombinant human α-galactosidase-A protein and the sequence of the promoter sequence operably linked to the 5' end of the sequence encoding recombinant human α-galactosidase-A protein can be integrated within a chromosome in the host cell. In other examples, the sequence encoding recombinant human α-galactosidase-A protein and the promoter sequence that is operably linked to the 5' end of the sequence encoding recombinant human α-galactosidase-A protein are present in an expression vector (e.g., any of the expression vectors described herein) within the host cell.

Methods for introducing nucleic acids (e.g., any of the nucleic acids or expression vectors described herein) into a cell (e.g., a mammalian host cell) are known in the art. For example, nucleic acid can be introduced into a cell using lipofection, electroporation, calcium phosphate-mediated transfection, virus (e.g., retroviral) transduction, DEAE-dextran-mediated cell transfection, dendrimer-mediated transfection, sono-poration, optical transfection, impalefection, hydrodynamic delivery, magnetofection, or ballistic transfection.

A host cell can be any type of mammalian cell. For example, a host cell can be a cell line, e.g., Chinese hamster ovary (CHO) cells (e.g., CHO DG44 cells, CHO-Kls cells, C02.31 clonal cells, A14.13 clonal cells, C02.57 clonal cells, and F05.43 clonal cells), Sp2.0, myeloma cells (e.g., NS/0), B-cells, hybridoma cells, T-cells, human embryonic kidney (HEK) cells (e.g., HEK 293E and HEK 293F), African green monkey kidney epithelial cells (Vero) cells, or Madin-Darby Canine (Cocker Spaniel) kidney epithelial cells (MDCK) cells. Additional mammalian cells that can be cultured using the methods described herein are known in the art. A host cell can be, e.g., an epithelial cell, an endothelial cell, a lymphocyte, a kidney cell, a lung cell, a T-cell, a myeloma cell, or a B-cell. Some host cells can be grown in a suspension cell culture or in an adherent cell culture.

Methods of Generating a Mammalian Cell Line

Figure 5:
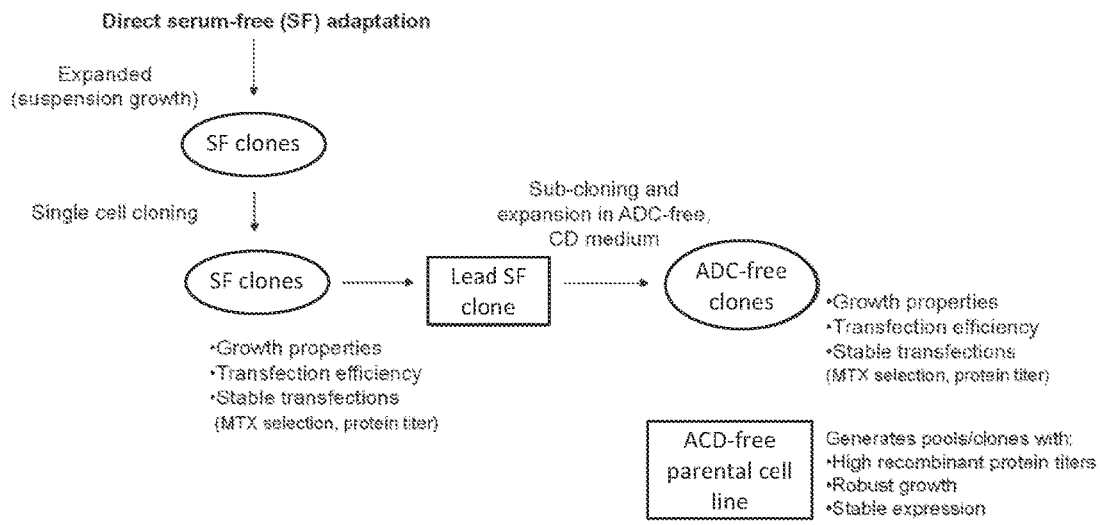
FIG. 5 is a flow-chart showing the steps used to generate a parental cell line optimized for expression of a recombinant glycoprotein.

Also provided herein are methods of generating a mammalian cell line useful for recombinant expression of a glycoprotein (e.g., recombinant human α-galactosidase-A protein, any of the other enzymes listed in Table 1, or any of the other glycoproteins known in the art). FIG. 5 is a flow-chart showing the steps that can be used to generate a parental cell line optimized for expression of a recombinant glycoprotein. These methods can include providing a serum-dependent immortalized cell line and sequentially culturing the mammalian cell line in: (1) a cell culture medium that includes a first concentration (1×) of animal serum for about 5 days to about 30 days (e.g., about 5 days to about 25 days, about 5 days to about 20 days, about 5 days to about 15 days, about 5 days to about 12 days, about 5 days to about 11 days, about 5 days to about 10 days, about 5 days to about 9 days, about 5 days to about 8 days, or about 5 days to about 7 days); (2) a cell culture medium that includes about a 0.2× to about a 0.4× (e.g., about a 0.2× to about a 0.3×) concentration of animal serum for about 5 days to about 30 days (e.g., about 5 days to about 25 days, about 5 days to about 20 days, about 5 days to about 15 days, about 5 days to about 12 days, about 5 days to about 11 days, about 5 days to about 10 days, about 5 days to about 9 days, about 5 days to about 8 days, or about 5 days to about 7 days); and (3) a cell culture medium that includes about 0.01× to about 0.25× (e.g., about 0.01× to about 0.20×, about 0.01× to about 0.15×, or about 0.01× to about 0.08×) of animal serum for about 5 days to about 30 days (e.g., about 5 days to about 25 days, about 5 days to about 20 days, about 5 days to about 15 days, about 5 days to about 12 days, about 5 days to about 11 days, about 5 days to about 10 days, about 5 days to about 9 days, about 5 days to about 8 days, or about 5 days to about 7 days), generating single-cell subclone cultures from the culture after the sequential culturing, and selecting a subclone that has acceptable transfection efficiency, cell growth in serum-free culture medium, and recombinant protein expression; and culturing the selected subclone in a protein-free, serum-free, chemically-defined medium for about 5 days to about 30 days (e.g., about 5 days to about 25 days, about 5 days to about 20 days, about 5 days to about 15 days, about 5 days to about 12 days, about 5 days to about 11 days, about 5 days to about 10 days, about 5 days to about 9 days, about 5 days to about 8 days, or about 5 days to about 7 days); generating a single-cell subclone cultures from the culture after culturing in the protein-free, serum-free, chemically-defined medium; and selecting a subclone that has acceptable transfection efficiency, peak cell density, growth properties, volumetric productivity rate (VPR), and glycosylation profile for a glycoprotein, where the selected subclone of (f) is useful for recombinant expression of a glycoprotein.

Also provided are methods of generating a mammalian cell line useful for recombinant expression of a glycoprotein (e.g., any of the recombinant proteins described herein or known in the art) that include: (a) providing a serum-dependent immortalized cell line and sequentially culturing the mammalian cell line in: (1) a cell culture medium that includes a first concentration (1×) (e.g., about 5%) of animal serum for about 1 day to about 30 days (e.g., about 2 days to about 25 days, about 2 days to about 20 days, about 2 days to about 15 days, about 2 days to about 12 days, about 2 days to about 11 days, about 2 days to about 10 days, about 2 days to about 9 days, about 2 days to about 8 days, or about 2 days to about 7 days); (2) a cell culture medium that includes about a 0.2× to about a 0.6× (e.g., about a 0.2× to about a 0.5×) concentration of animal serum (e.g., fetal bovine serum) for about 1 day to about 30 days (e.g., about 2 days to about 25 days, about 2 days to about 20 days, about 2 days to about 15 days, about 2 days to about 12 days, about 2 days to about 11 days, about 2 days to about 10 days, about 2 days to about 9 days, about 2 days to about 8 days, or about 2 days to about 7 days); and (3) a cell culture medium that includes about 0× to about 0.20× (e.g., about 0× to about 0.15×, about 0× to about 0.10×, or about 0× to about 0.05×) of animal serum (e.g., fetal bovine serum) for about 5 days to about 30 days (e.g., about 5 days to about 25 days, about 5 days to about 20 days, about 5 days to about 15 days, about 5 days to about 12 days, about 5 days to about 11 days, about 5 days to about 10 days, about 5 days to about 9 days, about 5 days to about 8 days, or about 5 days to about 7 days); (b) generating single-cell subclone cultures from the culture after the sequential culturing, and selecting a subclone culture that has acceptable transfection efficiency, cell growth in serum-free culture medium, and recombinant protein expression (e.g., selecting a subclone culture that has the best transfection efficiency, cell growth, and recombinant protein expression as compared to the other tested subclone cultures); (c) generating single-cell subclone cultures from the selected subclone culture in (b); and (d) selecting a single-cell subclone culture generated in (c) that has acceptable transfection efficiency, peak cell density (e.g., peak cell density in serum-free medium), growth properties (e.g., growth in serum-free medium), volumetric productivity rate (VPR), and recombinant protein expression, where the selected subclone of (d) is useful for recombinant expression of a glycoprotein (e.g., a subclone culture that has the best transfection efficiency, peak cell density, growth properties, VPR, and recombinant protein expression) as compared to the other tested subclone cultures).

Also provided herein are mammalian cells or mammalian cell lines produced by any of the methods described herein. Non-limiting examples of serum-dependent immortalized cell lines that can be used in any of the methods described herein include Chinese Hamster Ovary (CHO) cells, myeloma cells, B-cells, hybridoma cells, T-cells, human embryonic kidney (HEK) cells, African green monkey kidney epithelial cells (Vero) cells, and Madin-Darby Canine (Cocker Spaniel) kidney epithelial cells (MDCK) cells. Other serum-dependent immortalized cell lines that can be used in any of the methods described herein are known in the art. For example, the serum-dependent immortalized cell line can be an epithelial cell line, an endothelial cell line, a lymphocyte cell line, a kidney cell line, a lung cell line, a T-cell line, a myeloma cell line, or a B-cell line. In some examples, the serum-dependent immortalized cell line grows in suspension. In other examples, the serum-dependent immortalized cell line grows in adherent cell culture.

In some examples, the serum-dependent immortalized cell line does not endogenously express dihydrofolate reductase. The selected subclone (either the first or the second subclone selected in the methods) can be grown in suspension. Methods for culturing an immortalized mammalian cell line are known in the art.

Methods for determining the transfection efficiency, cell growth in a serum-free culture medium, recombinant protein expression, peak cell density (e.g., peak viable cell density), cell growth properties, volumetric productivity rate, and the glycosylation profile of a produced recombinant protein are well-known in the art. For example, transfection efficiency can be determined by detecting the level of expression of a reporter gene in an expression plasmid transfected into the cell (e.g., the expression of such a reporter gene can be detected using fluorescence-assisted cell sorting). Recombinant protein expression can, for example, be determined by detecting the levels of the recombinant protein present in a tissue culture medium or within the cell using an antibody that specifically binds to the recombinant protein. Recombinant protein expression can be, for example, one or both of an antibody or an enzyme (e.g., recombinant human α-galactosidase-A protein or any of the enzymes listed in FIG. 1). Peak cell density and cell growth can be assessed, e.g., by measuring the cell density (e.g., viable cell density) over time in a cell culture (e.g., using a hemocytometer or other commercially available automated cell counters). The volumetric productivity rate of a cell can be determined using methods known in the art by assessing the levels of recombinant protein present in a cell culture medium or within the cell over time. The glycosylation profile of a recombinant glycoprotein produced by a cell can be determined, for example, using any of the methods described in the Examples section of the present specification (e.g., 2-amino benzoic acid (AA)-derivatization and capillary electrophoresis with laser-induced fluorescent detection).

As is well-known in the art, a mammalian cell line produced by the methods described herein can be stored at low temperature (e.g., below −20° C., below −30° C., below −40° C., below −50° C., below −60° C., below −70° C., or below-80° C.) for future use. Methods for preparing stocks of a mammalian cell line for storage at low temperatures is described, for example, in Hewitt, *Methods Mol. Biol.* 640:83-105, 2010, and Phelan, *Curr. Protoc. Hum. Genet. Apendix* 3:3G, 2006). In some examples, the mammalian cell lines produced by the methods described herein are not exposed to serum-containing and/or serum-containing culture medium (e.g., prior to storage and/or after storage). In some examples, the mammalian cell lines produced by the methods described herein are cultured only in animal-derived component (ADC)-free culture medium. In some examples, the mammalian cell lines produced by the methods described herein are only cultured in serum-free, protein-free, chemically defined growth medium.

Methods of Producing a Recombinant Glycoprotein

Also provided herein are methods of producing a recombinant glycoprotein (e.g., recombinant human α-galactosidase-A protein, any of the enzymes listed in FIG. 1, or any recombinant glycoprotein known in the art). These methods include providing a mammalian cell produced by any of the methods described herein, introducing into the cell a nucleic acid (e.g., an expression vector) that includes a sequence encoding a glycoprotein (e.g., recombinant human α-galactosidase-A protein, any of the enzymes described in FIG. 1, and any other glycoprotein known in the art), culturing the cell in a serum-free culture medium under conditions sufficient to produce the glycoprotein, and harvesting the glycoprotein from the cell or the growth culture medium. Also provided are recombinant glycoproteins (e.g., recombinant human α-galactosidase-A protein) produced by any of the methods described herein.

In some instances, the nucleic acid that includes a sequence encoding a glycoprotein is an expression vector (e.g., any of the expression vectors described herein). In other examples, the nucleic acid that includes a sequence encoding a glycoprotein is integrated into a chromosome of the mammalian cell.

In some examples, culturing is performed using suspension cell culture. In other examples, culturing is performed using a plurality of microcarriers that have a surface allowing attachment and growth of the mammalian cell. The plurality of microcarriers can have an average diameter of, e.g., between about 20 μm to about 1 mm (e.g., between about 20 μm and about 250 μm, between about 100 μm to about 250 μm, between about 150 μm to about 250 μm, between about 250 μm and about 500 μm, between about 200 μm to about 300 μm, between about 750 μm and 1 mm, between about 200 μm to about 800 μm, between about 200 μm and about 500 μm, or between about 500 μm and about 800 μm), where the microcarriers have a surface that is permissive or promotes attachment of a mammalian cell (e.g., any of the mammalian cells described herein or known in the art). In some examples, a microcarrier can include one or more pores (e.g., one or more pores with an average diameter of about 10 μm to about 100 μm). In some instances, the surfaces of the microcarriers and/or the surface of the one or more pores in the plurality of microcarriers are coated with an agent that promotes the attachment of a mammalian cell to the microcarrier (e.g., attachment to the outer surface of the microcarriers and/or the surface of the pores in the microcarrier). Microcarriers may be approximately spherical or ellipsoidal in shape. In some embodiments, the microcarriers have an outer surface and/or the microcarrier pores have a surface that is positively charged (e.g., positively charged due to the presence of N,N-diethylaminoethyl groups). Non-limiting exemplary microcarriers that can be used in any of the methods described herein include Cyto-Pore™ 1 and CytoPore™ 2 (available from GE Healthcare, Life Sciences, Piscataway, N.J.). Additional examples of microcarriers that can be used for culturing are publicly available and known in the art.

In some examples, the culturing is performed using a bioreactor. The bioreactor can have a volume of, e.g., between about 1 L to about 10,000 L (e.g., between about 1 L to about 50 L, between about 50 L to about 500 L, between about 500 L to about 1000 L, between 500 L to about 5000 L, between about 500 L to about 10,000 L, between about 5000 L to about 10,000 L, between about 1 L and about 10,000 L, between about 1 L and about 8,000 L, between about 1 L and about 6,000 L, between about 1 L and about 5,000 L, between about 100 L and about 5,000 L, between about 10 L and about 100 L, between about 10 L and about 4,000 L, between about 10 L and about 3,000 L, between about 10 L and about 2,000 L, or between about 10 L and about 1,000 L). The amount of liquid culture medium present in a bioreactor can be, e.g., between about between about 0.5 L to about 5,000 L (e.g., between about 0.5 L to about 25 L, between about 25 L to about 250 L, between about 250 L to about 500 L, between 250 L to about 2500 L, between about 250 L to about 5,000 L, between about 2500 L to about 5,000 L, between about 0.5 L and about 5,000 L, between about 0.5 L and about 4,000 L, between about 0.5 L and about 3,000 L, between about 0.5 L and about 2,500 L, between about 50 L and about 2,500 L, between about 5 L and about 50 L, between about 5 L and about 2,000 L, between about 5 L and about 1,500 L, between about 5 L and about 1,000 L, or between about 5 L and about 500 L). Culturing cells can be performed, e.g., using a fed-batch bioreactor or a perfusion bioreactor. Culturing can be performed by fed-batch culturing or perfusion culturing (e.g., in a bioreactor).

The interior surface of any of the bioreactors described herein may have at least one coating (e.g., at least one coating of gelatin, collagen, poly-L-ornithine, polystyrene, and laminin), and as is known in the art, one or more ports for the sparging of $O_2$, $CO_2$, and $N_2$ into the liquid culture medium, and a stir mechanism for agitating the liquid culture medium. The bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an alternating tangential flow (ATF) or tangential flow filtration (TFF) system). Culturing can include exposing the liquid culture medium in the bioreactor to an atmosphere that includes at most or about 15% $CO_2$ (e.g., at most or about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or at most or about 1% $CO_2$).

Culturing can be performed at a temperature of about 31° C. to about 40° C. Skilled practitioners will appreciate that the temperature can be changed at specific time point(s) during the culturing, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the bioreactor with the mammalian cell). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). For example, the temperature can be shifted downwards (e.g., a change of greater than 0.05° C. or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.).

The culturing can be performed using protein-free, serum-free, chemically-defined medium. Non-limiting examples of such media are known in the art and are commercially available. Non-limiting examples of useful culture medium include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and PowerCHO medium (Lonza Group, Ltd.; Basel, Switzerland).

The mammalian cell can be any of the mammalian cells described herein. For example, the mammalian cell can be a CHO cell. The mammalian cell can be a cell that does not endogenously express dihydrofolate reductase (e.g., a CHO cell that does not endogenously express dihydrofolate reductase).

The recombinant glycoprotein can be an enzyme (e.g., human α-galactosidase-A protein, any of the proteins listed in FIG. 1, or any other glycoprotein known in the art) or an antibody or an antigen-binding fragment thereof. In some examples, the nucleic acid (e.g., expression vector) includes a sequence that is at least 90% (e.g., at least 91%, 92%, 93%, 94%, 95%, 96%, 97%, 98%, 99%, or 100%) identical to SEQ ID NO: 1. The nucleic acid (e.g., expression vector) can comprise a promoter sequence operably linked to the 5' end of the nucleic acid encoding the glycoprotein, a sequence encoding a peptide of human CD52 protein with a TTG start codon operably linked to the 5' end of the nucleic acid encoding the glycoprotein, and a sequence encoding a poly(A) recognition site operably linked to the 3' end of the nucleic acid encoding a glycoprotein. For example, the promoter sequence can be selected from the group consisting of: hamster rpS21 promoter, hamster β-actin promoter, and SV40 early promoter. The sequence encoding the poly (A) recognition site can be a SV40 early poly(A) recognition sequence. In some examples, the promoter sequence can be hamster β-actin promoter and the poly(A) recognition sequence is a SV40 early poly(A) recognition sequence. In some examples, the nucleic acid further includes a sequence encoding a human or dog glutamine synthetase (e.g., where the 5' end of the nucleic acid encoding the human or dog glutamine synthetase is operably linked to a SV40 early promoter and the 3' end of the nucleic acid encoding the human or dog glutamine synthetase is operably linked to a SV40 early intron and poly(A) signal sequence). In some examples, the nucleic acid further includes a sequence encoding a dihydrofolate reductase (DHFR) (e.g., human or mouse DHFR) (e.g., where the 5' end of the nucleic acid encoding the dihydrofolate reductase is operably linked to a SV40 early promoter and the 3' end of the nucleic acid encoding the dihydrofolate reductase is operably linked to a SV40 early intron and poly(A) signal sequence).

The culturing can be performed using a perfusion bioreactor. Perfusion culturing is well-known in the art and includes removing from a bioreactor a first volume of a first liquid culture medium (e.g., that includes any concentration of mammalian cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume.

Skilled practitioners will appreciate that the first liquid culture medium and the second liquid culture medium can be the same type of media (e.g., serum-free or serum-free, protein-free chemically-defined medium). In other instances, the first liquid culture medium and the second liquid culture medium can be different.

The first volume of the first liquid culture medium can be removed, e.g., using a mechanical system and/or by seeping or gravity flow of the volume through a sterile membrane with a molecular weight cut-off that excludes mammalian cells present in the volume.

The second volume of the second liquid culture medium can be added to the first liquid culture medium in an automated fashion, e.g., by perfusion pump. In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell.

Alternatively or in addition, culturing can be performed using a fed-batch bioreactor. Such culturing is known in the art and includes, over the majority of the culturing period, addition (e.g., periodic or continuous addition) to the first liquid culture medium of a second volume of a second liquid culture medium. Adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the second volume of the second liquid culture medium is added (volume/unit of time) can be varied over the entire or part of the culturing period. For example, the volume of the second liquid culture medium added can change (e.g., gradually increase) over each 24-hour period (or alternatively, an incremental time period of between 1 hour and about 24 hours or an incremental time period of greater than 24 hours) during the culturing period. For example the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume. The rate at which the second volume of the second liquid culture medium is added (volume/unit of time) can be about the same over the entire or part of the culturing period.

Skilled practitioners will appreciate that the first liquid culture medium and the second liquid culture medium can be the same type of media (e.g., a protein-free culture medium or a serum-free, protein-free chemically-defined medium). In other instances, the first liquid culture medium can be of a type that is different from the second liquid culture medium. The volume of the second liquid culture medium can be added to the first liquid culture medium in an automated fashion, e.g., by perfusion pump.

In some instances, adding to the first liquid culture medium a second volume of the second liquid culture medium does not occur until at least 1 hour after but no more than 7 days after the seeding of the bioreactor with a mammalian cell (e.g., until at least 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours after, but not more than 7 da7s after the seeding of the bioreactor with a mammalian cell). The cell culture medium in fed-batch cultures is typically harvested at the end of culture period, however, the cell culture medium in fed-batch cultures can also be harvested at one or more time points during the culturing period.

Skilled practitioners will appreciate that any of the various parameters for culturing (e.g., bioreactor, volumes, rates or frequencies of replacing culture volumes, agitation, temperatures, culture media, and/or $CO_2$ concentrations) recited herein can be used in any combination in performing these methods.

An additional step of isolating the recombinant glycoprotein can be performed. As is well-known in the art, such methods differ according to the physical properties and activities of the glycoprotein. For example, parameters such as the binding specificity of the glycoprotein (e.g., substrate or antigen-binding activity), net charge, and/or size should be considered when designing the steps for isolating a recombinant glycoprotein (e.g., from culture medium or from a cell). One or more of any of the following methods can be used to isolate a recombinant glycoprotein (e.g., a recombinant glycoprotein produced using any of the methods described herein): affinity column chromatography, ionic (e.g., cationic or anionic) exchange column chromatography, size exclusion column chromatography, reverse-phase column chromatography, filtration, and precipitation. Non-limiting methods for isolating recombinant human α-galactosidase-A protein are described in the Examples.

In some examples, isolating the recombinant glycoprotein from a liquid culture medium can be performed using an integrated, continuous process (e.g., a process including the use of at least two multi-column chromatography systems (MCCSs)). Non-limiting examples of integrated, continuous processes for isolating a recombinant glycoprotein are described in U.S. Provisional Patent Application Nos. 61/775,060 and 61/856,390, and WO 14/137903. Non-limiting examples of integrated and continuous processes for isolating the rhAGA provided herein from a liquid culture medium are described below.

The methods described herein can further include formulating the isolated recombinant glycoprotein into a pharmaceutically acceptable excipient or buffer (e.g., for administration to a subject). These methods can further include sterile filtering, viral inactivation, UV irradiation, and/or lyophilization, or any combination thereof.

Integrated and Continuous Processes for Isolating a rhAGA Protein

A rhAGA provided herein can be isolated using an integrated and continuous process. Methods for isolating a recombinant protein using an integrated and continuous process and details regarding the steps of such processes are known in the art. See WO 14/137903 and U.S. Patent Application Publication No. 2014/0225994. In addition, WO 14/137903 also describes systems and equipment that can be used to perform these integrated and continuous processes.

For example, an integrated and continuous process for isolating a rhAGA protein provided herein can include: (a) providing a liquid culture medium including a rhAGA protein provided herein, that is substantially free of cells, where the liquid culture medium is fed into a first multi-column chromatography system (MCCS1); (b) capturing the rhAGA protein provided herein in the liquid culture medium using the MCCS1, wherein the eluate of the MCCS1 containing the rhAGA protein provided herein is continuously fed into a second multi-column chromatography system (MCCS2); and (c) purifying and polishing the rhAGA protein provided herein using the MCCS2, where the eluate from the MCCS2 is the isolated rhAGA protein provided herein or is a rhAGA protein drug substance, and the process is integrated and runs continuously from said liquid culture medium to the eluate from the MCCS2 that is the isolated rhAGA protein provided herein or the rhAGA protein drug substance.

The MCCS1 and/or MCCS2 can, e.g., perform at least two unit operations. In some embodiments, the MCCS1 or the MCCS2, or both, involve column switching. In some embodiments, the MCCS1 performs the unit operations of capturing the rhAGA protein provided herein and inactivating viruses. In some embodiments, the MCCS2 performs the unit operations of purifying and polishing the rhAGA protein provided herein.

The MCCS1 and/or the MCCS2 can utilize, e.g., at least two chromatography columns. The MCCS1 and/or the MCCS2 can utilize, e.g., at least two chromatographic membranes. The MCCS1 and/or the MCCS2 can utilize, e.g., at least one chromatography column and at least one chromatographic membrane.

The MCCS1 can be, e.g., a periodic counter chromatography system (PCCS1). The PCCS1 can be, e.g., a four-column PCCS. In some embodiments, the four columns in the four-column PCCS can perform the unit operation of capturing the rhAGA protein provided herein from the liquid culture medium. The capturing can be performed using, e.g., affinity chromatography, cation exchange chromatography, anion exchange chromatography, or molecular sieve chromatography. The affinity chromatography can be performed with a capture mechanism selected from, e.g., protein A-binding capture mechanism, substrate-binding capture mechanism, antibody- or antibody-fragment capture mechanism, aptamer-binding capture mechanism, and cofactor-binding mechanism. The eluate containing the rhAGA protein provided herein from the three of the four columns in the four-column PCCS can be fed into the fourth column of the four-column PCCS. The fourth column of the four-column PCCS can perform the unit operation of, e.g., inactivating viruses by holding the eluate containing the rhAGA protein provided herein at a low pH for viral inactivation. For example, the fourth column of the four-column PCCS can hold the eluate containing the rhAGA protein provided herein at a low pH for viral inactivation for a period of about 10 minutes to about 1.5 hours.

In some embodiments, the MCCS2 can be, e.g., a periodic counter current chromatography system (PCCS2). In some examples, the process further includes a step of adjusting the pH of the eluate from the fourth column of the four-column PCCS using an in-line buffer adjustment reservoir before the eluate from the fourth column of the four-column PCCS is fed into the PCCS2.

The PCCS2 can, e.g., include three chromatography columns and a chromatographic membrane. The three chromatography columns in the PCCS2 can perform, e.g., the unit operation of purifying the rhAGA protein provided herein (e.g., through cation or anion exchange chromatography). The eluate from the three columns in the PCCS2 can be fed, e.g., into the chromatography membrane in the PCCS2. The chromatographic membrane in the PCCS2 can, e.g., perform the unit operation of polishing the rhAGA protein provided herein in the eluate of the three chromatography columns in the PCCS2 (e.g., through cation or anion exchange chromatography). The flow through and wash of the chromatographic membrane can be the isolated rhAGA protein provided herein or a rhAGA protein drug substance.

Some examples further include adjusting the ionic concentration of the eluate from the three columns in the PCCS2 using in-line buffer adjustment before the eluate from the three columns in the PCCS2 is fed into the chromatographic membrane in the PCCS2. Some embodiments further include the use of a break tank between the PCCS1 and the PCCS2. Some examples further include filtering the eluate from the PCCS1 before it is fed into the PCCS2. Some embodiments further include filtering the liquid culture medium before it is fed into the MCCS1.

Pharmaceutical Compositions and Kits

Also provided herein are pharmaceutical compositions that include at least one (e.g., one, two, three, or four) of the recombinant human α-galactosidase-A proteins provided herein. Two or more (e.g., two, three, or four) of any of the recombinant human α-galactosidase-A proteins provided herein can be present in a pharmaceutical composition in any combination. Also provided here are pharmaceutical compositions that comprise, consist, or consists essentially of a recombinant human α-galactosidase-A protein provided herein and a pharmaceutically acceptable carrier.

Any of the pharmaceutical compositions provided herein can have no detectable level or no protein, lipid, carbohydrate, nucleic acid, and contaminant (e.g., any of the contaminants described herein) present in an animal product (e.g., an animal serum, an animal plasma, or an animal blood product).

Any of the pharmaceutical compositions provided herein can include a rhAGA protein provided herein that is produced in a cell culture that used only culture media selected from the group of a protein-free, serum-free, and chemically-defined medium. Any of the pharmaceutical compositions provided herein can include a rhAGA protein provided herein that is produced in a cell culture that only used protein-free culture medium and/or chemically-defined culture medium. Any of the pharmaceutical compositions provided herein can include a rhAGA protein provided herein that is produced by a cell culture that used only culture media selected from the group of a protein-free, serum-free, and chemically-defined culture medium, and isolated using an integrated and continuous process (e.g., any of the exemplary integrated and continuous processes described herein or in WO 14/137903).

Any of the pharmaceutical compositions provided herein can have an improved safety profile (e.g., reduced risk of contamination (e.g., any of the exemplary contaminants described herein or known in the art), as compared to a pharmaceutical composition containing a rhAGA protein (e.g., any of the rhAGA proteins provided herein) that is produced by a method that includes the use of a culture medium containing an animal product (e.g., animal serum, animal plasma, or an animal blood factor or protein).

The pharmaceutical compositions may be formulated in any manner known in the art. The pharmaceutical compositions provided herein are advantageous as they have a reduced risk or level of contamination (e.g., a reduced risk or level of viral contamination) and/or have reduced heterogeneity in the glycoforms present in the composition.

Pharmaceutical compositions are formulated to be compatible with their intended route of administration (e.g., intravenous, intraarterial, intramuscular, intradermal, subcutaneous, or intraperitoneal). The compositions can include a pharmaceutically acceptable carrier, e.g., a sterile diluent (e.g., sterile water or saline), a fixed oil, polyethylene glycol, glycerin, propylene glycol, or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfite, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the recombinant human α-galactosidase-A protein can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions that include one or more of any of the recombinant human α-galactosidase-A proteins can be formulated for parenteral (e.g., intravenous, intraarterial, intramuscular, intradermal, subcutaneous, or intraperitoneal) administration in dosage unit form (i.e., physically discrete units containing a predetermined quantity of active protein for ease of administration and uniformity of dosage).

Toxicity and therapeutic efficacy of the compositions can be determined by standard pharmaceutical procedures in cell cultures or experimental animals (e.g., monkeys). One can, for example, determine the $LD_{50}$ (the dose lethal to 50% of the population) and the $ED_{50}$ (the dose therapeutically effective in 50% of the population): the therapeutic index being the ratio of $LD_{50}:ED_{50}$. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given recombinant glycoprotein (e.g., any of the recombinant glycoproteins described herein) for use in a subject (e.g., a human). A therapeutically effective amount of the one or more (e.g., one, two, three, or four) recombinant human α-galactosidase-A proteins (e.g., any of the recombinant human α-galactosidase-A proteins described herein) will be an amount that treats a Fabry disease in a subject (e.g., decreases the risk of developing or prevents the development of Fabry disease in a subject (e.g., a human subject identified as having an increased risk of developing Fabry disease)), decreases the severity, frequency, and/or duration of one or more symptoms of Fabry disease in a subject (e.g., a human) (e.g., as compared to a control subject having the same disease but, e.g., not receiving treatment, receiving a different treatment, or receiving a placebo, or the same subject prior to treatment), decreases the accumulated levels of glycosphingolipids with terminal α-galactosyl residues, such as globotriaoscylceramide in a subject (e.g., a human) having Fabry disease (e.g., as compared to a control subject having the same disease but, e.g., not receiving treatment, receiving a different treatment, or receiving a placebo, or the same subject prior to treatment)). The effectiveness and dosing of any of the recombinant human α-galactosidase-A proteins described herein can be determined by a health care professional or veterinary professional using methods known in the art, as well as by the observation of one or more symptoms of Fabry disease in a subject (e.g., a human). Certain factors may influence the dosage and timing required to effectively treat a subject (e.g., the severity of the disease or disorder, previous treatments, the general health and/or age of the subject, and the presence of other diseases).

Any of the pharmaceutical compositions described herein can further include one or more (e.g., two, three, four, or five) additional therapeutic agents. Non-limiting examples of additional therapeutic agents that can be included in any of the pharmaceutical compositions described herein include: anticonvulsants (e.g., phenytoin, carbamazepine, phenobarbital, methylphenobarbital, barbexaclone, benzodiazepine, clobozan, clonazepam, clorazepate, diazepam, midazolam, lorazepam, nitrazepam, temazepam, nimetazepam, felbamate, carbamazepine, oxcarbazepine, eslicarbazepine acetate, vigabatrin, progabide, tiagabine, topiramate, gabapentin, pregabalin, ethotoin, phenytoin, mephenytoin, fosphenytoin, paramethadione, trimethadione, ethadione, beclamide, primidone, brivaracetam, levetiracetam, seletracetam, ethosuximide, phensuximide, mesuximide, acetazolamide, sultiame, methazolamide, zonisamide, lamotrigine, pheneturide, phenacemide, valpromide, and valnoctamide) and antiemtics (e.g., metoclopramide, prochlorperazine, alizapride, dolasetron, granisetron, ondansetron, tropisetron, palonosetron, mirtazapine, domperidone, olanzapine, droperidol, haloperidol, chlorpromazine, prochlorperazine, aprepitant, and casopitant).

Exemplary doses include milligram or microgram amounts of any of the recombinant human α-galactosidase-A proteins described herein per kilogram of the subject's weight (e.g., about 50 μg/kg to about 3 mg/kg; about 100 μg/kg to about 2.5 mg/kg; about 100 μg/kg to about 2.0 mg/kg; about 500 μg/kg to about 1.5 mg/kg; about 500 μg/kg to about 1.5 mg/kg; or about 800 μg/kg to about 1.2 mg/kg). Exemplary doses may also include milligram or microgram amounts of one or more of any of the one or more additional therapeutic agents described herein per kilogram of the subject's weight (e.g., about 1 μg/kg to about 500 mg/kg; about 100 μg/kg to about 500 mg/kg; about 100 μg/kg to about 50 mg/kg; about 10 μg/kg to about 5 mg/kg; about 10 μg/kg to about 0.5 mg/kg; or about 1 μg/kg to about 50 μg/kg for each administered additional therapeutic agent). While these doses cover a broad range, one of ordinary skill in the art will understand that therapeutic agents, including recombinant α-galactosidase-A protein and the additional therapeutic agents described herein, vary in their potency, and effective amounts can be determined by methods known in the art. Typically, relatively low doses are administered at first, and the attending healthcare professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the recombinant glycoprotein (e.g., recombinant human α-galactosidase-A protein) or the additional therapeutic agents in vivo. The pharmaceutical compositions can be included in a container, pack, or dispenser together with instructions for administration.

For example, one or more recombinant human α-galactosidase-A proteins provided herein can be packaged in a sterile vial as a lyophilized powder or cake, for later reconstitution and administration. The lyophilized powder or cake that includes recombinant human α-galactosidase-A protein can include one or more stabilizing agents (e.g., one or more of mannitol, sodium phosphate monobasic monohydrate, and sodium phosphate dibasic heptahydrate). An example of a lyophilized power or cake that includes recombinant human α-galactosidase-A protein includes: 37 mg of recombinant human α-galactosidase-A protein, 222 mg mannitol, 20.4 mg sodium phosphate monobasic monohydrate, and 59.2 mg sodium phosphate dibasic heptahydrate. Before use or administration of the recombinant human α-galactosidase protein, the lyophilized powder or cake is reconstituted by injection of 7.2 mL sterile water for injection, USP, into the vial, to yield a solution of 5.0 mg of recombinant human α-galactosidase-A protein per mL. This reconstituted solution can further be diluted with 0.9% sodium chloride injection, USP, to a final volume of 500 mL, prior to intravenous administration to the subject at a dose of about 1 mg/kg. Also included are kits that include a vial of a lyophilized recombinant human α-galactosidase cake or powder (as described in this paragraph), instructions for reconstituting the cake or powder (as described in this paragraph), and instructions for biweekly intravenous administration of the reconstituted solution to a subject at a dose of about 1.0 mg/kg.

Another example of a lyophilized power or cake that includes recombinant human α-galactosidase-A protein includes: 5.5 mg of recombinant human α-galactosidase-A protein, 33.0 mg mannitol, 3.0 mg sodium phosphate monobasic monohydrate, and 8.8 mg sodium phosphate dibasic heptahydrate. Before the use or administration of the recombinant human α-galactosidase protein, the lyophilized powder or cake is reconstituted by injection of 1.1 mL sterile water for injection, USP, into the vial, to yield a solution of 5.0 mg of recombinant human α-galactosidase-A protein per mL. This reconstituted solution can further be diluted with 0.9% sodium chloride injection, USP, to a final volume of 500 mL, prior to intravenous administration to the subject at a dose of about 1 mg/kg. Also included are kits that include a vial of a lyophilized recombinant human α-galactosidase cake or powder (as described in this paragraph), instructions for reconstituting the cake or powder (as described in this paragraph), and instructions for biweekly intravenous administration of the reconstituted solution to a subject at a dose of about 1.0 mg/kg.

Also provided herein are kits that include at least one dose of any of the pharmaceutical compositions described herein. In some embodiments, the kits can further include an item for use in administering a pharmaceutical composition (e.g., any of the pharmaceutical compositions described herein) to the mammal (e.g., human) (e.g., a syringe, e.g., a pre-filled syringe). Some examples of the kits include one or more doses (e.g., at least two, three, four, five, six, seven, eight, nine, ten, eleven, twelve, thirteen, fourteen, twenty, thirty, or forty doses) (e.g., intravenous, subcutaneous, or intraperitoneal doses) of any of the pharmaceutical compositions described herein. In some examples, the kit further includes instructions for administering the pharmaceutical composition (or a dose of the pharmaceutical composition) to a mammal (e.g., a human having Fabry disease).

In some embodiments, the kits include a composition including at least one of the recombinant human α-galactosidase-A proteins described herein, and a composition containing at least one additional therapeutic agent (e.g., any combination of one or more of the additional therapeutic agents described herein). In some embodiments, the kit further contains instructions for performing any of the methods described herein.

Fabry Disease

Fabry disease is an X-linked recessive lysosomal storage disease characterized by a deficiency of α-galactosidase-A, known as ceramide trihexosidase, which leads to vascular and other disease manifestations via accumulation of glycosphingolipids with terminal α-galactosyl residues, such as globotriaoscylceramide (GL-3). Non-limiting symptoms of Fabry disease include anhidrosis, painful fingers, left ventricular hypertrophy, renal manifestations, and ischemic strokes. The severity of symptoms varies dramatically (see, Grewal et al., *J. Neurol.* 241:153-156, 1994). A variant with manifestations limited to the heart is recognized, and its incidence may be more prevalent than once believed (see, Nakao, *N. Eng. J. Med.* 333:288-293, 1995). Recognition of unusual variants can be delayed until quite late in life, although diagnosis in childhood is possible with clinical vigilance (Ko et al., *Arch. Pathol. Lab. Med.* 120:86-89, 1996; Mendez et al., *Dement. Geriatr. Cogn. Disord.* 8:252-257, 1997; Shelley et al., *Pediatric Derm.* 12:215-219, 1995). The mean age of diagnosis of Fabry disease is 29 years.

Methods of Treating Fabry Disease, Increasing the Levels of α-Galactosidase in a Lysosome of a Mammalian Cell, and Reducing the Level Globotriaosylceramide in a Subject Also provided herein are methods of treating Fabry disease in a subject (e.g., a human) that include administering to the subject a composition comprising a therapeutically effective amount of at least one of the recombinant human α-galactosidase-A proteins or pharmaceutical compositions described herein. The recombinant human α-galactosidase-A proteins described herein mediate treatment of Fabry disease by increasing the concentration of α-galactosidase-A in a lysosome in a mammalian cell in the subject. Successful treatment of Fabry disease in a subject can be determined by a health professional (e.g., a nurse, a physician, or a physician's assistant). For example, successful treatment can result in a decrease in the number, severity, and/or frequency of one or more symptoms of Fabry disease in a subject (e.g., anhidrosis, painful fingers, left ventricular hypertrophy, renal manifestations, ischemic strokes, and increased levels of globotriaosylceramide in the serum of a subject) (e.g., as compared to a control subject having the same disease but, e.g., not receiving treatment, receiving a different treatment, or receiving a placebo, or the same subject prior to treatment). In addition, successful treatment can be determined by observing a decrease in the level of globotriaosylceramide in the serum or a tissue (e.g., kidney) of a subject over time (e.g., as compared to a subject having Fabry disease receiving a different treatment, receiving a placebo, or receiving no treatment, or as compared to the same subject prior to treatment). Additional methods for determining successful treatment of Fabry disease in a subject are described herein and are known in the art.

Also provided are methods of increasing the levels of α-galactosidase-A protein in a lysosome in a mammalian cell (e.g., a cell in vitro or a cell in a mammal, such as a human) that include contacting the cell with at least one of the recombinant human α-galactosidase-A proteins described herein or at least one of the pharmaceutical compositions described herein in an amount sufficient to increase the levels of α-galactosidase-A protein in a lysosome in the cell. The mammalian cell can be a cell that expresses mannose-6-phosphate receptor. The levels of α-galactosidase-A in a lysosome of a mammalian cell can be determined using immunofluorescence microscopy employing an antibody that specifically binds to human α-galactosidase protein-A. The levels of α-galactosidase-A protein in a lysosome of a mammalian cell can also be determined by isolating lysosomes from a mammalian cell, and determining the levels of α-galactosidase-A protein in the isolated lysosomes, e.g., through the use of an antibody that specifically binds to α-galactosidase-A protein or by performing an α-galactosidase protein-A activity assay using lysate from the isolated lysosomes. An example of an α-galactosidase-A protein assay is an assay that uses 0-nitrophenyl α-D-galactoside as a substrate. In this assay, the 0-nitrophenyl α-D-galactoside is converted to the products of O-nitrophenol and D-galactose. Another example of an assay for detecting α-galactosidase-A protein activity uses a fluorogenic substrate, α-D-galactopyranoside (Shi et al., *Anal. Bioanal. Chem.* 394:1903-1909, 2009). An increase in the level of α-galactosidase-A protein in a lysosome of a cell in a subject (e.g., human) can be indirectly detected by observing a decrease in the number of symptoms of Fabry disease experienced by the subject (e.g., as compared to a control subject having the same disease but, e.g., not receiving treatment, receiving a different treatment, or receiving a placebo, or the same subject prior to treatment), a reduction in the rate of onset of new symptoms of Fabry disease observed in the subject (e.g., as compared to a control subject having the same disease but, e.g., not receiving treatment, receiving a different treatment, or receiving a placebo, or the same subject prior to treatment), a decrease in the severity of one or more symptoms of Fabry disease in the subject (e.g., as compared to a control subject having the same disease but, e.g., not receiving treatment, receiving a different treatment, or receiving a placebo, or the same subject prior to treatment), or a decrease in the worsening of one or more symptoms of Fabry disease in a subject (e.g., as compared to a control subject having the same disease but, e.g., not receiving treatment, receiving a different treatment, or receiving a placebo, or the same subject prior to treatment). Alternatively or in addition, an increase in the level of α-galactosidase-A protein in a lysosome of a cell can, e.g., be detected by observing a decrease in the level of globotriaosylceramide the serum of a subject (e.g., as compared to a control subject having the same disease but, e.g., not receiving treatment, receiving a different treatment, or receiving a placebo, or the same subject prior to treatment). The level of α-galactosidase-A protein in a lysosome in a mammalian cell after treatment with a recombinant protein described herein can be compared to the level of α-galactosidase-A in a lysosome of an untreated mammalian cell (e.g., same type of cell).

Also provided are methods of reducing a level of globotriaosylceramide in the serum or a tissue (e.g., kidney) of a subject (e.g., a human) that include administering at least one of the recombinant human α-galactosidase-A proteins or at least one of the pharmaceutical compositions described herein to the subject. The level of globotriaosylceramide in the serum of the subject can be determined, e.g., using a mass spectrometry (Kim et al., *Korean J. Intern. Med.* 25:415-421, 2010) or an antibody sandwich assay (e.g., the assays described in U.S. Patent Application Publication No. 2012/0178105). The level of globotriaosylceramide in a serum or tissue of a subject following administration of at least one recombinant human α-galactosidase-A protein or pharmaceutical composition provided herein can be compared to the level of globotriaosylceramide in the serum or tissue of a subject having Fabry disease but receiving no treatment or a different treatment, or a level of globotriaosylceramide in the subject prior to the administration of the at least one recombinant human α-galactosidase-A protein or pharmaceutical composition provided herein.

In some embodiments, the subject (e.g., human) has been previously diagnosed or is suspected of having Fabry disease. In some embodiments, the mammal has been identified as having an increased risk of developing Fabry disease (e.g., increased genetic risk of developing Fabry disease). The mammal may be female or male, and may be an adult or juvenile (e.g., an infant or toddler). In some instances, the subject is a human. Where the mammal is a juvenile, he or she may be between 1 day and 18 years old, inclusive (e.g., between 1 day and 17 years old, between 1 day and 16 years old, between 1 day and 15 years old, between 1 day and 14 years old, between 1 day and 13 years old, between 1 day and 12 years old, between 1 day and 11 years old, between 1 day and 10 years old, between 1 day and 9 years old, between 1 day and 8 years old, between 1 day and 7 years old, between 1 day and 6 years old, between 1 day and 5 years old, between 1 day and 4 years old, between 1 day and 3 years old, between 1 day and 2 years old, between 1 day and 1 year old, between 1 day and 6 months old, between 6 months and 4 years old, between 1 month and 5 years old, between 3 years and 13 years old, or between 13 years and 18 years old). Where the mammal is an adult, the mammal may be, e.g., between 18 to 20 years old, inclusive, or at least or about 20, 25, 30, 35, 40, 45, 50, 55, 60, 65, 70, 75, 80, 85, 90, 95, or at least or about 100 years old.

A subject can be diagnosed as having Fabry disease by a healthcare professional by observation of one or more symptoms in the subject (e.g., one or more of any of the symptoms of Fabry disease described herein or known in the art). In some examples, the subject may already be receiving a treatment for Fabry disease. In others, the prior treatment for Fabry disease has been unsuccessful.

The recombinant proteins or pharmaceutical compositions described herein may be administered by intravenous, intraarterial, subcutaneous, intraperitoneal, interlymphatic, intramuscular, ocular, or intrathecal administration. Further, the recombinant proteins and pharmaceutical compositions can be formulated using any art-known techniques and/or as described herein (e.g., formulated for subcutaneous, intravenous, intraarterial, interlymphatic, intramuscular, perimuscular, or intrathecal administration, and/or formulated in a liposome or nanoparticle).

Recombinant human α-galactosidase-A proteins or pharmaceutical compositions described herein can be administered by a medical (e.g., a physician, a physician's assistant, a nurse, a nurse's assistant, or a laboratory technician) or veterinary professional. Alternatively or in addition, the recombinant protein or pharmaceutical composition can be self-administered by a human, e.g., the patient her/himself. Administration can occur, e.g., in a hospital, a clinic, or a primary care facility (e.g., a nursing home), or any combination thereof.

In some embodiments, the mammal is administered a dose of between 1 mg to 400 mg of any of the recombinant human α-galactosidase-A proteins described herein or any of the pharmaceutical compositions described herein (e.g., between 1 mg to 300 mg, between 1 mg to 250 mg, between 1 mg and 200 mg, between 1 mg and 150 mg, between 1 mg and 100 mg, between 1 mg and 80 mg, between 1 mg and 70 mg, between 1 mg and 60 mg, between 1 mg and 50 mg, between 1 mg and 40 mg, between 1 mg and 30 mg, between 1 mg and 20 mg, between 1 mg and 10 mg, between 20 mg and 120 mg, between 30 mg and 90 mg, or between 40 mg and 80 mg). In some examples, the subject is administered a dose of recombinant human α-galactosidase-A protein of about 0.1 mg/kg to about 4.0 mg/kg (e.g., between about 0.1 mg/kg and about 3.5 mg/kg, between about 0.1 mg/kg and about 3.0 mg/kg, between about 0.1 mg/kg and about 2.5 mg/kg, between about 0.1 mg/kg and about 2.0 mg/kg, between about 0.1 mg/kg and about 1.5 mg/kg, between about 0.5 mg/kg and about 1.5 mg/kg, or between about 0.7 mg/kg and about 1.3 mg/kg).

In some embodiments, the subject is further administered an additional therapeutic agent (e.g., any of the additional therapeutic agents described herein). The additional therapeutic agent can be administered to the subject at substantially the same time as the recombinant protein or pharmaceutical composition is administered and/or at one or more other time points. In some embodiments, the additional therapeutic agent is formulated together with the at least one recombinant human α-galactosidase-A protein (e.g., using any of the examples of formulations and compositions described herein).

In some embodiments, the additional therapeutic agent is formulated in a first dosage form, and the at least one recombinant human α-galactosidase-A protein is formulated in a second dosage form. Where the additional therapeutic agent is formulated in a first dosage form, and the at least one recombinant human α-galactosidase-A protein is formulated in a second dosage form, the first dosage form and the second dosage form can be formulated, e.g., for the same route of administration (e.g., oral, subcutaneous, intramuscular, intravenous, intaarterial, intrathecal, interlymphatic, or intraperitoneal administration) or for different routes of administration (e.g., the first dosage form formulated for oral administration and the second dosage form formulated for subcutaneous, intravenous, intraarterial, or intramuscular administration administration). Combinations of such treatment regimes are clearly contemplated in the present invention.

As described above, the amount of the at least one recombinant human α-galactosidase-A protein (and optionally, an additional therapeutic agent) administered will depend on whether the administration is local (e.g., intramuscular) or systemic. In some embodiments, the subject (e.g., human) is administered more than one dose of the at least one recombinant human α-galactosidase-A protein or the at least one pharmaceutical composition. In some embodiments, the subject (e.g., human) is administered more than one dose (e.g., two or more doses) of any of the compositions described herein. In some embodiments, the subject is administered a dose of the at least one recombinant human α-galactosidase-A protein or the at least one pharmaceutical composition at least once a month (e.g., at least twice a month, at least three times a month, at least four times a month, at least once a week, at least twice a week, three times a week, once a day, or twice a day). For example, a subject can be administered two or more doses of any of the pharmaceutical compositions or one or more of the recombinant human α-galactosidase-A proteins at a frequency of at least one dose every two months (e.g., at least one dose every month, at least one dose a week, at least one dose every two weeks, or at least one dose a day).

The recombinant human α-galactosidase-A protein or pharmaceutical composition may be administered to a subject chronically. Chronic treatments include any form of repeated administration for an extended period of time, such as repeated administrations for one or more months, between a month and a year, one or more years, more than five years, more than 10 years, more than 15 years, more than 20 years, more than 25 years, more than 30 years, more than 35 years, more than 40 years, more than 45 years, or longer. Alternatively or in addition, chronic treatments may be administered. Chronic treatments can involve regular administrations, for example one or more times a day, one or more times a week, or one or more times a month. For example, chronic treatment can include administration (e.g., intravenous administration) about every two weeks (e.g., between about every 10 to 18 days). A suitable dose may be the amount of the recombinant human α-galactosidase-A protein that is the lowest dose effective to produce a desired therapeutic effect. Such an effective dose will generally depend upon the factors described herein. If desired, an effective daily dose of the recombinant human α-galactosidase-A protein or the pharmaceutical composition can be administered as two, three, four, five, or six or more subdoses administered separately at appropriate intervals throughout the day, optionally, in unit dosage forms.

The recombinant human α-galactosidase-A protein or the pharmaceutical composition may be formulated for sustained-release (e.g., formulated in a biodegradable polymer or a nanoparticle), and may in some instances be administered directly into muscle tissue, subcutaneous tissue, or the peritoneal cavity in a subject (intramuscular, intraperitoneal, or subcutaneous depot administration, respectively). Alternatively or in addition, the sustained-release formulation may be administered systemically (e.g., oral, intravenous, intaarterial, intraperitoneal, interlymphatic, or subcutaneous administration). In some instances, the recombinant human α-galactosidase-A protein or pharmaceutical composition may be formulated for oral, intraglandular, periglandular, subcutaneous, interductal, intramuscular, perimuscular, intraperitoneal, intramuscular, intraarterial, transdermal, interlymphatic, or intravenous administration.

EXAMPLES

The invention is further described in the following examples, which do not limit the scope of the invention described in the claims.

Example 1

Production of a Recombinant Cell Line for Producing Glycoproteins

Experiments were performed to develop a cell line useful for the recombinant production of glycoproteins. In these experiments, a starting serum-dependent CHO cell line (DXB11) was serially: grown in tissue culture medium that includes 5% fetal bovine serum for three days, grown in tissue culture medium that includes 2.5% fetal bovine serum for three days, and grown in tissue culture medium that includes no fetal bovine serum for eight days. At the end of this culturing period, the resulting CHO cell culture was diluted and aliquoted to generate serum-free sub-population, or pool, suspension cultures. After expansion and growth assessments, serum-free pools were aliquoted to generate single-cell clone cultures. Each single-cell clone was tested for its cell growth in serum-free culture medium, and a subset of clones was then tested for transfection efficiency by electroporation of an expression vector encoding red fluorescent protein (RFP) under control of the hamster β-actin promoter, with RFP expression analyzed by flow cytometry at 2 days post-transfection. Clones meeting the criteria for doubling time (<35 hours) and transfection efficiency (>30% RFP positive with >75% culture viability) were evaluated for recombinant protein expression following stable transfection with an expression vector(s) encoding a gene(s) of interest under control of the hamster β-actin promoter and encoding the DHFR gene under the control of the SV40 promoter. After transfection, stably transfected pools were selected using methotrexate (MTX) and after selection, pools were assessed for recombinant protein productivity by seeding cells into unfed batch cultures and analyzing clarified media harvests for levels of the recombinant protein. Based on MTX selection survival and recombinant protein production levels of the stably transfected pools, a lead serum-free parental clone was identified.

The lead parental clone was sub-cloned and further cultured in protein-free, animal derived component (ADC)-free, and chemically defined medium (CD DG44 medium from Invitrogen), and sub-clones were banked. Approximately 27 cell generations in ADC-free media elapsed from the single cell sub-cloning step to the initial frozen cell bank. The single cell clones were tested for the following: transfection efficiency (by electroporation with the RFP encoding vector described above), cell growth properties (in CD DG44 medium from Invitrogen), and stable transformations to produce recombinant proteins. Evaluation of the stably transfected pools (using CD CHO medium from Invitrogen) included assessments of MTX selection, peak cell density, growth properties, and volumetric productivity rate (VPR). Recombinant protein productivity was tested as described above.

A single clonal parental cell line, after all of the culturing steps described above, was identified as having the best transfection efficiency and best MTX selection, peak cell densities, cell growth properties, and volumetric productivity rate (VPR) of stably transfected pools. This parental cell line was propagated and frozen into aliquots for use in future experiments.

Example 2

Production of Recombinant Human α-Galactosidase-A

A vial of cells producing (and secreting) recombinant human α-galactosidase-A protein was thawed into a chemically defined and animal-derived component (ADC)-free cell culture medium in shake flasks. The mixture was propagated until a sufficient amount of cells were available to seed perfusion bioreactors. The culture was allowed to grow until a target high viable cell density was reached, at which point cell density control was initiated. Continuous perfusion was started one day after inoculation and then incrementally ramped up to a fixed perfusion rate at the targeted high cell density in the perfusion bioreactor. The clarified harvest fluid (containing recombinant human α-galactosidase-A protein) was directly loaded onto a capture column using an integrated continuous capture chromatography system. The captured eluate (containing recombinant human α-galactosidase-A protein) was then further purified through anion exchange chromatography resin (ANX) to remove DNA, host cell protein, and other impurities. The ANX eluate (containing recombinant human α-galactosidase-A protein) was further purified through immobilized metal affinity chromatography resin. The metal affinity chromatography eluate (containing recombinant human α-galactosidase-A protein) was concentrated to a target recombinant human α-galactosidase-A protein concentration, and then buffer exchanged into a drug substance buffer using a tangential flow filtration membrane. The recombinant human α-galactosidase-A protein drug substance was then subjected to analytical characterization (as described in the Examples). In preparation for the animal PK/PD study (Example 5), the recombinant human α-galactosidase-A protein drug substance was subsequently formulated by adding mannitol and then filtered through 0.22 cm$^2$ absolute filter.

Example 3

Physical Characterization of Recombinant Human α-Galactosidase-A

The recombinant human α-galactosidase-A protein produced and purified in Example 2 was physically characterized using a variety of biophysical techniques, and compared to Fabrazyme® and Replagal®. Each of the studied structural and functional features of recombinant human α-galactosidase-A protein is discussed below, along with the methods used to determine each structural and functional feature.

Molecular Size

The molecular size of Fabrazyme®, Replagal®, and the recombinant human α-galactosidase-A protein provided herein (FZ2G) was assessed using size-exclusion chromatography, MALDI-TOF MS, and gel electrophoresis.

SEC

Size exclusion chromatography (SEC) analysis was performed using an Agilent 1200 HPLC using a TSK-Gel G3000SWXL column (Tosoh, 7.8 mm×30 cm). Fifty µL of sample was injected and column chromatography was performed at a flowrate of 0.5 mL/minute. The eluted proteins were detected at 280 nm.

MALDI-TOF MS

MALDI-TOF MS was performed by first diluting the samples (1:5) in 0.1% aqueous formic acid. BSA was diluted to 2 mg/mL in 0.1% aqueous formic acid. Diluted samples were spotted in triplicate onto a stainless steel MALDI target with saturated sinapinic acid in aqueous 0.1% TFA, 50% acetonitrile at a ratio of 1 µL/1 µL. Ten spectra were generated from each spot at various sites and with varying laser intensity and then averaged. The instrument settings are listed in Table 1. The spectra were calibrated to the singly and doubly charged m/z peaks of BSA. The raw data were smoothed using the default smoothing routine at a peak resolution of 200. The peak values from the triplicate measurements were averaged, and the standard deviation was determined.

TABLE 1

Instrument Parameters for Fabrazyme MALDI-MS Analysis

| Parameter | Value |
| --- | --- |
| Ionization mode | linear, positive |
| Control mode | Manual |
| Accelerating voltage | 25000 V |
| Grid voltage | 88% |
| Delay time | 750 nsec |
| Shots/spectrum | 30 |
| Mass range | 19,999-90,000 |
| Low mass gate | 2000 |

SDS-Page

Ten µgs of each sample was loaded onto a 4-20% Tris Glycine gel (Invitrogen) in sample loading buffer with dithiolthreitol (DTT). A voltage of 150 was applied to the gel for 1 hour and 25 minutes. Upon completion, the gel was stained with Coomassie R-250 staining solution for 30 minutes. Excess stain was removed using a de-staining solution for 30 minutes.

Results

Figure 6:
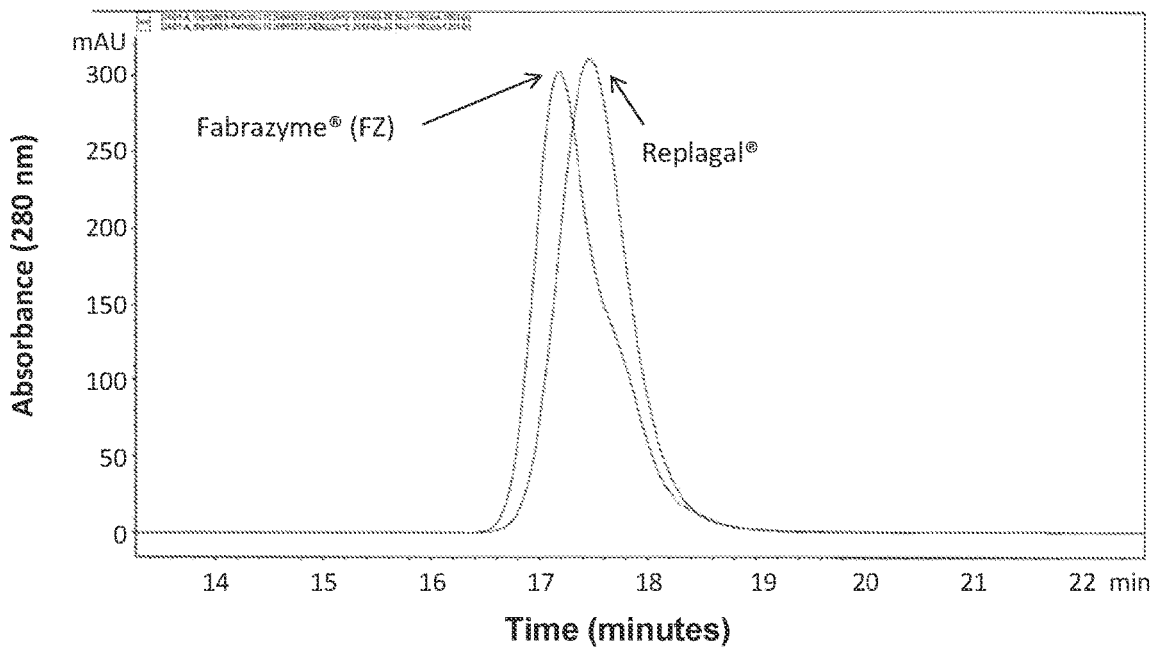
FIG. 6 is a chromatogram showing the elution of Fabrazyme® and Replagal® from a size exclusion column.
Figure 7A:
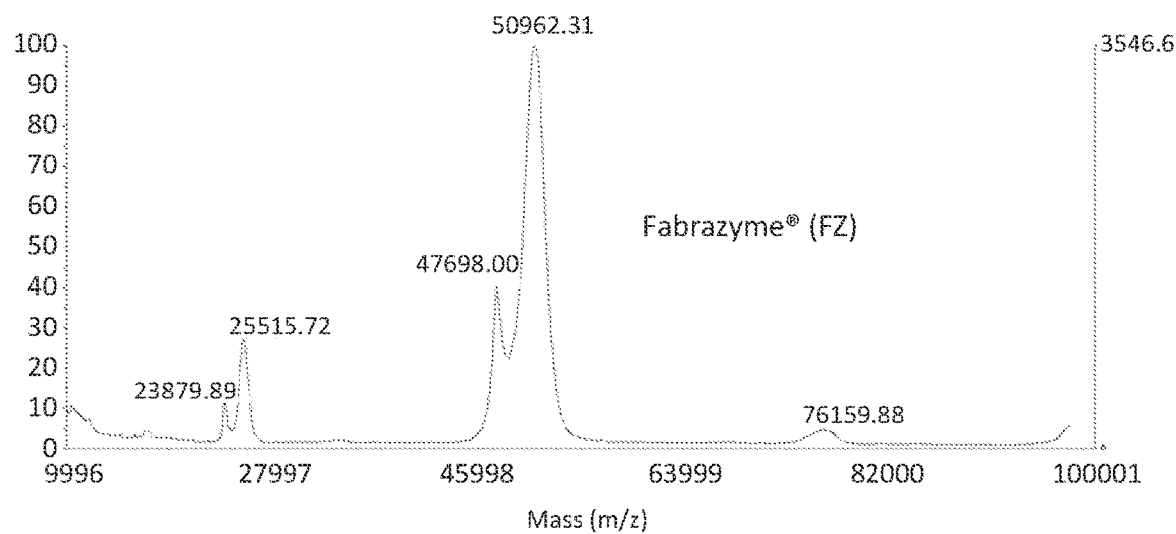
FIG. 7A is a mass-to-charge matrix-assisted laser desorption/ionization time-of-flight mass spectrometry (MALDI-TOF MS) profile of Fabrazyme®.
Figure 7B:
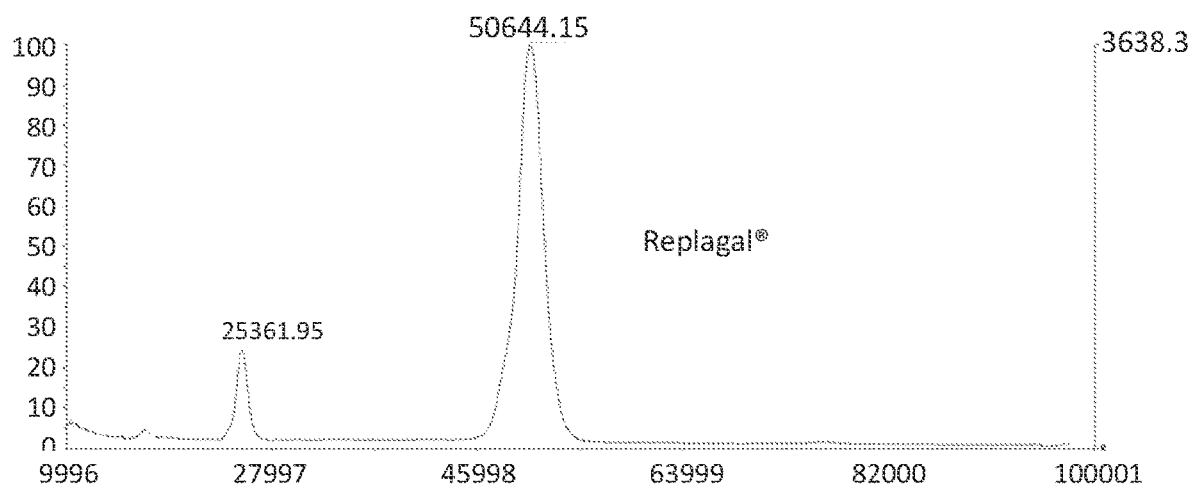
FIG. 7B is a MALTI-TOF MS mass spectrometry profile of Replagal®.
Figure 8:
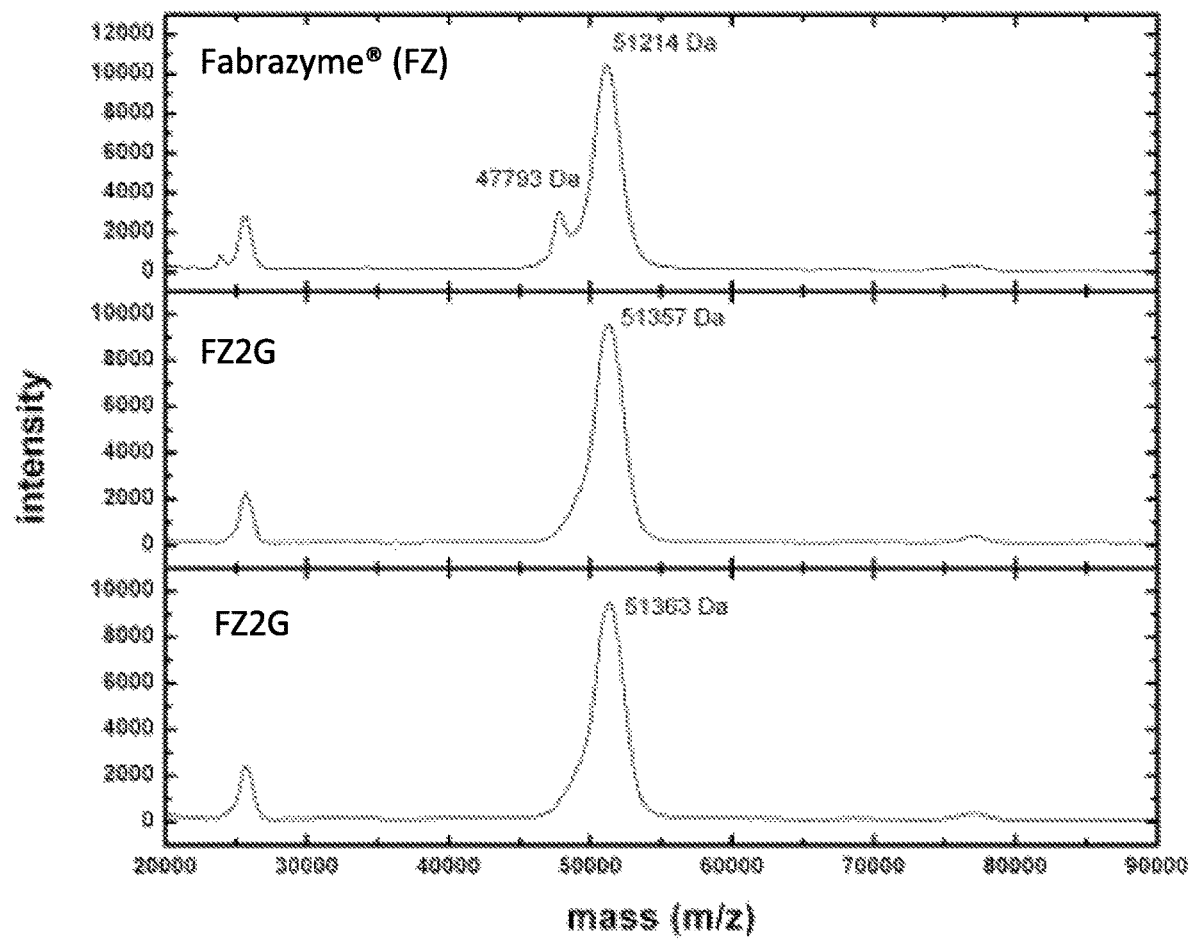
FIG. 8 is a set of three mass-to-charge MALDI-TOF mass spectrometry profiles of Fabrazyme® (top) and recombinant human α-galactosidase-A protein provided herein (FZ2G) (middle and bottom).
Figure 9:
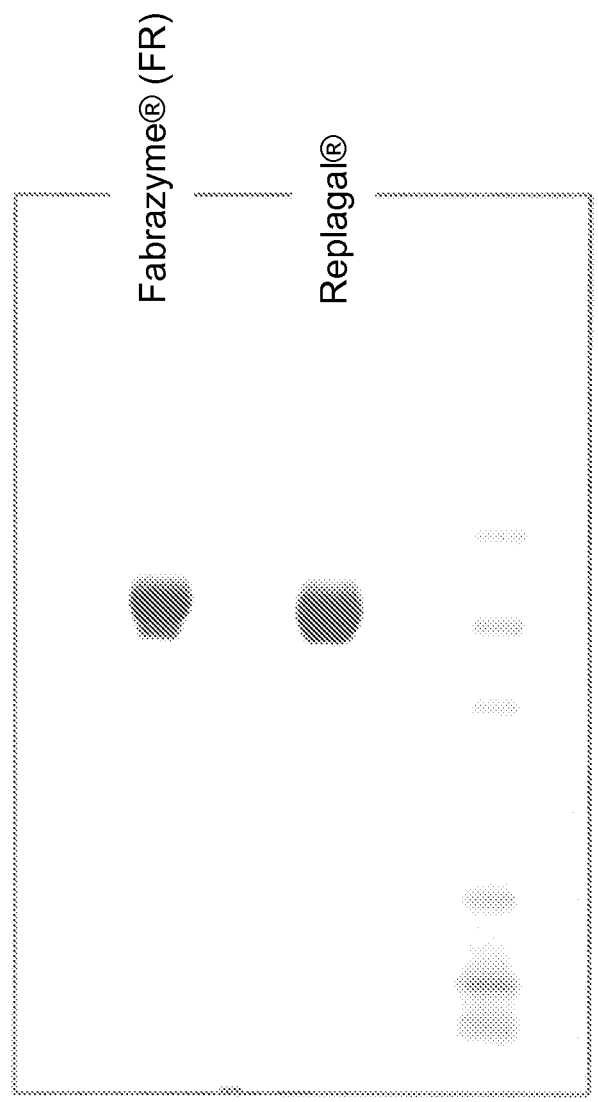
FIG. 9 is a picture of a sodium-dodecyl sulfate polyacrylamide gel of Fabrazyme® and Replagal®.

Size exclusion chromatography (SEC) analysis shows that Fabrazyme® elutes earlier and with a trailing shoulder compared to Replagal® (FIG. 6). These results suggest that Fabrazyme® is heterogeneous and may have a higher molecular weight compared to Replagal®. The MALDI-TOF MS spectra in FIGS. 7A-7B show that the m/z ratio of the major species observed in Fabrazyme® and Replagal® are comparable. Fabrazyme® also contains lower molecular weight species of recombinat human α-galactosidase-A not observed in Replagal®. The MALDI-TOF MS spectra in FIG. 8 show that the m/z ratio of the major species observed in Fabrazyme® and FZ2G are comparable. Fabrazyme® contains a lower molecular weight species not observed in FZ2G MALDI-TOF MS spectra. The SDS-PAGE mobility of the Fabrazyme® and Replagal® are comparable. A minor species with higher mobility (lower apparent molecular weight) is observed in Fabrazyme®, but not in Replagal® (FIG. 9).

Glycosylation Profile

The N-linked glycosylation profiles of Fabrazyme®, Replagal®, and FZ2G were determined using 2-antrhanilic acid (AA)-derivatization and normal phase liquid chromatography with fluorescence detection, as generally described in Kamoda et al., *J. Chromatography A* 1133:332-339, 2006).

Site-Specific Glycan Analysis

Site-specific glycosylation analysis of Fabrazyme®, Replagal®, and FZ2G was performed using a hybrid linear ion trap-Orbitrap mass spectrometer (LTQ-Orbitrap, Thermo Fisher Scientific) coupled with liquid chromatography system (nanoAcquity LC, Waters). In this procedure, enzymatic digests were prepared by first reducing 100 µg of protein with dithiolthreitol then alkylating with iodoacetic acid. Samples were subsequently exchanged into Tris-C1, pH 8.0, using Biospin30 columns (Bio-Rad), followed by an 18-hour digestion with endoproteinase Lys-C and 2-hour digestion with trypsin. Following dilution with formic acid to quench the digestion, 200 ng of each sample digest was injected onto 75 µm×10 cm C-18 column (Picofrit, New Objectives). The peptides were eluted in a stepped gradient of 2-95% acetonitrile in 0.1% formic acid. The m/z range was scanned from 325-1800 by FTMS at 60,000 resolution with top 5 intensity data dependent CID scans. The MS data were integrated and processed using RefinerMS V 7.6 software (Genedata) for quantitation, and CID spectra were collected for confirmation of glycoform composition.

Results

Figure 11:
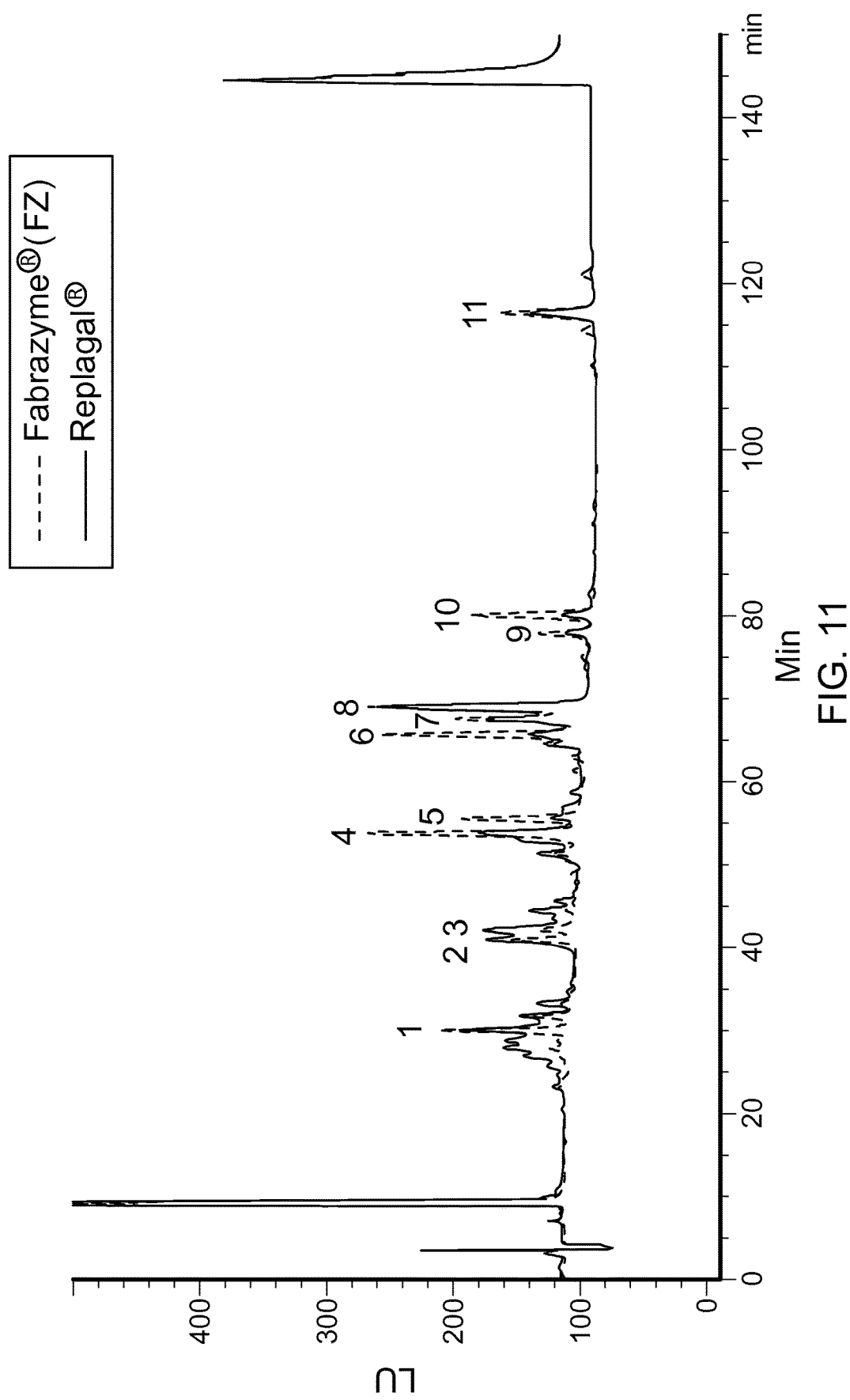
FIG. 11 is a chromatographic elution profile of AA-labeled N-linked oligosaccharides from Fabrazyme® (blue) and Replagal® (red).
Figure 12:
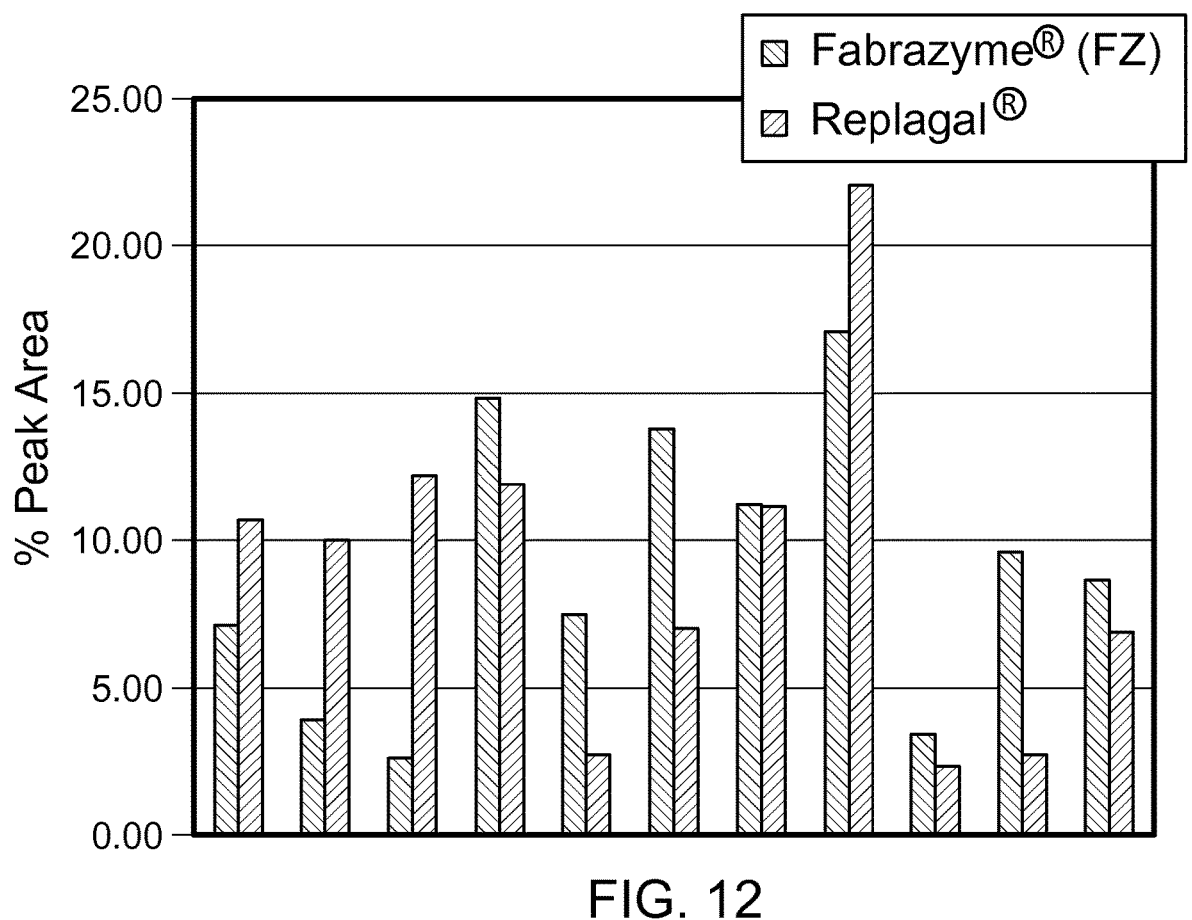
FIG. 12 is a graph showing the percentage of total N-linked oligosaccharides that are neutrally-charged oligosaccharides (peak 1), monosialylated fucose-containing oligosaccharides (peak 2), monosialylated oligosaccharides (peak 3), bisialylated fucose-containing oligosaccharides (peak 4), bisialylated oligosaccharides (peak 5), triantennary, trisialylated oligosaccharides (form 1; peak 6), triantennary, trisialylated oligosaccharides (form 2; peak 6'), mannose-6-phosphate oligosaccharides (peak 7), monophosphorylated oligosaccharides (peak 8), tetrasialylated oligosaccharides (peak 9), monosialylated and monophosphorylated oligosaccharides (peak 10), and bis-mannose-6-phosphate oligosaccharides (peak 11) (left to right) in Fabrazyme® (left bar in each set of two bars) and Replagal® (right bar in each set of two bars).
Figure 13:
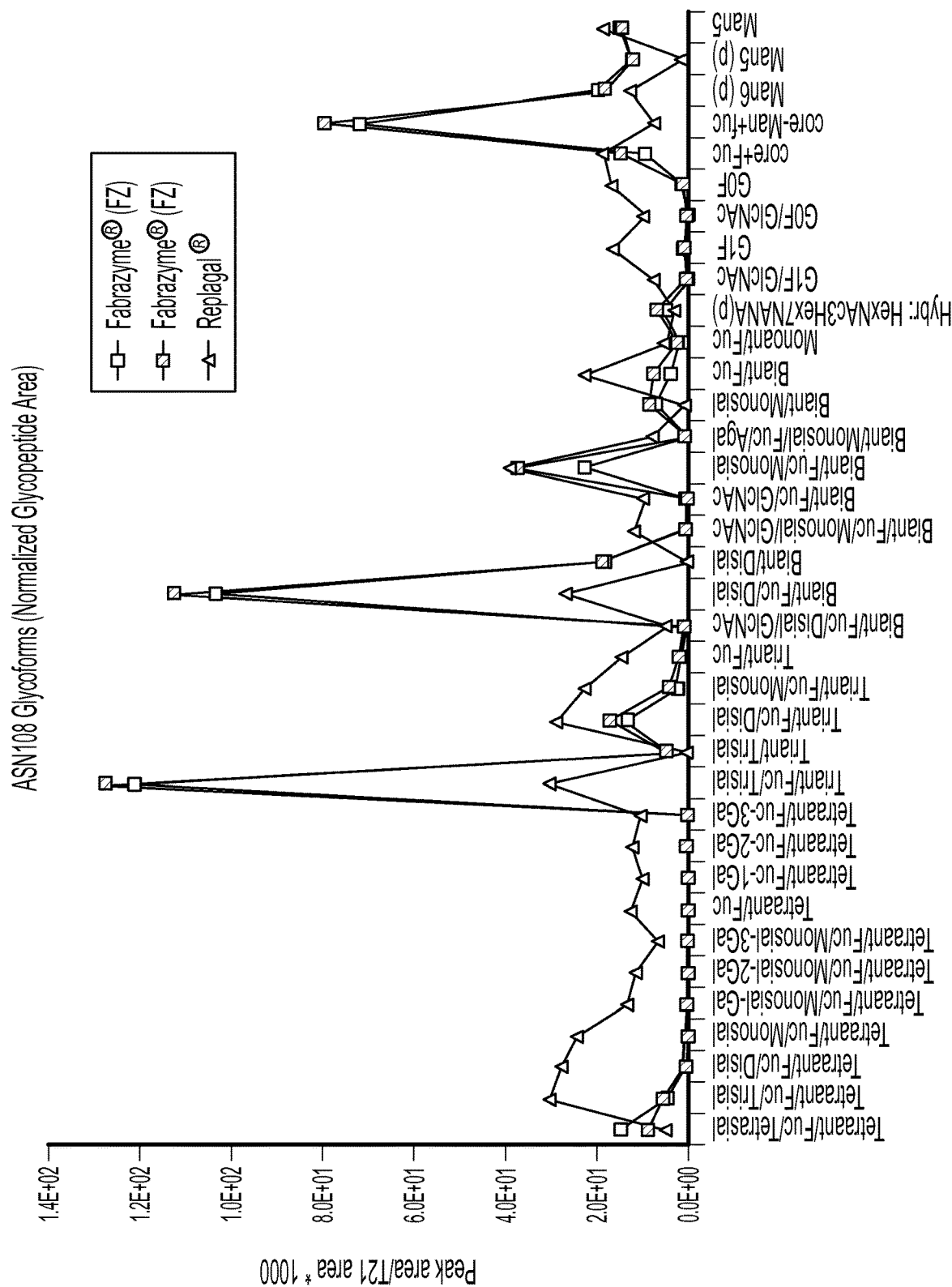
FIG. 13 is a graph showing the distribution of N-linked oligosaccharides present at the amino acid residue of Asn108 in Fabrazyme® and Replagal®, as determined by LCMS analysis of each enzymatically digested protein.
Figure 14:
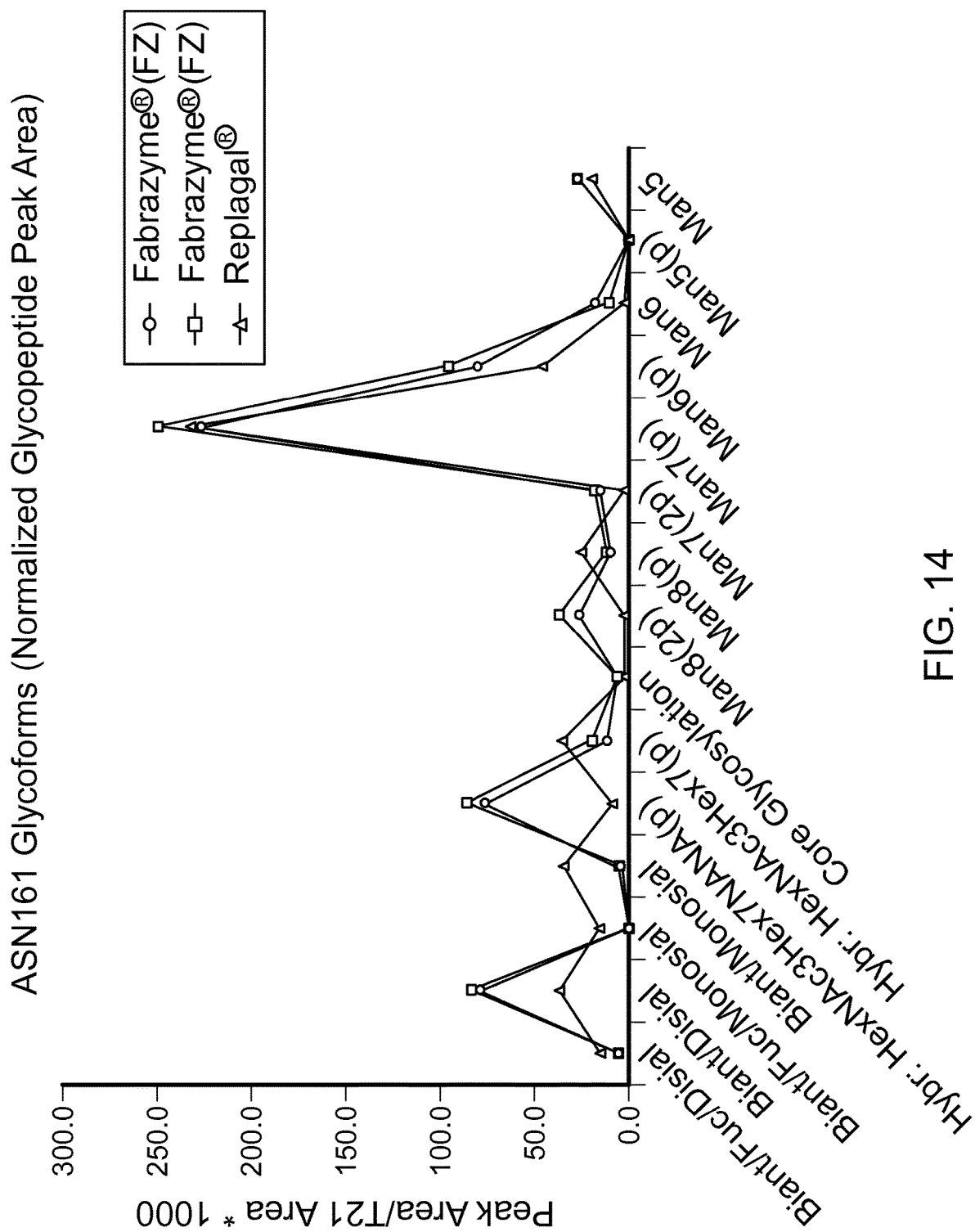
FIG. 14 is a graph showing the distribution of N-linked oligosaccharides present at the amino acid residue of Asn161 in Fabrazyme® and Replagal®, as determined by LCMS analysis of each enzymatically digested protein.
Figure 15:
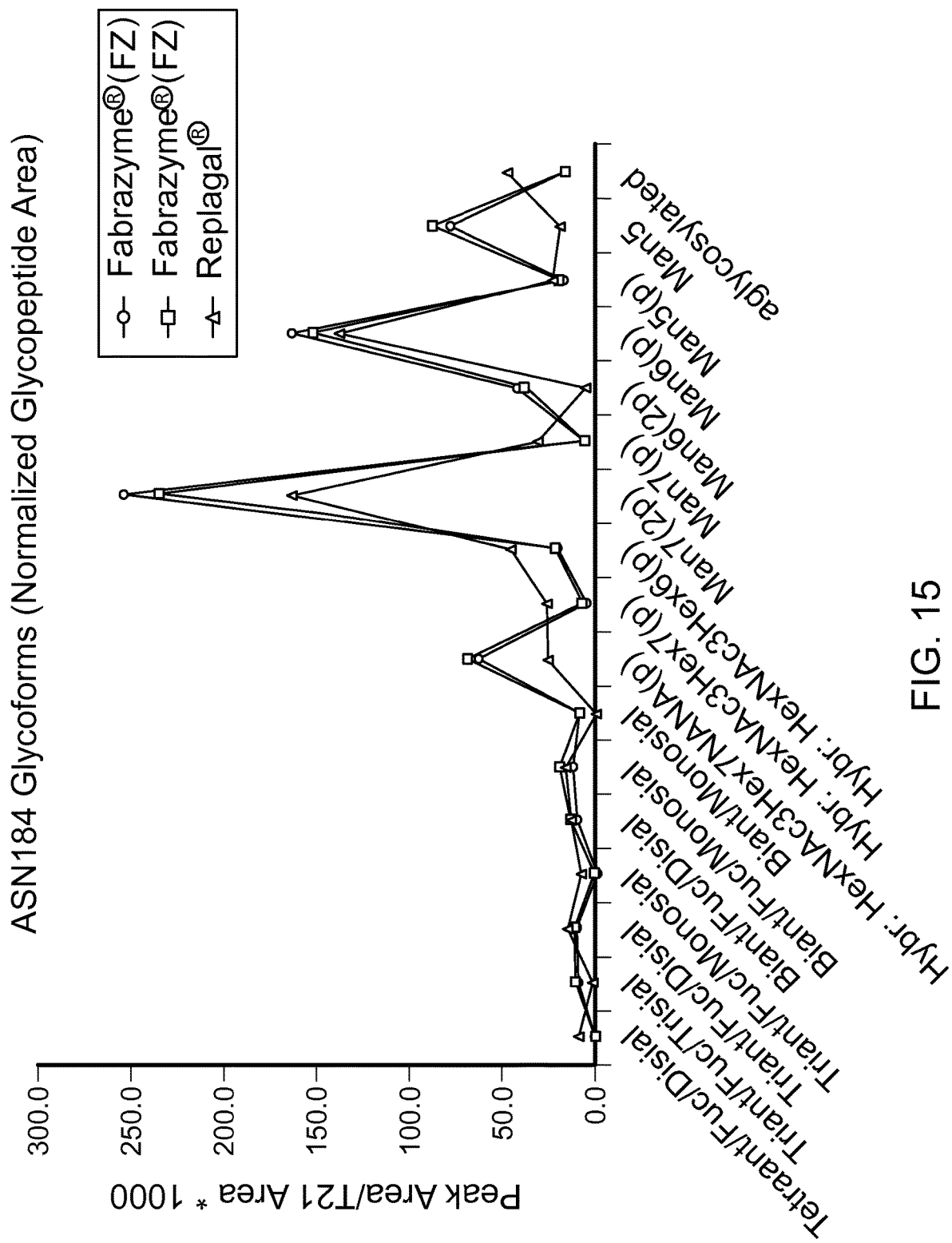
FIG. 15 is a graph showing the distribution of N-linked oligosaccharides present at the amino acid residue of Asn184 in Fabrazyme® and Replagal®, as determined by LCMS analysis of each enzymatically digested protein.
Figure 16:
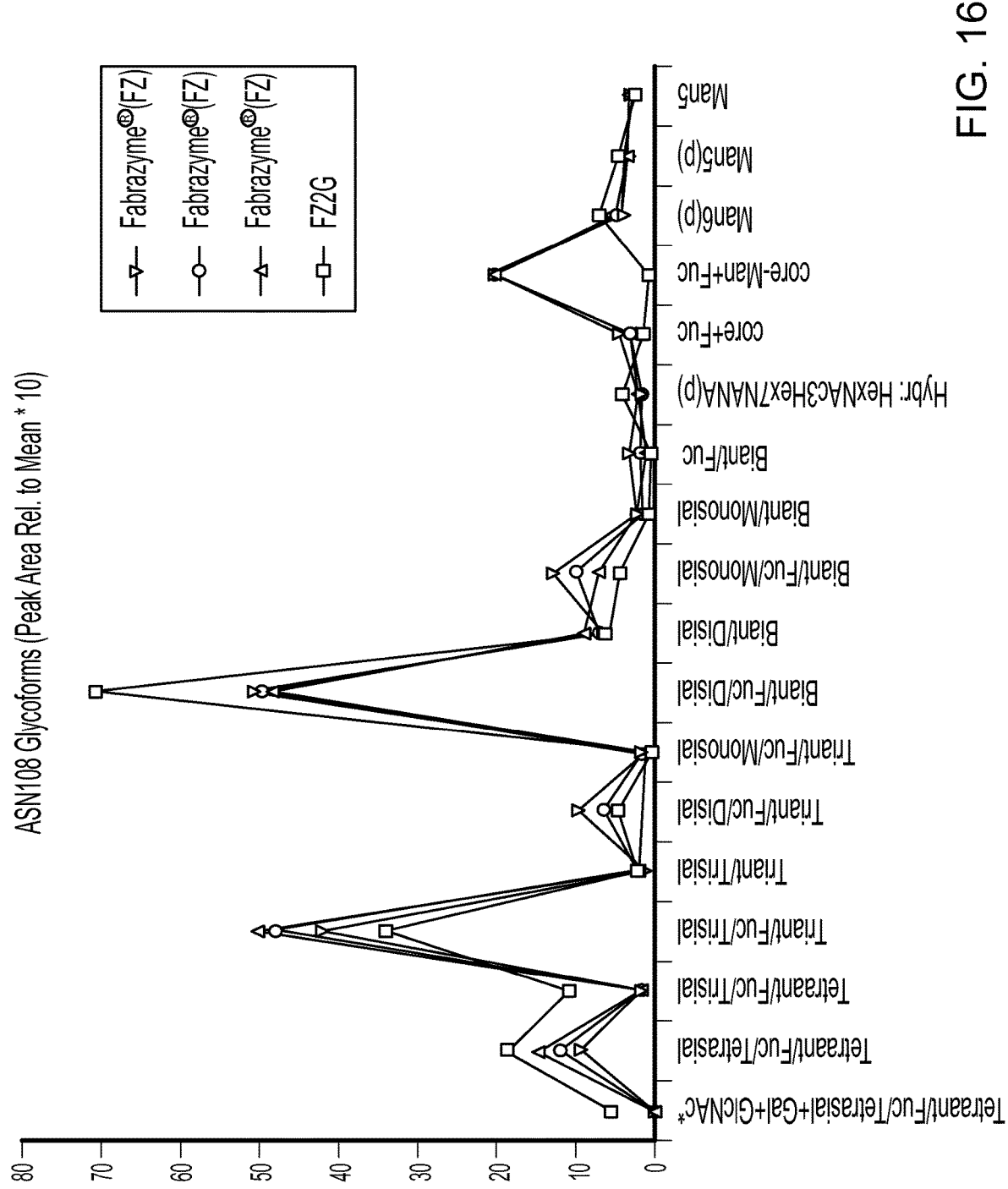
FIG. 16 is a graph showing the distribution of N-linked oligosaccharides present at the amino acid residue of Asn108 in Fabrazyme® and FZ2G, as determined by LCMS analysis of each enzymatically digested protein.
Figure 17:
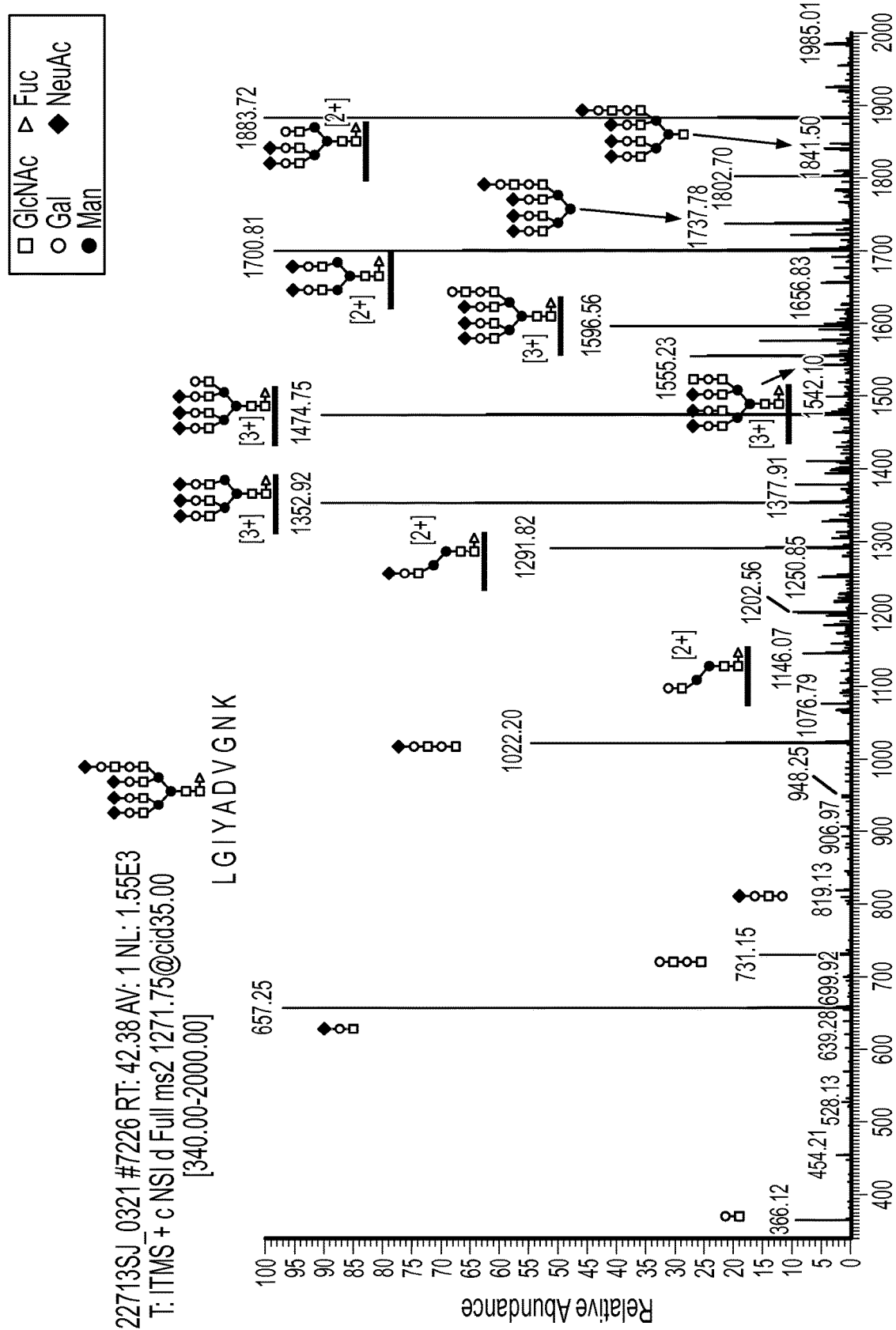
FIG. 17 is an exemplary graph showing the structure of the N-linked oligosaccharides present in each peak following LCMS analysis of the N-linked oligosaccharides present at the amino acid residue of Asn108 in Fabrazyme® and FZ2G.
Figure 18:
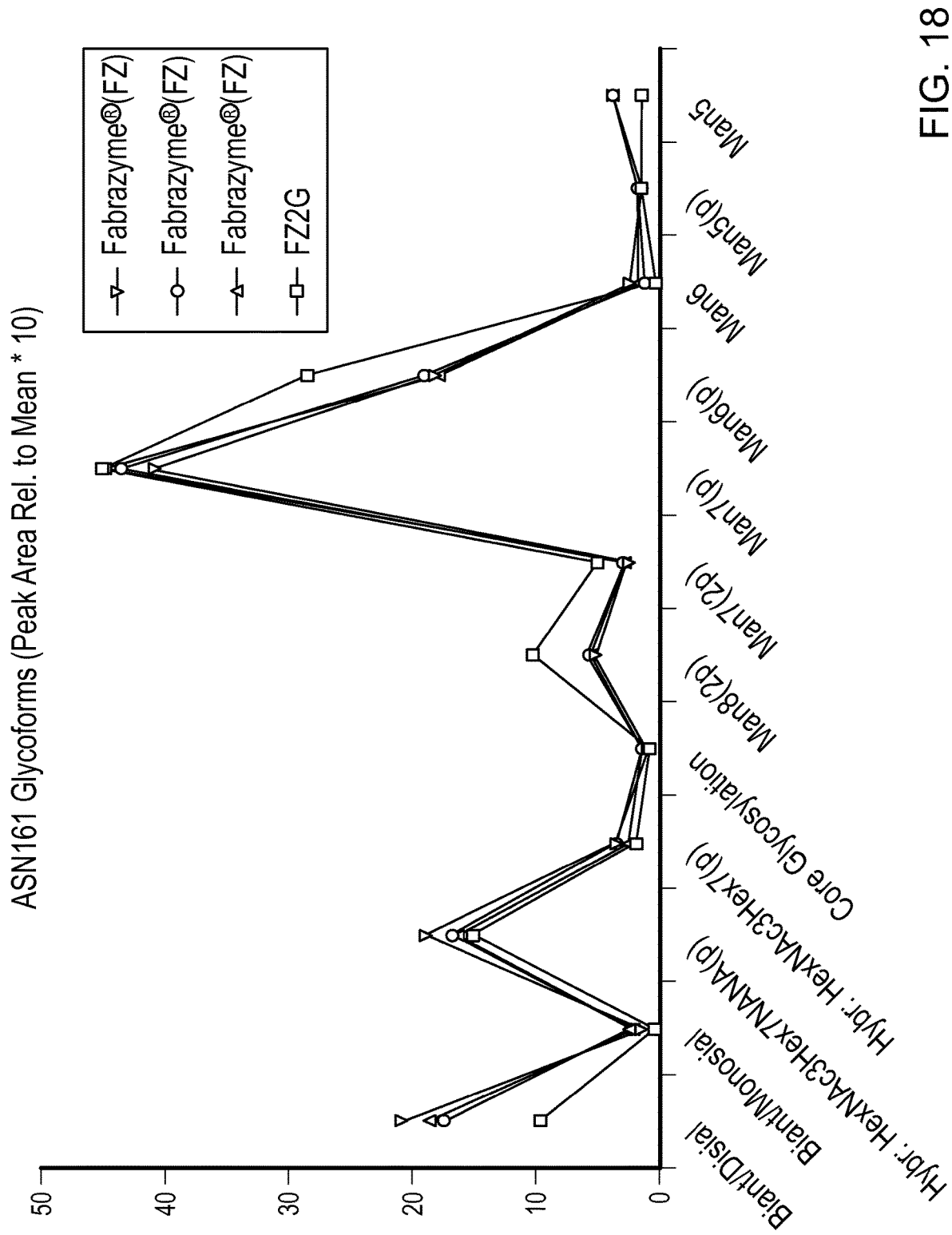
FIG. 18 is a graph showing the distribution of N-linked oligosaccharides present at the amino acid residue of Asn161 in Fabrazyme® and FZ2G, as determined by LCMS analysis of each enzymatically digested protein.
Figure 19:
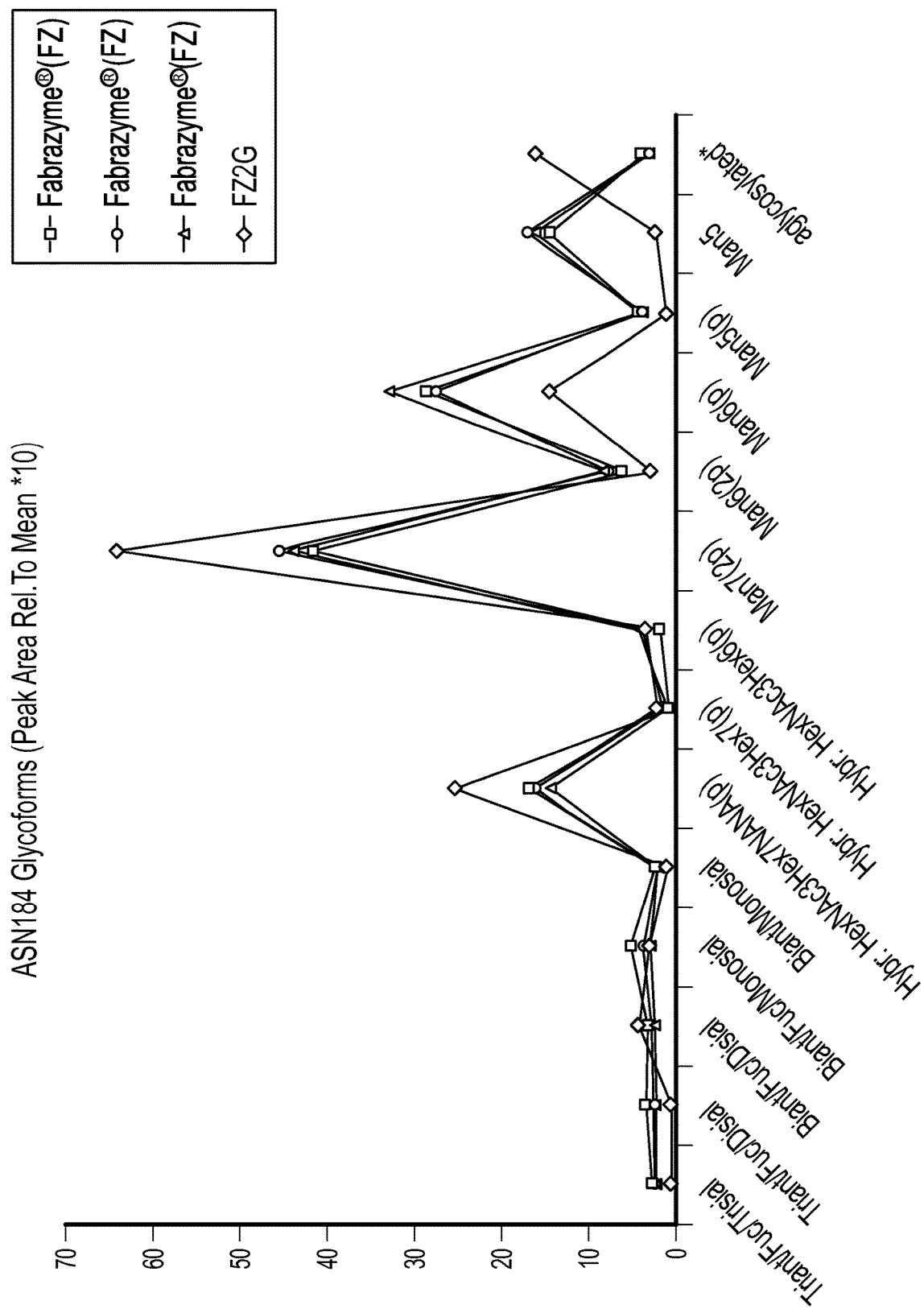
FIG. 19 is a graph showing the distribution of N-linked oligosaccharides present at the amino acid residue of Asn184 in Fabrazyme® and FZ2G, as determined by LCMS analysis of each enzymatically digested protein.

FIG. 10 shows a typical chromatogram of Fabrazyme® AA-derivatized N-linked oligosaccharides, showing the specific type of N-linked oligosaccharide present in each of the peaks. The identities of the glycan species observed in the AA-labeled glycan profiles were determined by LCMS analysis. The chromatograms showing the elution of the different types of AA-derivatized N-linked oligosaccharides in Fabrazyme® and Replagal® are shown in FIG. 11. The percentage of total N-linked oligosaccharides that correspond to each type of N-linked oligosaccharide for Fabrazyme® and Replagal® are shown in FIG. 12. The relative percentage of each glycan species observed at Asn108, Asn161, and Asn184 of Fabrazyme® and Replagal® are shown in FIGS. 13, 14, and 15, respectively. The relative percentage of each glycan species observed at Asn108, Asn161, and Asn184 of Fabrazyme® and FZ2G are shown in FIGS. 16 and 17, 18, and 19, respectively.

Figure 20:
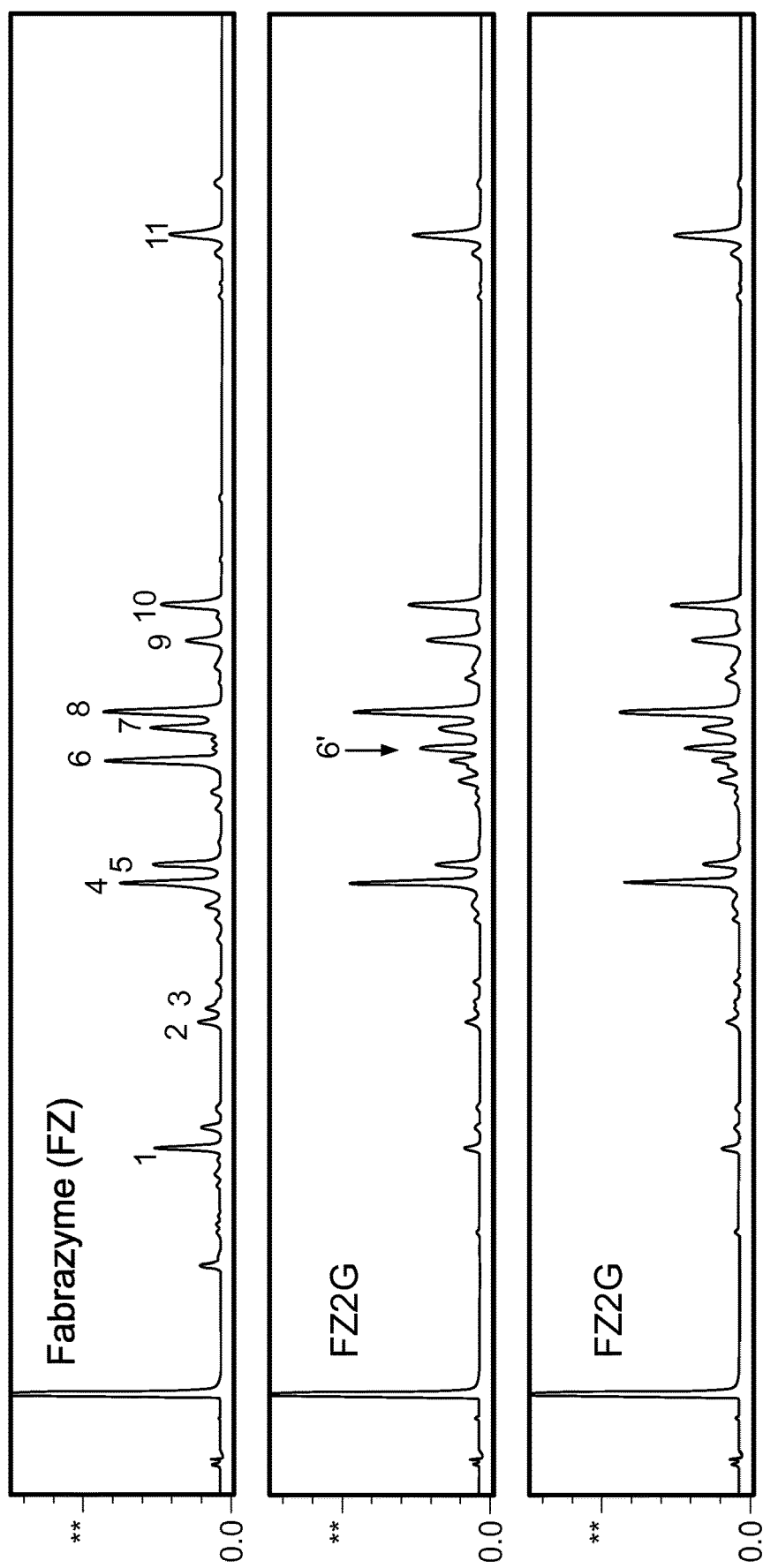
FIG. 20 is a chromatographic elution profile of AA-labeled N-linked oligosaccharides from Fabrazyme® and recombinant human α-galactosidase-A protein provided herein (FZ2G).
Figure 21:
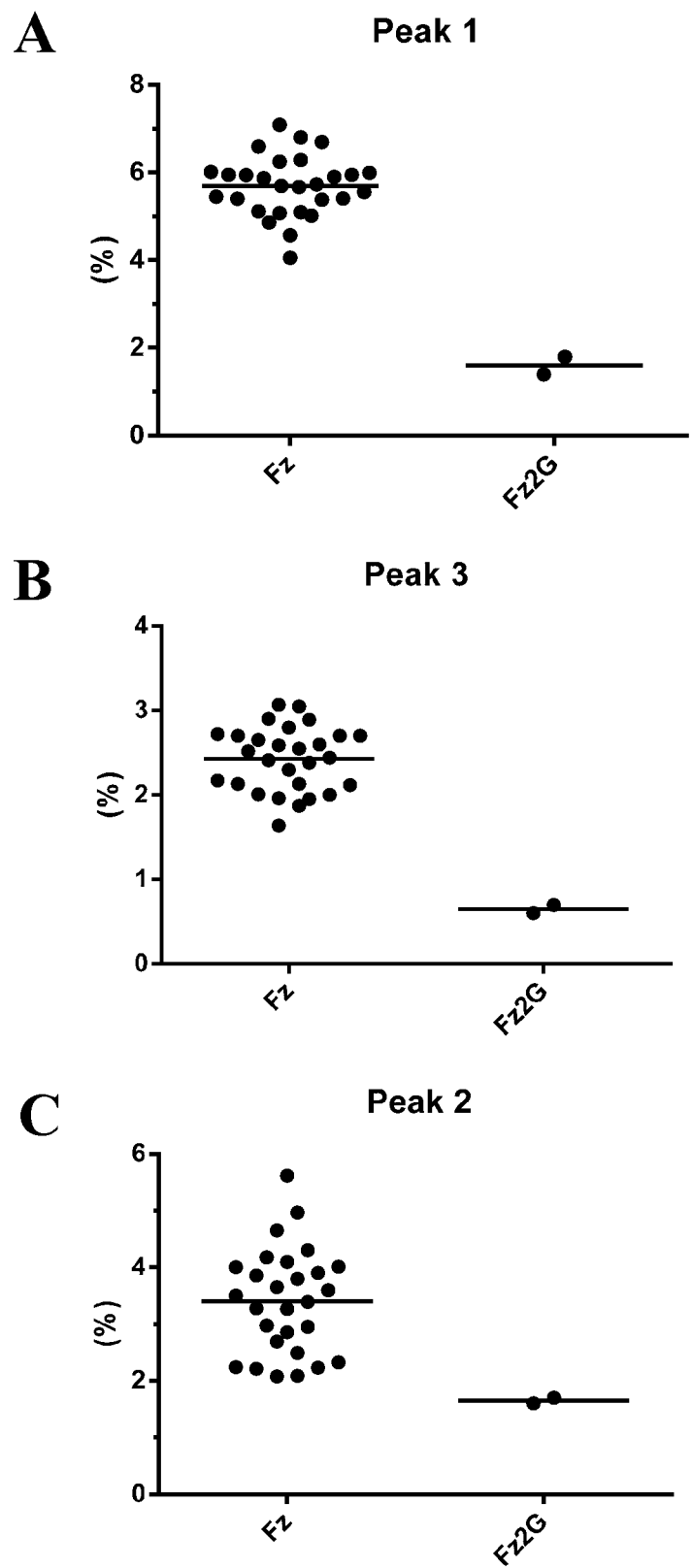
FIG. 21A is a graph showing the percentage of total N-linked oligosaccharides that are neutrally-charged oligosaccharides (peak 1) in Fabrazyme® and in recombinant human α-galactosidase-A protein provided herein (FZ2G), as determined by chromatographic analysis of AA-labeled N-linked oligosaccharides.
FIG. 21B is a graph showing the percentage of total N-linked oligosaccharides that are monosialylated, minus fucose oligosaccharides in Fabrazyme® and in recombinant human α-galactosidase-A protein provided herein (FZ2G), as determined by chromatographic analysis of AA-labeled N-linked oligosaccharides.
FIG. 21C is a graph showing the percentage of total N-linked oligosaccharides that are monosialylated fucose-containing oligosaccharides (peak 2) in Fabrazyme® (FZ) and in recombinant human α-galactosidase-A protein provided herein (FZ2G), as determined by chromatographic analysis of AA-labeled N-linked oligosaccharides.
Figure 22:
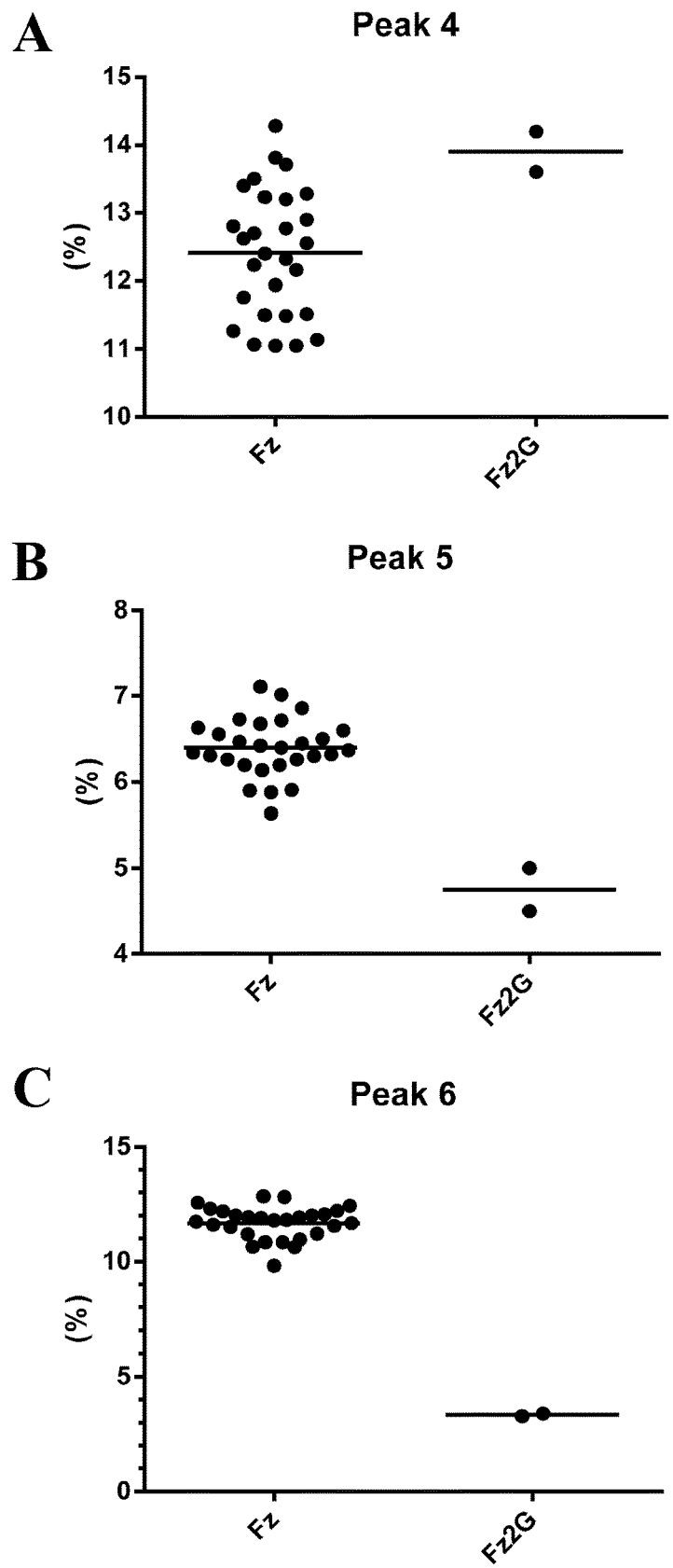
FIG. 22A is a graph showing the percentage of total N-linked oligosaccharides that are bisialylated fucose-containing oligosaccharides (peak 4) in Fabrazyme® (FZ) and in recombinant human α-galactosidase-A protein provided herein (FZ2G), as determined by chromatographic analysis of AA-labeled N-linked oligosaccharides.
FIG. 22B is a graph showing the percentage of total N-linked oligosaccharides that are bisialylated oligosaccharides (peak 5) in Fabrayzme® (FZ) and in recombinant human α-galactosidase-A protein provided herein (FZ2G), as determined by chromatographic analysis of AA-labeled N-linked oligosaccharides.
FIG. 22C is a graph showing the percentage of total N-linked oligosaccharides that are triantennary, trisialylated oligosaccharides (form 1; peak 6) in Fabrazyme® (FZ) and in recombinant human α-galactosidase-A protein provided herein (FZ2G), as determined by chromatographic analysis of AA-labeled N-linked oligosaccharides.
Figure 23:
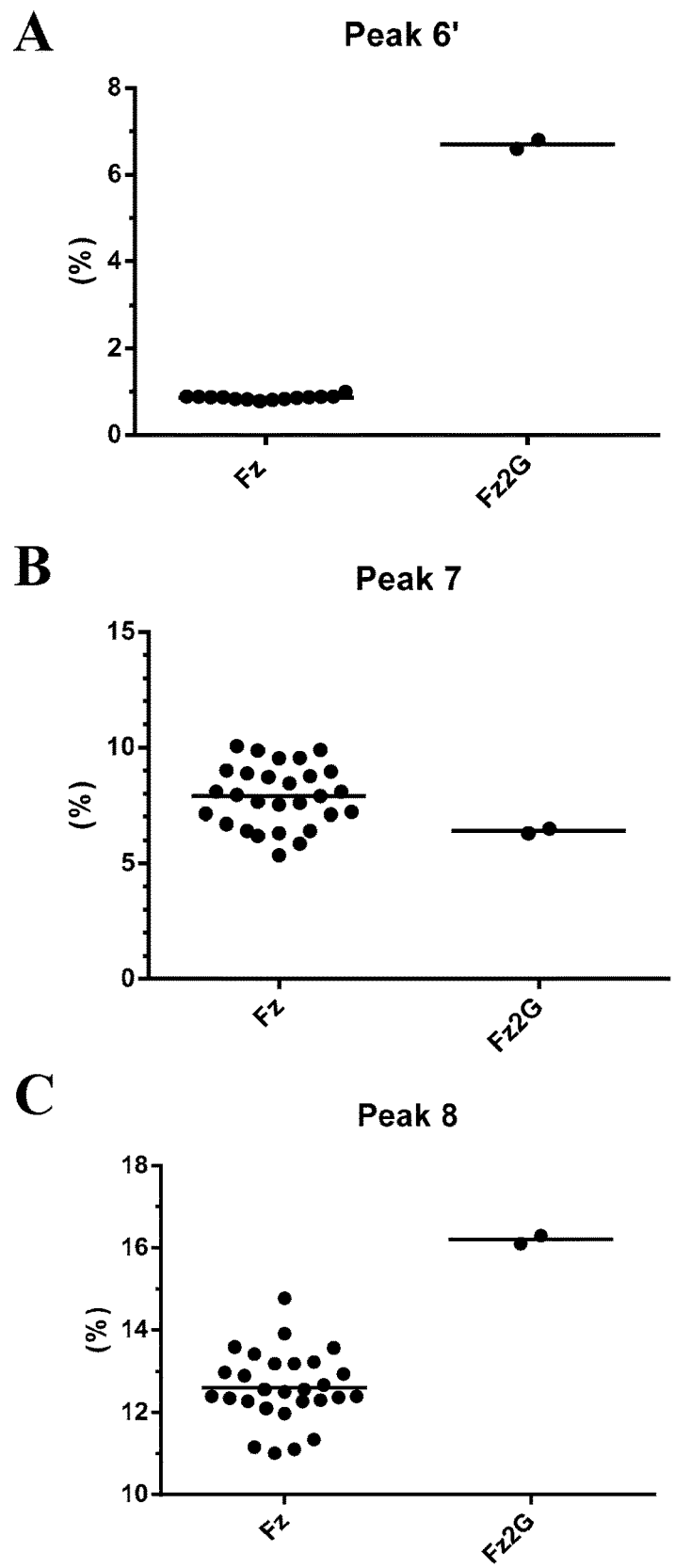
FIG. 23A is a graph showing the percentage of total N-linked oligosaccharides that are triantennary, trisialylated oligosaccharides (form 2; peak 6') in Fabrazyme® (FZ) and in recombinant human α-galactosidase-A protein provided herein (FZ2G), as determined by chromatographic analysis of AA-labeled N-linked oligosaccharides.
FIG. 23B is a graph showing the percentage of total N-linked oligosaccharides that are mannose-6-phosphate oligosaccharides (peak 7) in Fabrazyme® (FZ) and in recombinant human α-galactosidase-A protein provided herein (FZ2G), as determined by chromatographic analysis of AA-labeled N-linked oligosaccharides.
FIG. 23C is a graph showing the percentage of total N-linked oligosaccharides that are monophosphorylated oligosaccharides (peak 8) in Fabrazyme® (FZ) and in recombinant human α-galactosidase-A protein provided herein (FZ2G), as determined by chromatographic analysis of AA-labeled N-linked oligosaccharides.
Figure 24:
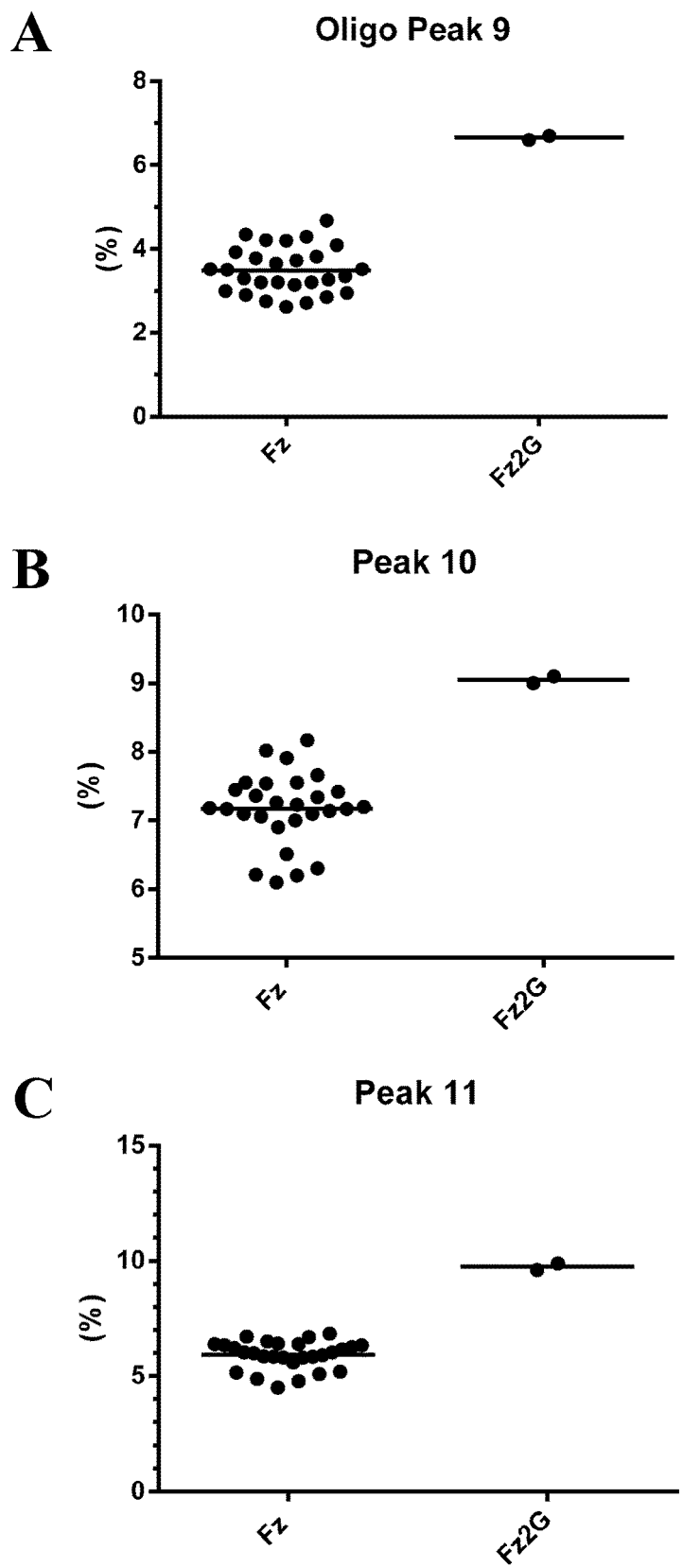
FIG. 24A is a graph showing the percentage of total N-linked oligosaccharides that are tetrasialylated oligosaccharides (peak 9) in Fabrazyme® (FZ) and in recombinant human α-galactosidase-A protein provided herein (FZ2G), as determined by chromatographic analysis of AA-labeled N-linked oligosaccharides.
FIG. 24B is a graph showing the percentage of total N-linked oligosaccharides that are monosialylated and monophosphorylated oligosaccharides (peak 10) in Fabrazyme® (FZ) and in recombinant human α-galactosidase-A protein provided herein (FZ2G), as determined by chromatographic analysis of AA-labeled N-linked oligosaccharides.
FIG. 24C is a graph showing the percentage of total N-linked oligosaccharides that are bis-mannose-6-phosphate oligosaccharides (peak 11) in Fabrazyme® (FZ) and in recombinant human α-galactosidase-A protein provided herein (FZ2G), as determined by chromatographic analysis of AA-labeled N-linked oligosaccharides.

The AA-labeled profiles of Fabrazyme® and FZ2G are shown in FIG. 20. The percentage of total N-linked oligosaccharides that correspond to neutrally-charged oligosaccharides (peak 1), monosialylated fucose-containing oligosaccharides (peak 2), and monosialylated oligosaccharides (peak 3) in the Fabrazyme® and FZ2G are shown in FIGS. 21A-C. The percentage of total N-linked oligosaccharides that correspond to bisialylated fucose-containing oligosaccharides (peak 4), bisialylated oligosaccharides (peak 5), and triantennary, trisialylated oligosaccharides of form 1 (peak 6) in Fabrazyme® and in FZ2G are shown in FIGS. 22A-C. The percentage of total N-linked oligosaccharides that correspond to triantennary, trisialylated oligosaccharides of form 2 (peak 6'), mannose-6-phosphate oligosaccharides (peak 7), and monophosphorylated oligosaccharides (peak 8) in Fabrazyme® and in FZ2G are shown in FIGS. 23A-C. The percentage of total N-linked oligosaccharides that correspond to tetrasialylated oligosaccharides (peak 9), monosialylated or monophosphorylated oligosaccharides (peak 10), and bis-mannose-6-phosphate oligosaccharides (peak 11) in Fabrazyme® and in FZ2G are shown in FIGS. 24A-C.

These data reveal that the presently provided recombinant human α-galactosidase-A protein (FZ2G) has a substantially different glycosylation pattern as compared to Fabrazyme®. For example, the recombinant human α-galactosidase-A proteins provided herein (FZ2G) have: a percentage of total N-linked oligosaccharides that are neutrally-charged oligosaccharides (peak 1) that is less than the Fabrazyme®; a percentage of total N-linked oligosaccharides that are monosialylated fucose-containing oligosaccharides (peak 2) that is less than Fabrazyme®; a percentage of total N-linked oligosaccharides that are mannose-6-phosphate oligosaccharides (peak 7) that is about the same or less than Fabrazyme®; a percentage of total N-linked oligosaccharides that are monophosphorylated oligosaccharides (peak 8) that is greater than Fabrazyme®; a percentage of total N-linked oligosaccharides that are tetrasialylated oligosaccharides (peak 9) that is greater than Fabrazyme®; a percentage of total N-linked oligosaccharides that are monosialylated and monophosphorylated (peak 10) that is greater than Fabrazyme®; and a percentage of total N-linked oligosaccharides that are bis-mannose-6-phosphate oligosaccharides (peak 11) that is greater than Fabrazyme®. The altered glycosylation pattern of the recombinant human α-galactosidase-A proteins described herein (FZ2G) (e.g., as compared to Fabrazyme®) provide for several advantages, for example, one or more of: a decrease in the non-specific targeting of recombinant human α-galactosidase-A protein to the liver (by decreased binding to the asialoglycoprotein receptor expressed on the surface of hepatocytes following administration of the recombinant human α-galactosidase-A protein to a subject, e.g., a human subject), increased rate of endocytosis of the recombinant human α-galactosidase-A protein by a mammalian cell (e.g., a human cell) expressing mannose-6-phosphate receptor protein on its surface, increased affinity to mannose-6-phosphate receptor protein, and increased serum half-life, as compared to Fabrazyme®.

Ratios of Mannose-6-Phosphate and N-Acetylneuraminic Acid to Protein

An additional set of experiments were performed to determine the molar ratio of mannose-6-phosphate to protein and the molar ratio of N-acetylneuraminic acid to protein in recombinant human α-galactosidase-A protein provided herein (FZ2G) and Fabrazyme®.

Figure 25:
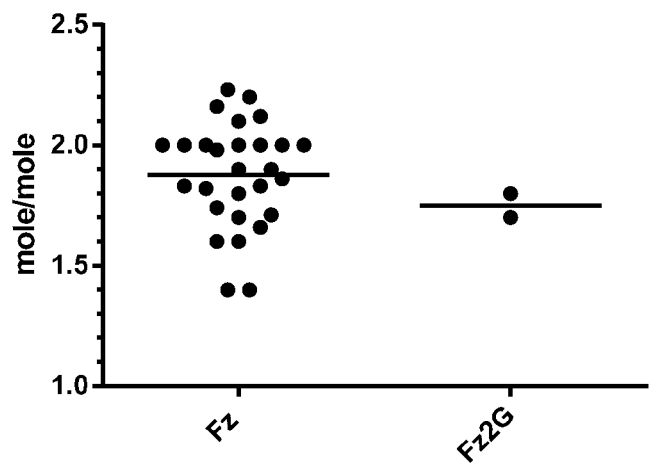
FIG. 25A is a graph showing the mole-to-mole ratio of mannose-6-phosphate to protein (top) of Fabrazyme® (FZ) and recombinant human α-galactosidase-A protein provided herein (FZ2G).
FIG. 25B is graph showing the mole-to-mole ratio of N-acetylneuraminic acid (NANA) to protein of Fabrazyme® (FZ) and recombinant human α-galactosidase-A protein provided herein (FZ2G).

The data show that the recombinant human α-galactosidase-A protein provided herein (FZ2G) has a molar ratio of mannose-6-phosphate to protein that is about the same as Fabrazyme® and an elevated molar ratio of N-acetylneuraminic acid to protein compared to Fabrazyme® (FIGS. 25A-B).

Isoelectric Point

Figure 31:
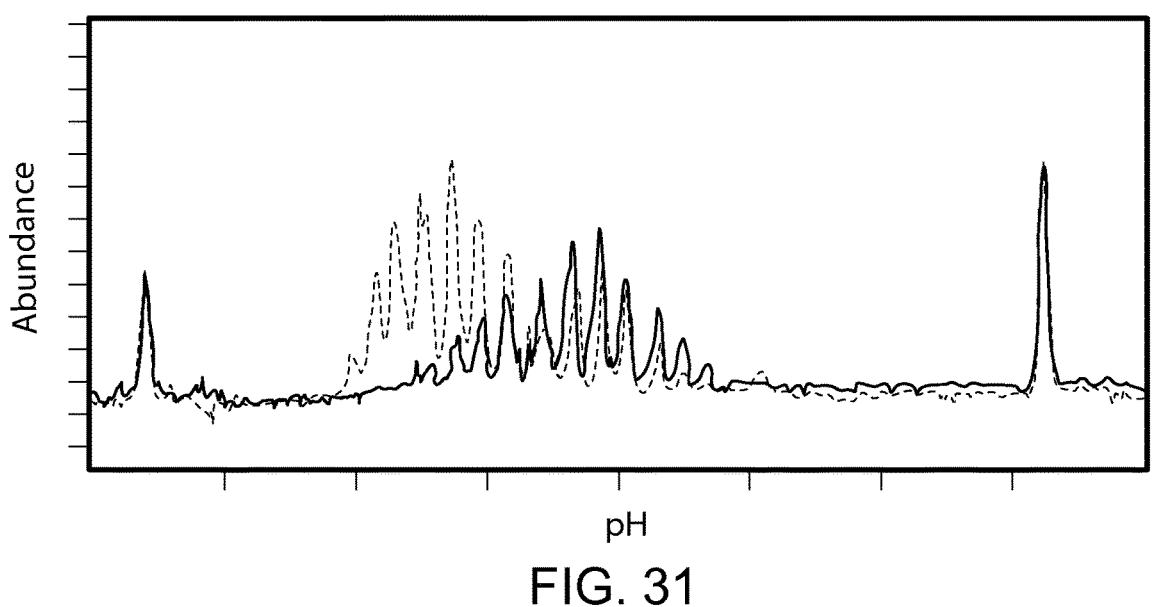
FIG. 31 is an imaged capillary isoelectric focusing (icIEF) peak profile of Fabrazyme® and Replagal®.

Imaged capillary isoelectric focusing (icIEF) was used to evaluate the protein charge of each tested protein. An electropherogram of Fabrazyme® and Replagal® are shown in FIG. 31. The relative percentages of low, mid, and high pI ranges of the electropherogram was determined for recombinant α-galactosidase-A protein provided herein (FZ2G) and Fabrazyme® and are shown in FIGS. 32A-C.

Reverse-Phase Chromatography

In another set of experiments, Fabrazyme® and Replagal® were analyzed using reverse-phase high pressure liquid chromatography (RP-HPLC). The samples were injected onto a YMC Octyl Column (Waters, 2.0×100 mm) and eluted using a linear TFA/acetonitrile gradient at a flowrate of 0.25 mL/minute. The eluted proteins were detected at 215 nm. The analyses were performed using an Agilent 1200 HPLC.

Figure 35:
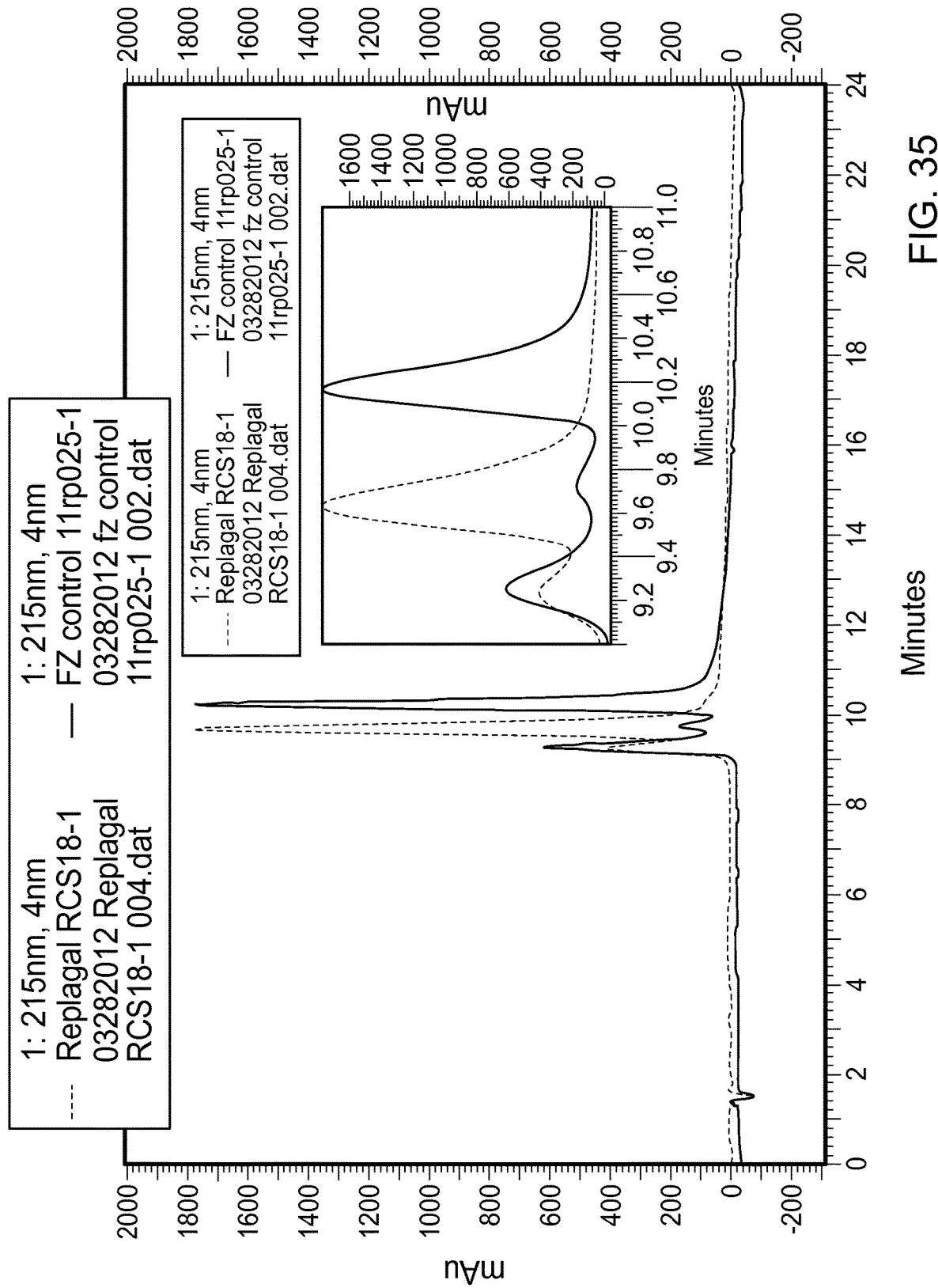
FIG. 35 is the elution profile of Fabrazyme® (blue) and Replagal® (green) from a reverse-phase high pressure liquid chromatography (RP-HPLC) column.
Figure 36:
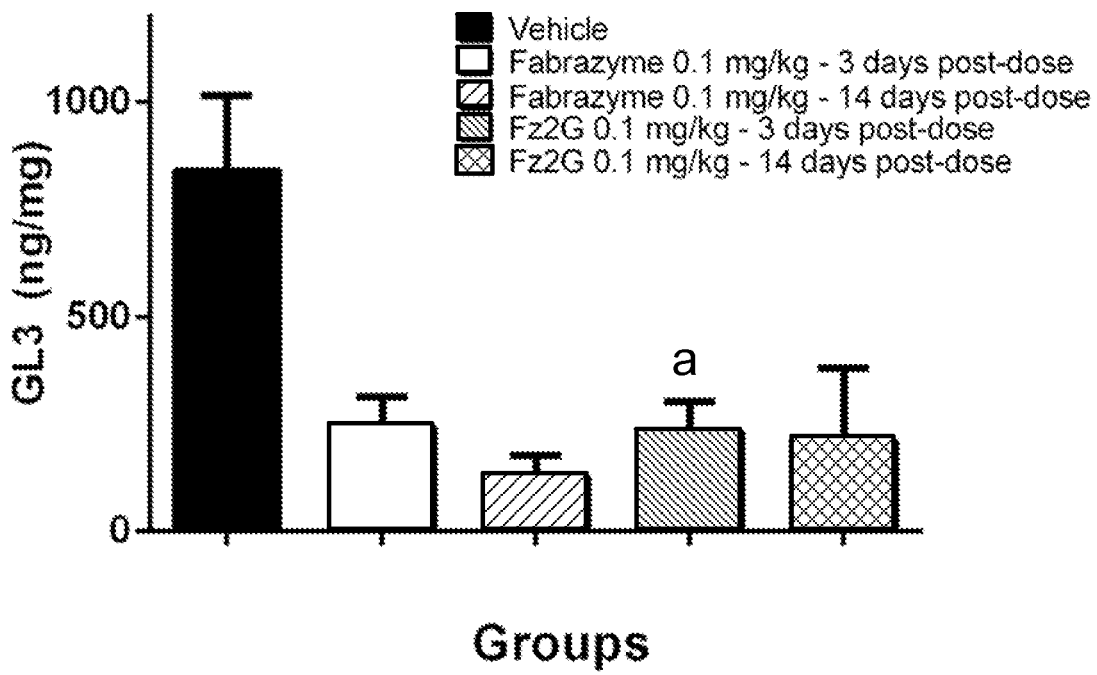
FIG. 36 is a graph showing the amount of GL3 in liver tissue (ng GL3/mg of liver tissue) in a Fabry mouse model 3 days or 14 days after a single intravenous administration of 0.1 mg/kg Fabrazyme®, or 3 days or 14 days after a single intravenous administration of 0.1 mg/kg of recombinant human α-galactosidase A protein provided herein (FZ2G), or in a Fabry mouse model intravenously administered a single dose of a vehicle. One sample was excluded from analysis, as it was calculated as being an outlier according to the Grubbs' test (p<0.01) (group indicated with an "a" in the graph).
Figure 37:
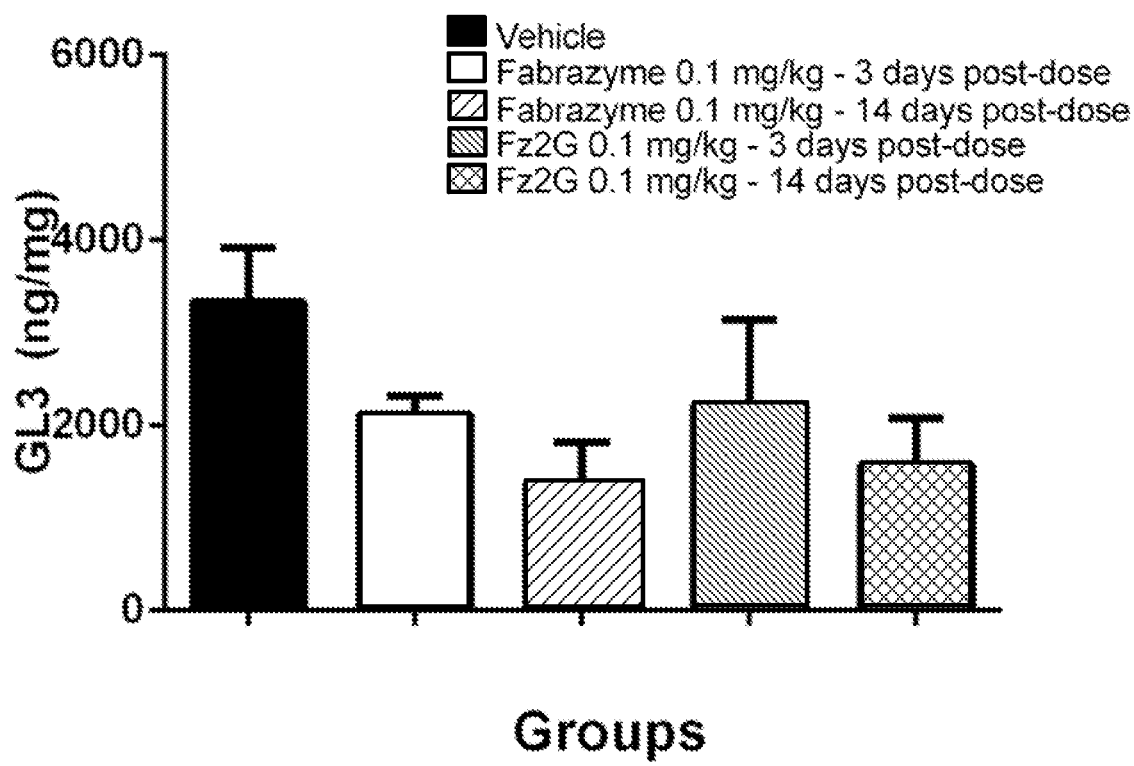
FIG. 37 is a graph showing the amount of GL3 in spleen tissue (ng GL3/mg of spleen tissue) in a Fabry mouse model 3 days or 14 days after a single intravenous administration of 0.1 mg/kg Fabrazyme®, or 3 days or 14 days after a single intravenous administration of 0.1 mg/kg of recombinant human α-galactosidase A protein provided herein (FZ2G), or in a Fabry mouse model intravenously administered a single dose of vehicle.
Figure 38:
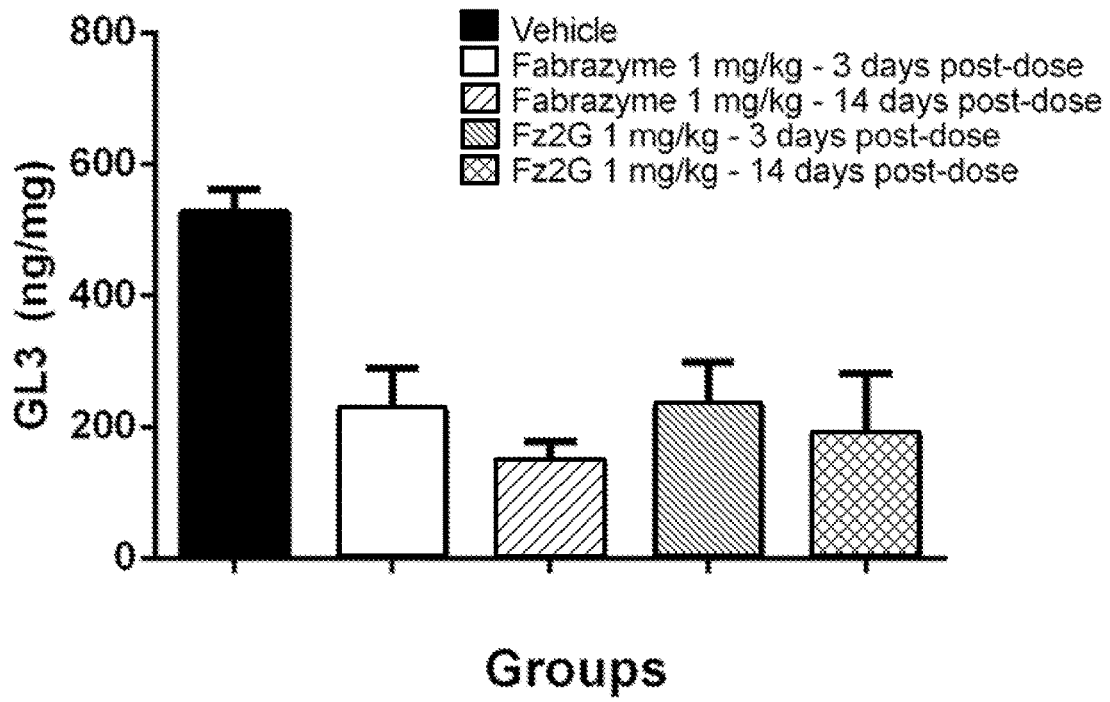
FIG. 38 is a graph showing the amount of GL3 in heart tissue (ng GL3/mg of heart tissue) in a Fabry mouse model 3 days or 14 days after a single intravenous administration of 1.0 mg/kg Fabrazyme®, or 3 days or 14 days after a single intravenous administration of 1.0 mg/kg of recombinant human α-galactosidase A protein provided herein (FZ2G), or in a Fabry mouse model intravenously administered a single dose of vehicle.
Figure 39:
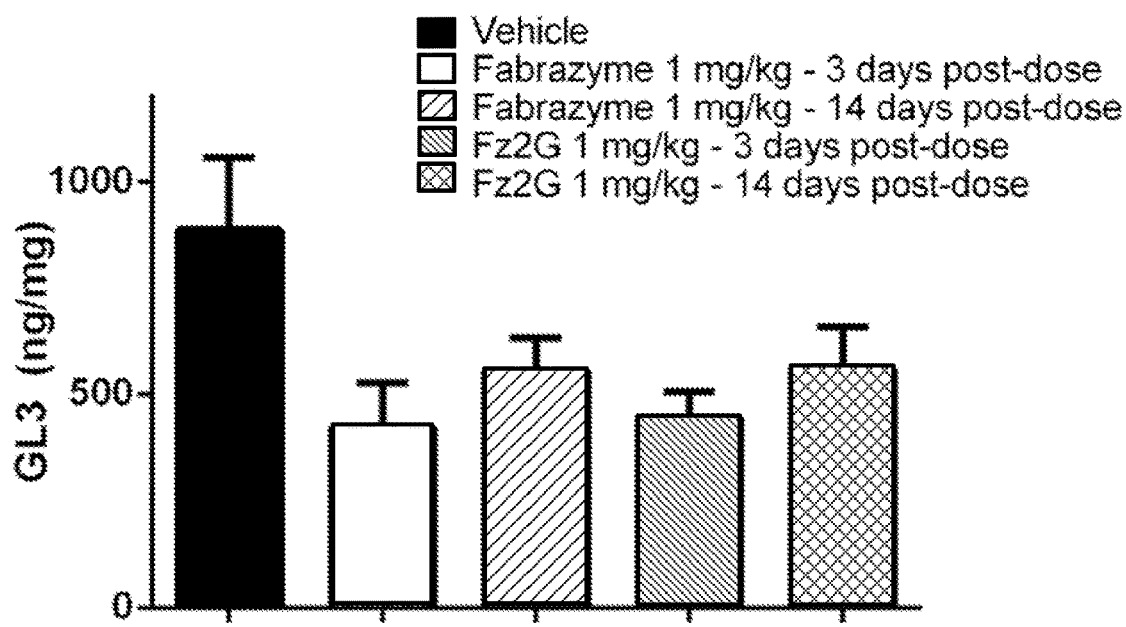
FIG. 39 is a graph showing the amount of GL3 in kidney tissue (ng GL3/mg of kidney tissue) in a Fabry mouse model 3 days or 14 days after a single intravenous administration of 1.0 mg/kg Fabrazyme®, or 3 days or 14 days after a single intravenous administration of 1.0 mg/kg of recombinant human α-galactosidase A protein provided herein (FZ2G), or in a Fabry mouse model intravenously administered a single dose of vehicle.

The data show that Replagal® elutes from the RP-HPLC column at an earlier time point than the Fabrazyme® (FIG. 35).

Example 4

Functional Characterization of Recombinant Human α-Galactosidase-A

Cation-Independent Mannose-6-Phosphate Receptor-Binding Activity

A set of Biacore experiments were performed to test the ability of recombinant human α-galactosidase-A protein provided herein, Fabrazyme®, and Replagal® to bind to the cation-independent mannose-6-phosphate receptor (CI-MPR).

Figure 26:
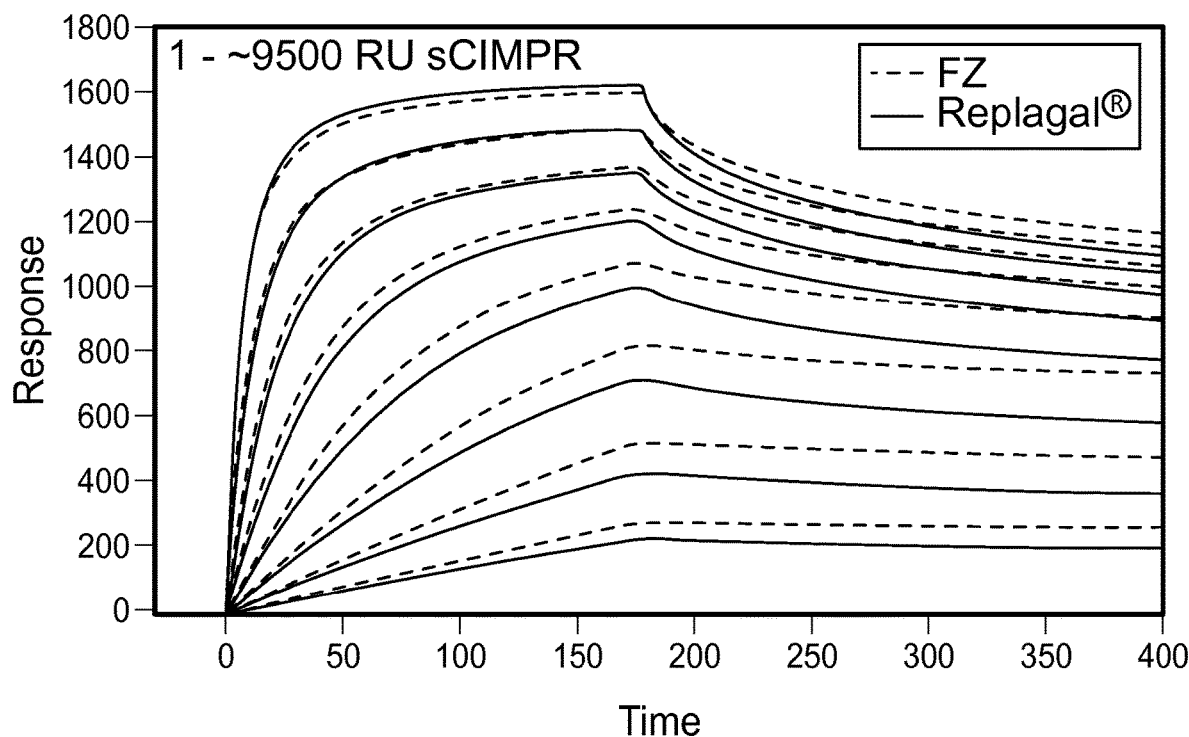
FIG. 26 is graph showing the surface plasmon resonance (Biacore) soluble cation independent mannose-6-phosphate receptor-binding data of Fabrazyme® (FZ) (red) and Replagal® (green).
Figure 27:
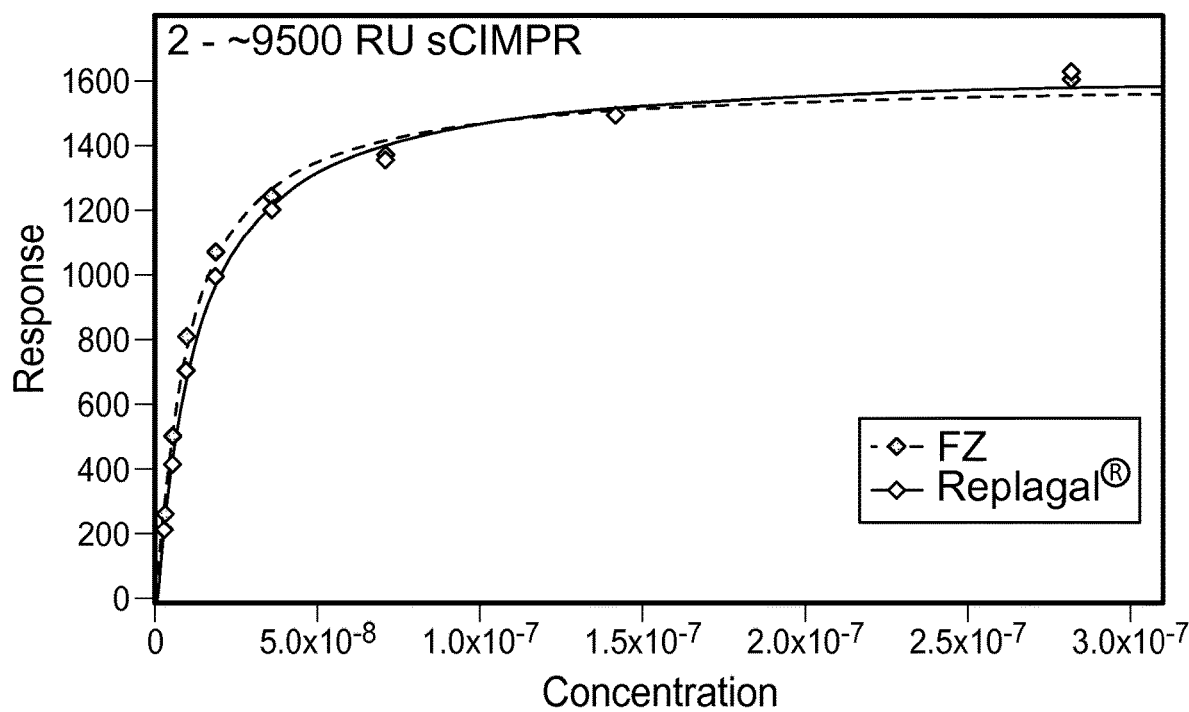
FIG. 27 is graph showing the surface plasmon resonance (Biacore) soluble cation independent mannose-6-phosphate receptor-binding data of Fabrazyme® (FZ) (red) and Replagal® (green).
Figure 28:
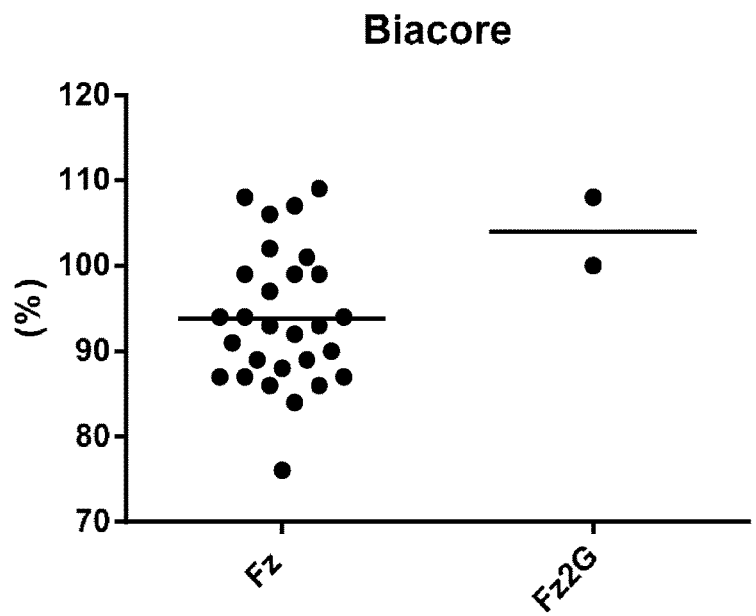
FIG. 28 is a graph showing the relative soluble cation independent mannose-6-phosphate receptor binding of Fabrazyme® (FZ) and recombinant human α-galactosidase-A protein provided herein (FZ2G), as determined by surface plasmon resonance (Biacore).

The Biacore sensorgrams for Fabrazyme® and Replagal® are shown in FIG. 26. Binding curves from these senorgrams of Fabrazyme® and Replagal® are shown in FIG. 27. A graph summarizing the CIMPR-binding activity of recombinant α-galactosidase-A protein provided herein (FZ2G) and Fabrazyme® are shown in FIG. 28. A comparison of these data show that recombinant human α-galactosidase-A protein provided herein (FZ2G) has increased CIMPR-binding activity as compared to Fabrazyme®.

Figure 29:
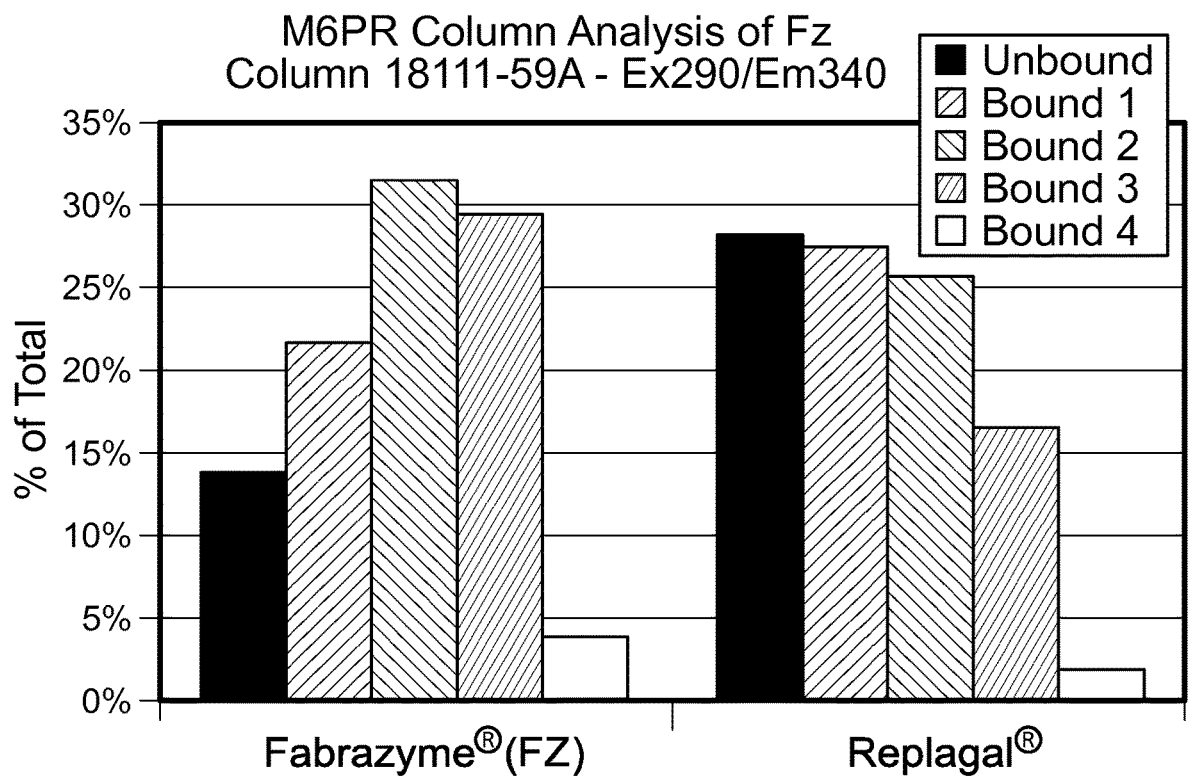
FIG. 29 is a graph showing the relative percentage of Fabrazyme® (FZ) and Replagal® eluted from a mannose-6-phosphate receptor affinity column with increasing concentrations of mannose-6-phosphate.
Figure 30:
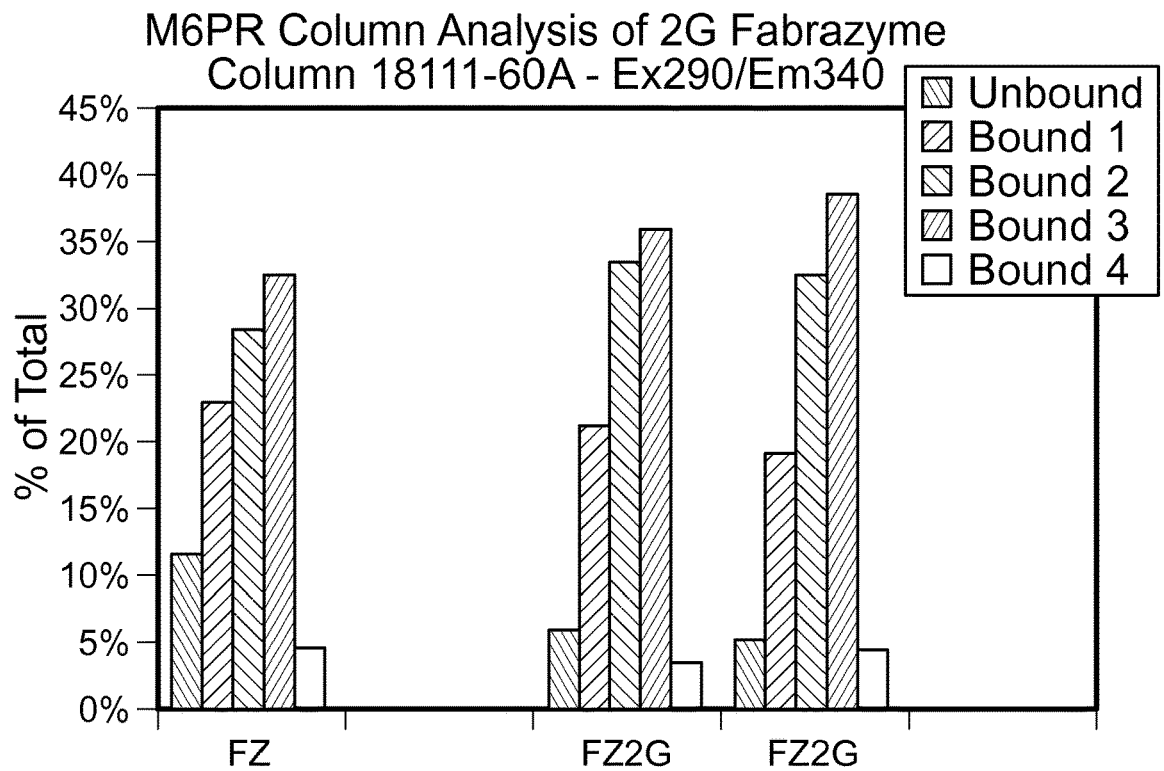
FIG. 30 is a graph showing the relative percentage of Fabrazyme® (FZ) and recombinant human α-galactosidase-A protein provided herein (FZ2G) eluated from a mannose-6-phosphate receptor affinity column with increasing concentrations of mannose-6-phosphate.

The ability of recombinant human α-galactosidase-A protein provided herein (FZ2G), Fabrazyme®, and Replagal® to bind to mannose-6-phosphate receptor was also tested using affinity column chromatography. The mannose-6-phosphate receptor columns were step eluted with mannose-6-phosphate and the percentage of total loaded recombinant protein eluting from the column in each elution fraction is shown in FIGS. 29 and 30). The data indicate that recombinant α-galactosidase-A protein provided herein (FZ2G) has a lower relative percentage of unbound and a higher percentage of high affinity species compared to Fabrazyme® and Replagal®.

$K_m$ and $V_{max}$

The $K_m$ and $V_{max}$ of recombinant human α-galactosidase-A protein provided herein (FZ2G) and Fabrazyme® were also determined.

Figure 33:
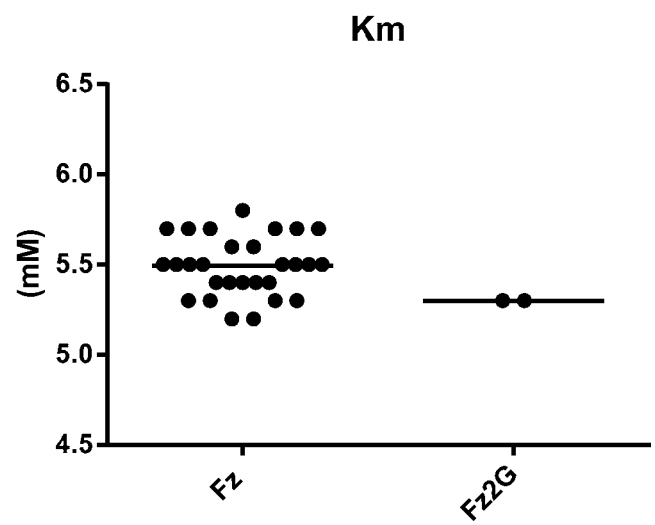
FIG. 33 is a graph of the $K_m$ of Fabrazyme® (FZ) and recombinant human α-galactosidase-A protein provided herein (FZ2G) determined using a synthetic pNP substrate.
Figure 34:
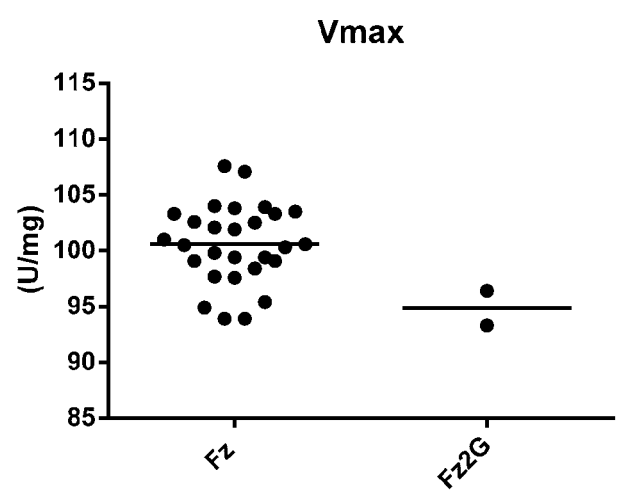
FIG. 34 is a graph of the $V_{max}$ of Fabrazyme® (FZ) and recombinant human α-galactosidase-A protein provided herein (FZ2G) determined using a synthetic pNP substrate.

The data show that recombinant human α-galactosidase-A protein provided herein (FZ2G) has a decreased or about the same $K_m$ as compared to Fabrazyme® (FIG. 33) and has about the same or a slightly decreased $V_{max}$ as compared to Fabrazyme® (FIG. 34).

In sum, the data provided herein show that recombinant human α-galactosidase-A protein provided herein (FZ2G) has an altered glycosylation pattern and an improved mannose-6-phosphate receptor-binding activity compared to Fabrazyme®.

Example 5

Animal Studies

Two animal model studies were performed to assess the effect of recombinant human α-galactosidase-A protein provided herein on GL-3 clearance and pharmacokinetic parameters.

The first study was conducted to investigate the effects of recombinant human α-galactosidase-A protein (as compared to Fabrazyme®) on tissue GL-3 clearance following a single intravenous (IV) administration at 0.1 mg/kg and 1 mg/kg in Fabry mice. In this study, 90 Fabry mice (46M/44F) were separated into 5 groups (see Table 2 below). The animals in Group 1 (n=10, 6M/4F) were administered a single IV administration of vehicle. The animals in Groups 2 and 3 (n=20 per group, 10M/10F) were administered a single IV administration of Fabrazyme® at 0.1 mg/kg and 1.0 mg/kg, respectively. The animals in Groups 4 and 5 (n=20 per group, 10M/10F) were administered a single IV administration of human recombinant α-galactosidase-A protein provided herein (FZ2G) at 0.1 mg/kg and 1.0 mg/kg, respectively. The wildtype animal in Group 6 (n=1M) was not treated and served as a control for GL-3 calibration. The animals were euthanized 3 days post-dose (Groups 2-5, n=10, 5M/5F per group) and 14 days post-dose (Group 1 and Groups 2-5, n=10, 5M/5F per group). GL-3 analysis was conducted on the following tissues: heart and kidney (Groups 1, 3, and 5), and spleen and liver (Groups 1, 2, and 4).

TABLE 2

GL-3 Clearance Study Design

| Group | Mouse Strain | # of Animals (M/F) | Test Article | Dose (mg/kg) | Dosing Regimen/ Dose Route | Blood Sample Timepoint & Analysis | Tissue Sample Timepoint & Analysis |
|---|---|---|---|---|---|---|---|
| 1 | Fabry | (10) 6/4 | Vehicle | — | Single dose/IV | Day 2 (Groups 2-5, n = 10, 5M/5F per group) for Lyso GL-3 analysis | Day 3 (Groups 2-5, n = 10, 5M/5F per group) for GL-3 and Lyso GL-3 analysis |
| 2 | | (20) 10/10 | Fabrazyme ® | 0.1 | | | |
| 3 | | (20) 10/10 | Fabrazyme ® | 1.0 | | Day 13 (Groups 1, 6, and Groups 2-5, n = 10, 5M/5F per group) for Lyso GL-3 analysis | Day 14 (Groups 1, 6, and Groups 2-5, n = 10, 5M/5F per group) for GL-3 and Lyso GL-3 analysis |
| 4 | | (20) 10/10 | Fz2G | 0.1 | | | |
| 5 | | (20) 10/10 | Fz2G | 1.0 | | | |
| 6 | SV129 | 1 (1/0) | | N/A | | | |

A summary of some of the functional and structural characteristics of the recombinant α-galactosidase-A protein provided herein (FZ2G) that was administered to the Fabry mice in the animal studies described in this Example is provided in Table 3 below.

The data show that a similar reduction in the accumulation of GL-3 in the liver, spleen, heart, and kidney in a mouse model of Fabry disease is achieved after intravenous administration of a single dose of Fabrazyme® or a single dose of recombinant human α-galactosidase-A protein provided herein (FZ2G) (see FIGS. 36, 37, 38, and 39, respectively). In sum, the data show that there is no statistically significant difference in GL-3 clearance in a mouse model of Fabry disease following a single intravenously-administered dose of Fabrazyme® or a single intravenously-administered dose of recombinant human α-galactosidase-A protein provided herein (FZ2G).

TABLE 3

Subset of Physical and Structural Characteristics of FZ2G Used in Animal Studies

| | Fabrazyme ® | FZ2G |
|---|---|---|
| Binding to M6Pr (%) | 100 | 130 |
| icIEF | | |
| Peaks 1-5 (%) | 51.3* | 60.4 |
| Peaks 6-11 (%) | 36.8* | 28.9 |
| Peaks 12-14 (%) | 11.9* | 10.7 |
| MALDI-TOF MS (m/z) | 50,828 | 50,743 |
| M6P content (mole/mole) | 1.7 | 2.0 |
| Sialic Acid content (mole/mole) | 2.8 | 3.1 |

The second study was conducted to characterize and compare the pharmacokinetic parameters of Fabrazyme® and recombinant human α-galactosidase-A protein provided herein (FZ2G) in Fabry mice following a single 1 mg/kg (IV) administration. In this study, 20 Fabry mice (12M/8F) are separated into 2 groups (see Table 4 below). The animals in Groups 1 and 2 (n=10 per group, 6M/4F) are administered a single IV administration of Fabrazyme® and recombinant human α-galactosidase-A protein provided herein (FZ2G) at 1.0 mg/kg, respectively. Blood samples are collected at 2, 15, 30, 60, 120, 240, and 480 minutes post-dose for enzyme analysis on dried blood spots. Pharmacokinetic analyses are conducted using Phoenix WinNonlin® (Pharsight Corporation, Mountain View, Calif.).

TABLE 4

Pharmacokinetics Study Design

| Group | # of Animals (M/F) | Test Article | Dose (mg/kg) | Dosing regimen | Sample Collection & Analysis |
|---|---|---|---|---|---|
| 1 | 10 (6/4) | Fabrazyme ® | 1 | Single dose/ IV | Blood samples collected at 2, 15, 30, 60, 120, 240, and 480 minutes post-dose for enzyme analysis on dried blood spots (DBS) |
| 2 | 10 (6/4) | Second Generation Fabrazyme (Fz2G) | 1 | | |

Figure 40:
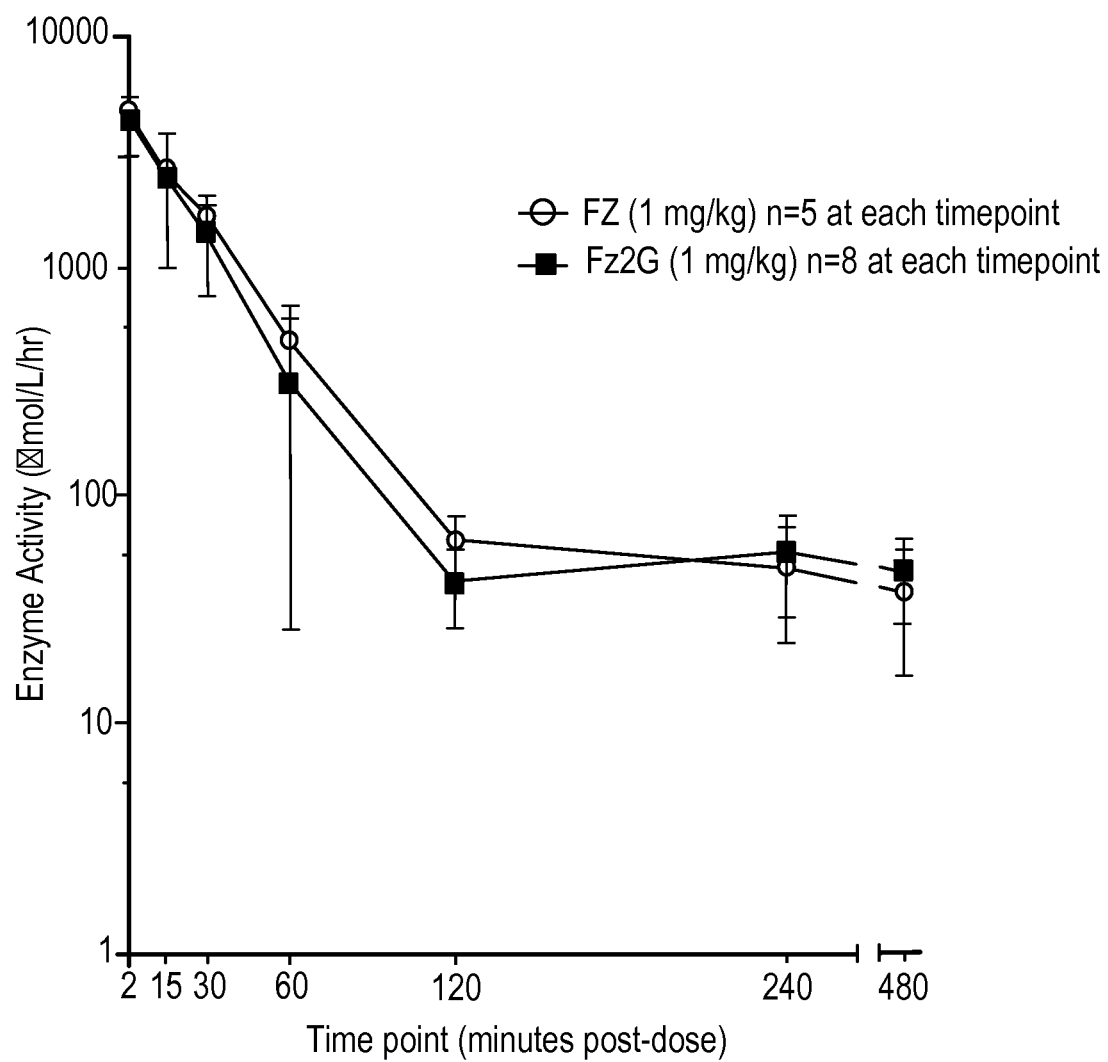
FIG. 40 is a graph showing the enzyme activity over time in a Fabry mouse model following a single intravenous administration of 1 mg/kg Fabrazyme® (circles; 5 mice at each time point) or 1 mg/kg recombinant human α-galactosidase-A protein provided herein (squares; 8 mice at each time point).

The data show that the pharmacokinetics of Fabrazyme® and recombinant human α-galactosidase-A protein provided herein (FZ2G) at the time points analyzed (FIG. 40) are similar. As the samples were collected as dried blood spots, the enzyme activity and not concentration was calculated at each time point. In sum, the data show similar enzyme activity between the enzymes following a single intravenous administration of Fabrazyme® and recombinant human α-galactosidase-A protein provided herein (FZ2G) at the time points analysed.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A recombinant human α-galactosidase-A (rhAGA) protein produced by a method comprising:
   (a) providing a Chinese hamster ovary (CHO) cell produced by a method comprising:
      (i) providing a CHO DXB11 cell line;
      (ii) sequentially culturing the CHO DXB11 cell line in:
         a cell culture medium comprising 5% fetal bovine serum for 3 days to 5 days;
         a cell culture medium comprising 2.5% fetal bovine serum for 3 days to 5 days; and
         a cell culture medium comprising no animal serum for about 5 days to 10 days; and
      (iii) generating a single-cell clone from the CHO cell resulting from step (ii), wherein the single-cell clone, when transfected with red fluorescent protein (RFP), would have a transfection efficiency of >30% RFP positive, a cell growth doubling time in a serum-free medium of <35 hours, and >75% culture viability, and further wherein the single-cell clone grows in a protein-free, animal derived component (ADC) free medium;
   (b) stably transfecting the single-cell clone from step (a) with an expression vector comprising a sequence encoding the rhAGA protein;
   (c) selecting a transfected clone that produces rhAGA;
   (d) culturing the clone in a protein-free, ADC-free medium; and
   (e) harvesting the rhAGA protein from the cell culture, wherein the rhAGA protein comprising a percentage of total N-linked oligosaccharides that are bis-mannose-6-phosphorylated oligosaccharides between 9.0% and 11.0%.

2. The rhAGA protein of claim 1, wherein the expression vector comprises a sequence encoding the rhAGA protein that is at least 90% identical to SEQ ID NO: 1.

3. The rhAGA protein of claim 1, wherein the amino acid sequence of the rhAGA protein comprises SEQ ID NO:3.

4. The rhAGA protein of claim 1, wherein the amino acid sequence of the rhAGA protein consists of SEQ ID NO:3.

5. The rhAGA protein of claim 1, wherein the amino acid sequence of the rhAGA protein consists of SEQ ID NO:2.

6. A recombinant human α-galactosidase-A (rhAGA) protein comprising:
   a percentage of total N-linked oligosaccharides that are bis-mannose-6-phosphorlyated oligosaccharides between 9.0% and 11.0%.

7. The rhAGA protein of claim 6, further comprising a percentage of total N-linked oligosaccharides that are monosialylated, nonfucose-containing oligosaccharides between 0.3% and 1.2%.

8. The rhAGA protein of claim 6, wherein the amino acid sequence of the rhAGA protein comprises SEQ ID NO:3.

9. The rhAGA protein of claim 6, wherein the amino acid sequence of the rhAGA protein consists of SEQ ID NO:3.

10. The rhAGA protein of claim 6, wherein the amino acid sequence of the rhAGA protein comprises SEQ ID NO:2.

11. The rhAGA protein of claim 6, further comprising:
    a percentage of total N-linked oligosaccharides that are triantennary, trisialylated oligosaccharides of form 2 that is between 6.0% and 8.0%; and
    a molar ratio of mannose-6-phosphate to protein that is between 1.8-3.0.

12. The rhAGA protein of claim 6, further comprising at least one of:
    a percentage of total N-linked oligosaccharides that are neutrally-charged oligosaccharides between 0.1% and 2.0%;
    a percentage of total N-linked oligosaccharides that are monosialylated fucose-containing oligosaccharides between 0.1% and 2.0%;
    a percentage of total N-linked oligosaccharides that are triantennary, trisialylated oligosaccharides of form 1 between 0.1% and 5.0%;
    a percentage of total N-linked oligosaccharides that are tetrasialylated oligosaccharides between 6.0% and 8.0%; and
    a percentage of total N-linked oligosaccharides that are monosialylated and monophosphorylated between 8.5% and 10.5%.

13. A pharmaceutical composition comprising the rhAGA protein of claim 1, and a pharmaceutically acceptable carrier.

14. A pharmaceutical composition comprising the rhAGA protein of claim 2, and a pharmaceutically acceptable carrier.

15. A pharmaceutical composition comprising the rhAGA protein of claim 3, and a pharmaceutically acceptable carrier.

16. A pharmaceutical composition comprising the rhAGA protein of claim 4, and a pharmaceutically acceptable carrier.

17. A pharmaceutical composition comprising the rhAGA protein of claim 5, and a pharmaceutically acceptable carrier.

18. A pharmaceutical composition comprising the rhAGA protein of claim 6, and a pharmaceutically acceptable carrier.

19. A pharmaceutical composition comprising the rhAGA protein of claim 7, and a pharmaceutically acceptable carrier.

20. A pharmaceutical composition comprising the rhAGA protein of claim 8, and a pharmaceutically acceptable carrier.

21. A pharmaceutical composition comprising the rhAGA protein of claim 9, and a pharmaceutically acceptable carrier.

22. A pharmaceutical composition comprising the rhAGA protein of claim 10, and a pharmaceutically acceptable carrier.

23. A pharmaceutical composition comprising the rhAGA protein of claim 11, and a pharmaceutically acceptable carrier.

24. A pharmaceutical composition comprising the rhAGA protein of claim 12, and a pharmaceutically acceptable carrier.

* * * * *

UNITED STATES PATENT AND TRADEMARK OFFICE
CERTIFICATE OF CORRECTION

PATENT NO. : 11,208,644 B2
APPLICATION NO. : 15/030555
DATED : December 28, 2021
INVENTOR(S) : Lee et al.

It is certified that error appears in the above-identified patent and that said Letters Patent is hereby corrected as shown below:

In the Claims

In Claim 1, Column 71, Lines 26-27:
"positive, a cell growth doubling time in a serum-free medium of < 35 hours, and > 75% culture viability,"
Should read:
"positive, a cell growth doubling time in a serum-free culture medium of < 35 hours, and > 75% culture viability,".

Signed and Sealed this
Eighth Day of March, 2022

Drew Hirshfeld
*Performing the Functions and Duties of the
Under Secretary of Commerce for Intellectual Property and
Director of the United States Patent and Trademark Office*